US011680241B2

(12) United States Patent
Sawyer et al.

(10) Patent No.: US 11,680,241 B2
(45) Date of Patent: Jun. 20, 2023

(54) PERFUSION ENABLED BIOREACTORS

(71) Applicant: University of Florida Research Foundation, Inc., Gainesville, FL (US)

(72) Inventors: Wallace Gregory Sawyer, Gainesville, FL (US); Samantha Lauren Marshall, New York, NY (US); Eric O. McGhee, Gainesville, FL (US); Alexander McGhee, Philadelphia, PA (US); Kylie E. Van Meter, Gainesville, FL (US); Angela Athena Pitenis, Gainesville, FL (US); Juan Manuel Urueña, Philadelphia, PA (US); Derek L. Hood, Gainesville, FL (US); Michael Dougherty, Gainesville, FL (US); Christian Jobin, Gainesville, FL (US); Jack E. Famiglietti, Gainesville, FL (US); Ryan A. Smolchek, Gainesville, FL (US); Padraic P. Levings, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 424 days.

(21) Appl. No.: 16/936,912

(22) Filed: Jul. 23, 2020

(65) Prior Publication Data

US 2020/0354668 A1    Nov. 12, 2020

Related U.S. Application Data

(63) Continuation-in-part of application No. PCT/US2019/017316, filed on Feb. 8, 2019.
(Continued)

(51) Int. Cl.
*C12M 1/34* (2006.01)
*C12M 3/00* (2006.01)
(Continued)

(52) U.S. Cl.
CPC ............ *C12M 41/46* (2013.01); *C12M 21/08* (2013.01); *C12M 23/16* (2013.01); *C12M 23/22* (2013.01);
(Continued)

(58) Field of Classification Search
CPC ...... C12M 41/46; C12M 41/48; C12M 41/36; C12M 21/08; C12M 23/16; C12M 23/22;
(Continued)

(56) References Cited

U.S. PATENT DOCUMENTS

| 2,340,110 A | 1/1944 | D'Aielio |
| 2,340,111 A | 1/1944 | D'Aielio |

(Continued)

FOREIGN PATENT DOCUMENTS

| DE | 20307590 U1 | 7/2003 | |
| GB | 2367069 | * 3/2002 | ............... C12M 1/34 |

(Continued)

OTHER PUBLICATIONS

International Search Report issued for PCT/US2019/017316, dated Apr. 26, 2019.
(Continued)

*Primary Examiner* — Michael L Hobbs
(74) *Attorney, Agent, or Firm* — Thomas | Horstemeyer, LLP

(57) ABSTRACT

Disclosed herein is a bioreactor system that allows active perfusive flow through a porous support medium enabling 3D growth of biological samples. In some embodiments, the system comprises a sample well filled with a three-dimensional (3D) cell growth medium. The system can further comprise a liquid medium reservoir fluidly connected to the sample well by a first filter material. The system can further comprises a medium collection chamber fluidly connected to the sample well by a second filter material. In some embodi-
(Continued)

ments, application of negative gage pressure to the medium collection chamber or positive pressure to the liquid medium reservoir draws fluid from the liquid medium reservoir, through the first filter material, into the sample well where it permeates the three-dimensional cell growth medium, through the second filter material, and finally into the medium collection chamber.

24 Claims, 37 Drawing Sheets

Related U.S. Application Data

(60) Provisional application No. 62/972,091, filed on Feb. 10, 2020, provisional application No. 62/912,396, filed on Oct. 8, 2019, provisional application No. 62/756,732, filed on Nov. 7, 2018, provisional application No. 62/628,011, filed on Feb. 8, 2018.

(51) Int. Cl.
| | |
|---|---|
| *C12M 3/06* | (2006.01) |
| *C12M 1/00* | (2006.01) |
| *C12M 1/36* | (2006.01) |
| *C12N 5/00* | (2006.01) |
| *C12M 1/12* | (2006.01) |

(52) U.S. Cl.
CPC ............ *C12M 23/44* (2013.01); *C12M 25/14* (2013.01); *C12M 29/10* (2013.01); *C12M 41/48* (2013.01); *C12N 5/0062* (2013.01); *C12M 41/36* (2013.01)

(58) Field of Classification Search
CPC ...... C12M 23/44; C12M 25/14; C12M 25/16; C12M 29/10; C12M 29/14; C12N 5/0062
See application file for complete search history.

(56) References Cited

U.S. PATENT DOCUMENTS

| | | | |
|---|---|---|---|
| 2,533,635 | A | 12/1950 | Seymour et al. |
| 3,940,351 | A | 2/1976 | Schlatzer, Jr. |
| 4,062,817 | A | 12/1977 | Westerman |
| 4,657,867 | A | 4/1987 | Guhl et al. |
| 5,034,486 | A | 7/1991 | Tazi et al. |
| 5,034,487 | A | 7/1991 | Tazi et al. |
| 5,034,488 | A | 7/1991 | Tazi et al. |
| 5,349,030 | A | 9/1994 | Long, II et al. |
| 5,748,827 | A | 5/1998 | Holl et al. |
| 5,809,360 | A | 9/1998 | Blake et al. |
| 6,486,401 | B1 | 11/2002 | Warhurst et al. |
| 7,114,924 | B2 | 10/2006 | Munsh |
| 7,208,125 | B1 | 4/2007 | Dong |
| 7,767,446 | B2 | 8/2010 | Robbins et al. |
| 8,066,961 | B2 | 11/2011 | Costello, III et al. |
| 8,318,479 | B2 | 11/2012 | Domansky et al. |
| 8,871,499 | B2 | 10/2014 | Tschumperlin et al. |
| 10,119,112 | B2 | 11/2018 | Leallais et al. |
| 2005/0260745 | A1 | 11/2005 | Domansky et al. |
| 2006/0110822 | A1 | 5/2006 | Robbins et al. |
| 2007/0207537 | A1 | 9/2007 | Cui et al. |
| 2007/0274871 | A1 | 11/2007 | Jiang et al. |
| 2010/0009335 | A1* | 1/2010 | Joseph .................. C12M 23/22 435/286.1 |
| 2011/0020929 | A1 | 1/2011 | Schrober et al. |
| 2011/0130310 | A1 | 6/2011 | Schoeber et al. |
| 2011/0212493 | A1 | 9/2011 | Hirschel et al. |
| 2014/0004020 | A1 | 1/2014 | Tubbs et al. |
| 2015/0125942 | A1* | 5/2015 | Grier, Jr. .......... G01N 33/48728 435/305.2 |

FOREIGN PATENT DOCUMENTS

| | | |
|---|---|---|
| JP | 2007-537759 A | 12/2000 |
| JP | 2008513013 A | 5/2008 |
| WO | WO2006033935 A2 | 9/2005 |
| WO | 2006033935 A2 | 3/2006 |
| WO | 2009141163 A3 | 11/2009 |
| WO | 2010048417 A3 | 4/2010 |
| WO | 2016182969 A1 | 11/2016 |
| WO | 2017049066 A1 | 3/2017 |
| WO | WO-2017049066 A1 * | 3/2017 ............ C12M 21/08 |
| WO | 2017062629 A1 | 4/2017 |

OTHER PUBLICATIONS

Stephens et al., Perfusion Flow Bioreactor for 3D In Situ Imaging: Investigating Cell/Biomaterials Interactions, Biotechnology and Bioengineering, vol. 97, No. 4, p. 952-961 2007.
Domansky et al.., Perfused Multiwell Plate for 3D Liver Tissue Engineering, Lab Chip., 10(1): 51-58, 2010.
Extended Search Report issued for 19 751 033.2, dated Oct. 4, 2021.
Marshall Samantha Lauren: "Microgels for in Vitro Three-Dimensional Cancer Models", Apr. 5, 2018 (Apr. 5, 2018), pp. 1-94, XP055843117, U RL:https://ufdcimages. uflib. ufl.edu/U F/E0/05/ 20/99/0001 /Marshall_S.pdf.
Domansky et al, "Perfused Multi-well Plate for 3D Liver Tissue Engineering", : Lab Chip, vol. 10, pp. 51-54, Date: Oct. 22, 2009.
Pörtner et al., "Bioreactor Design for Tissue Engineering", Journal of Bioscience and Bioengineering, vol. 100, Issue: 3, p. 235-245, Date: Sep. 2005.
Princz et al., "Automated Bioreactor System F\for Cartilage Tissue Engineering of Human Primary Nasal Septal Chondrocytes", Biomed Tech, vol. 62, Issue: 5, p. 481-486, Date: Oct. 26, 2017.
Ma et al. "A Novel 96well-formatted Micro-gap Plate Enabling Drug Response Profiling on Primary Tumour Samples." Sci Rep. 2015; 5: 9656. Published online Apr. 13, 2015.
"Simport Combi-BoxTM Storage Box" https://www.thomassci.com/ Laboratory-Supplies/Racks/_/Combi-Box-Storage-Box?=&q=Plate+ Storage (accessed before Nov. 7, 2018).
Bancroft et al., "Fluid Flow Increases Mineralized Matrix Deposition in 3D Perfusion Culture of Marrow Stromal Osteoblasts in a Dose-Dependent Manner", Proceedings of the National Academy of Sciences of the United States of America (PNAS) vol. 99, Issue: 20, p. 12600-12605, Date: Oct. 1, 2002.
JP Office action for JP Appln No. 2020-564794 dated Feb. 28, 2023.

* cited by examiner

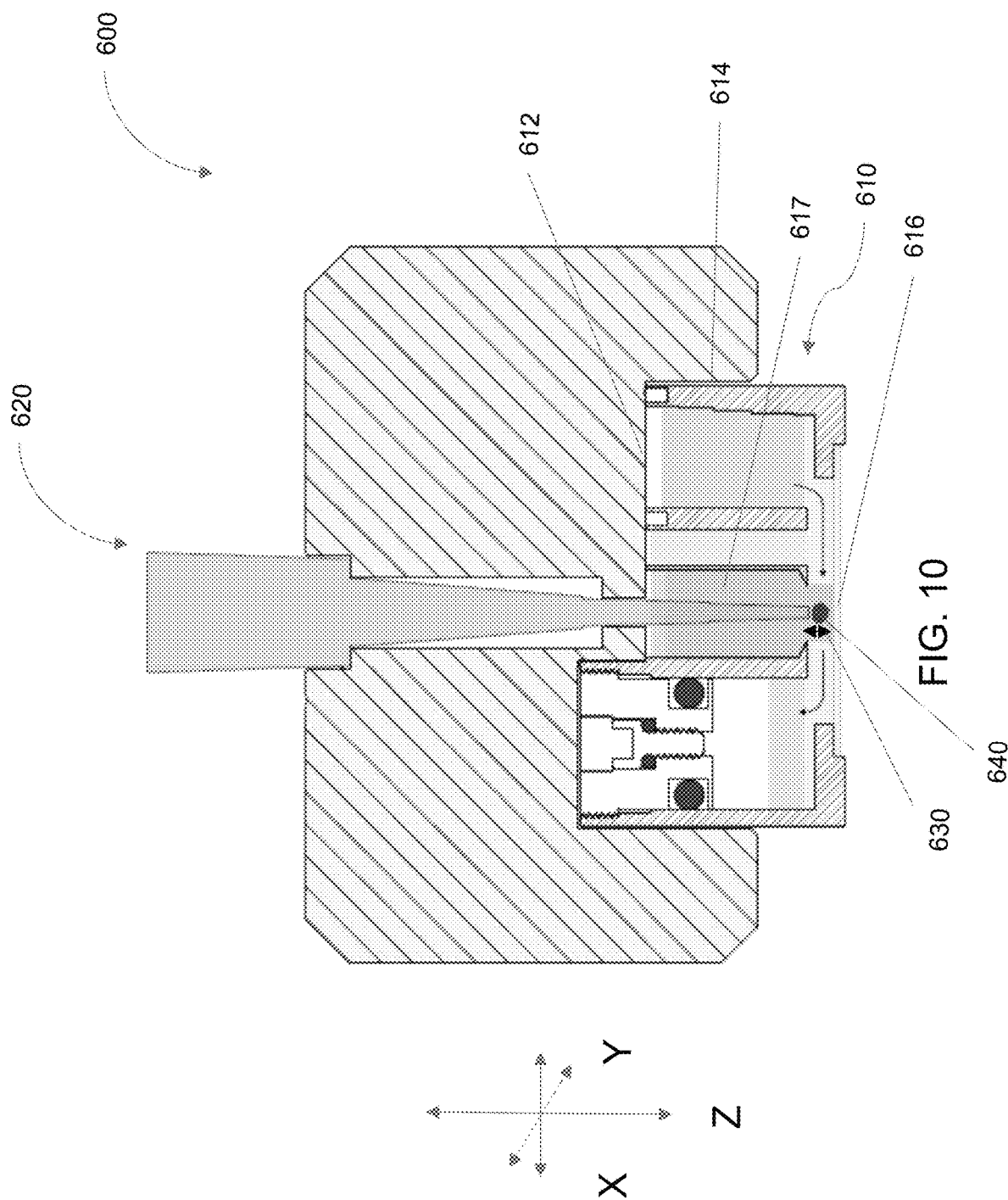

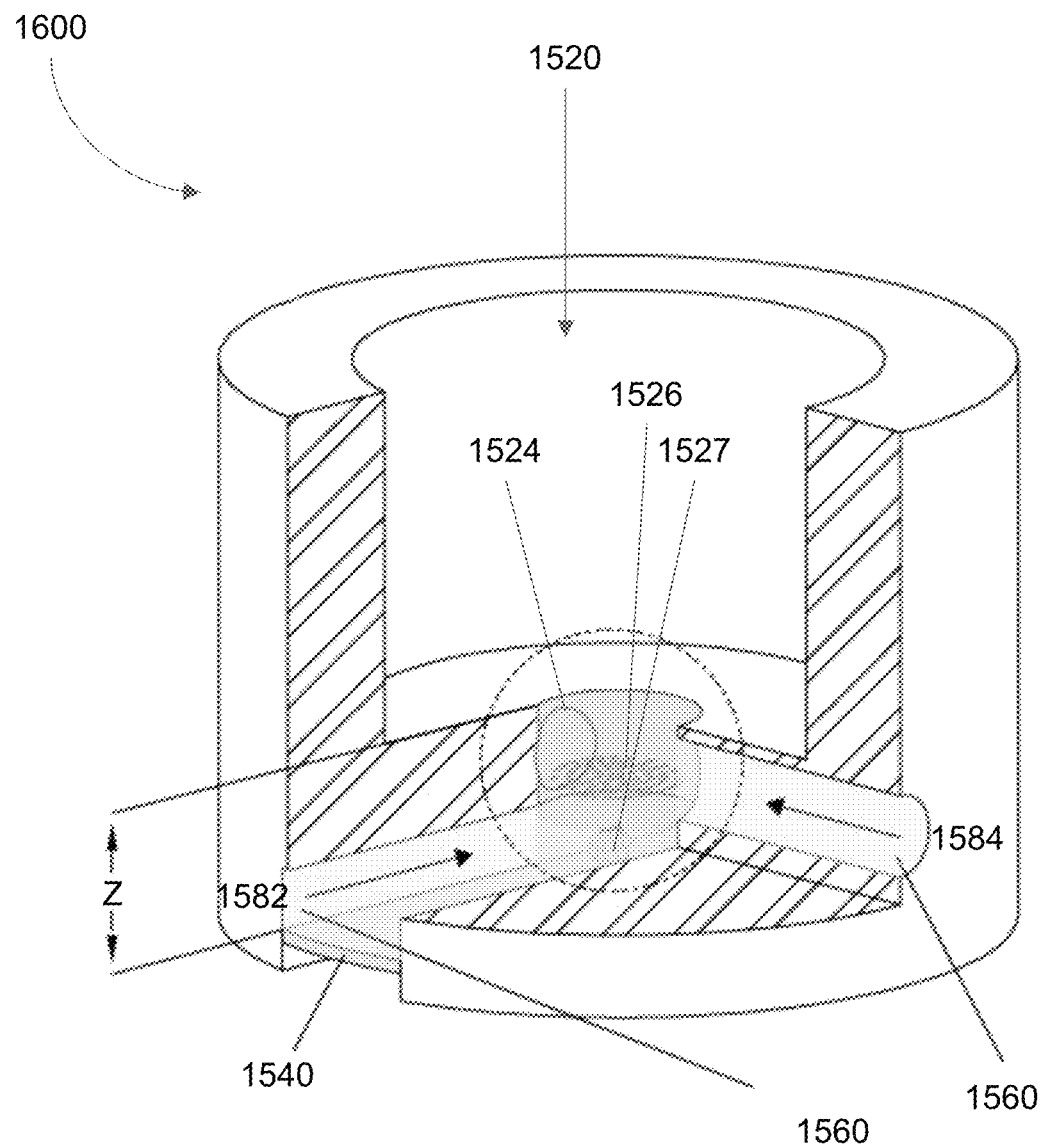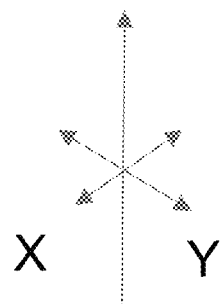
FIG. 21

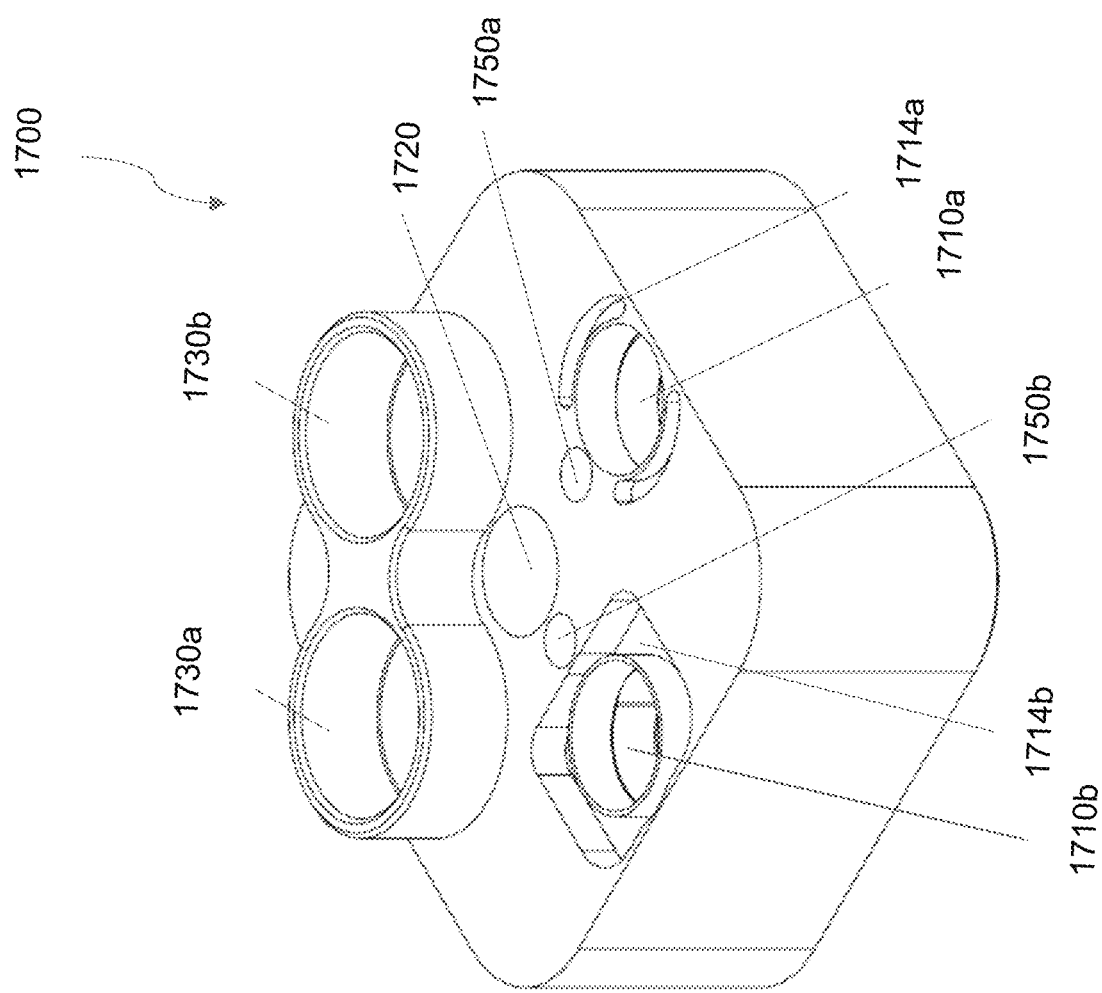
FIG. 23A
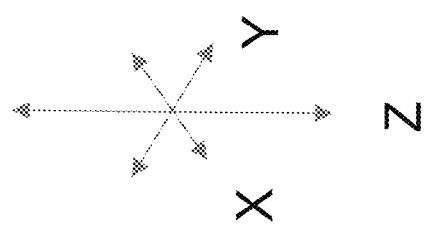

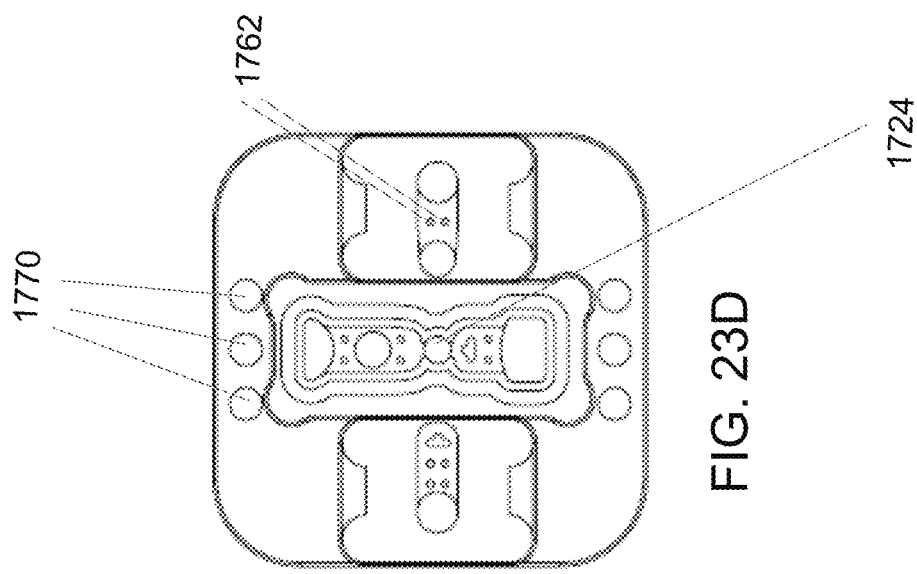
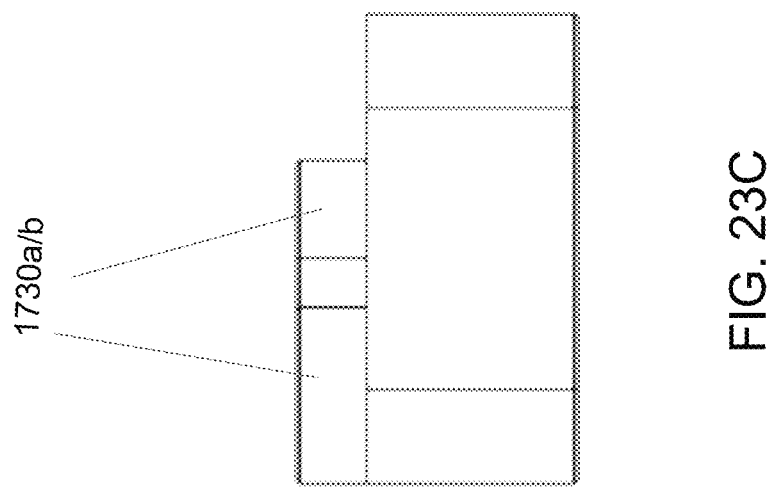
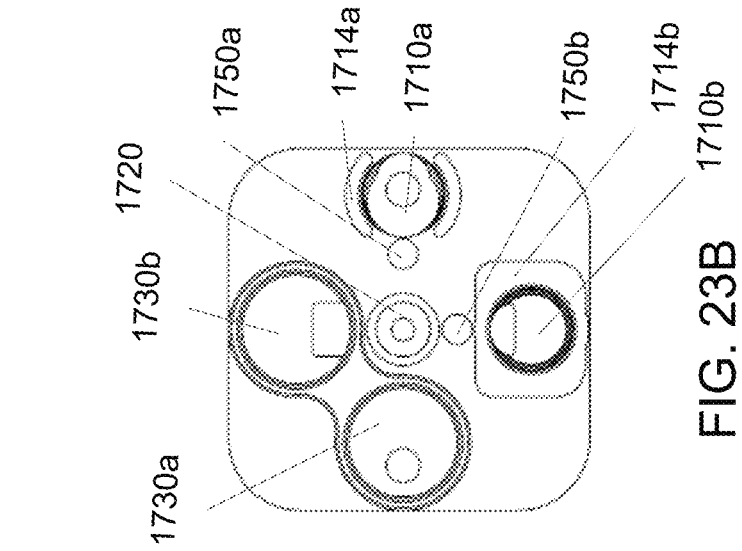
FIG. 23D
FIG. 23C
FIG. 23B

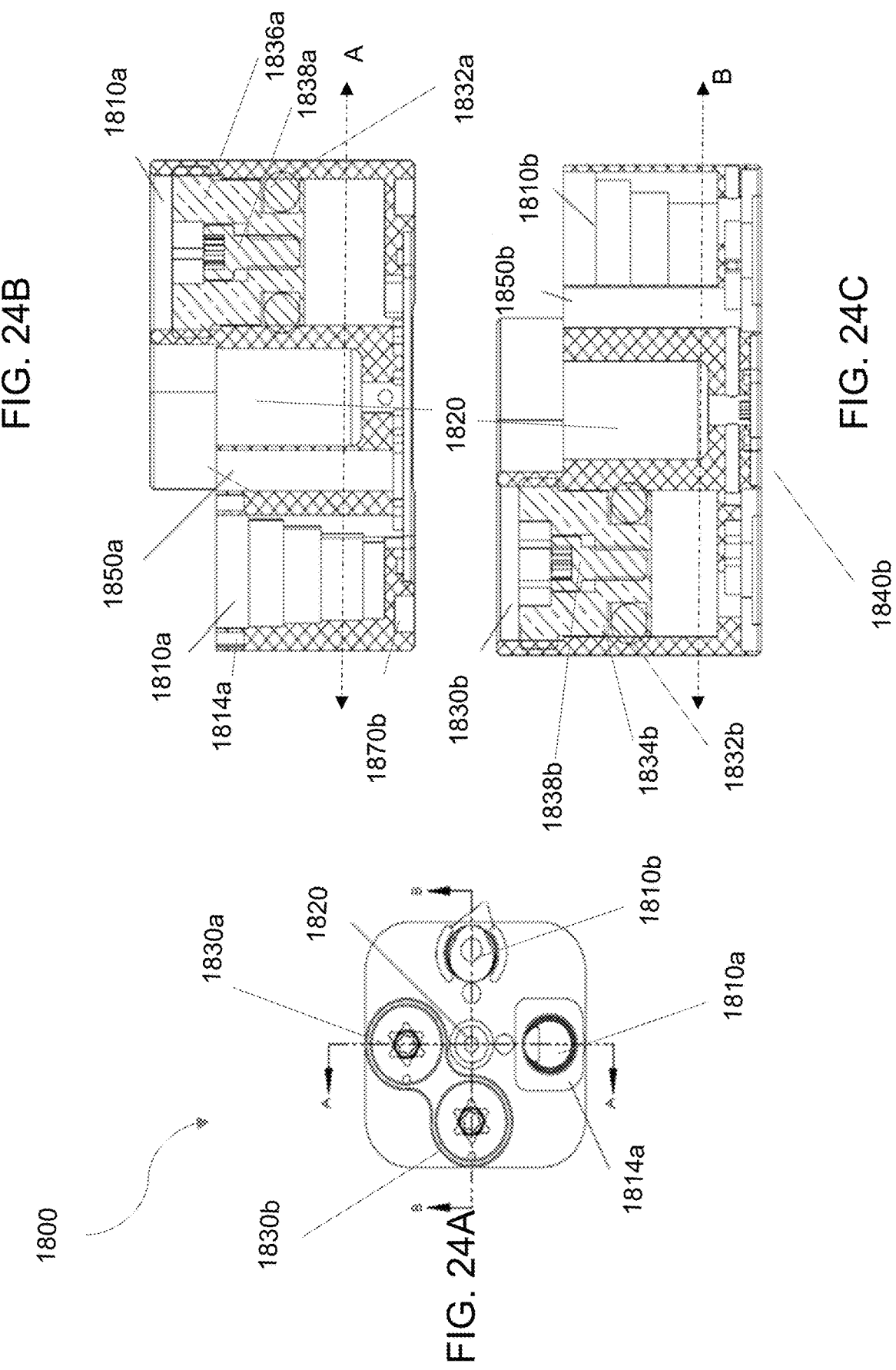

2000
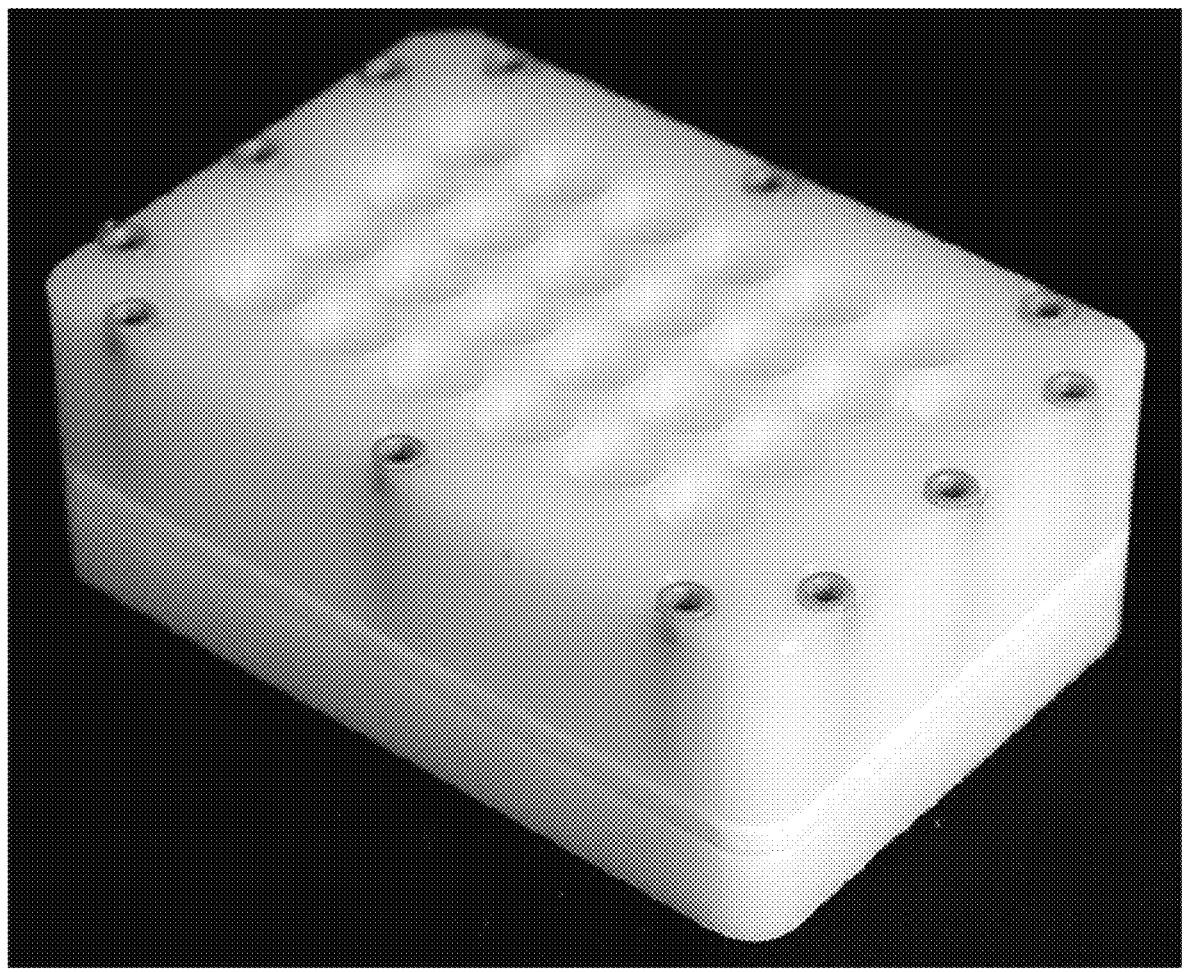
FIG. 26
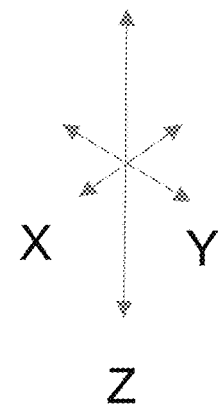

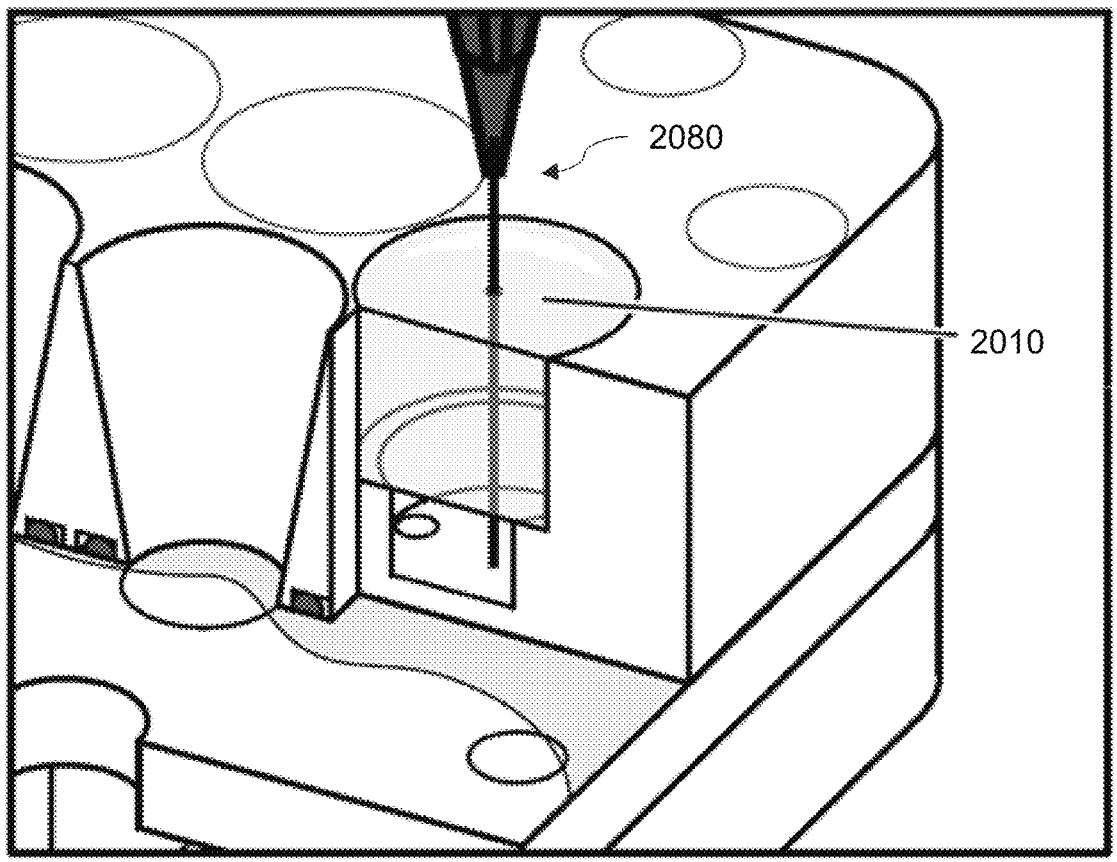
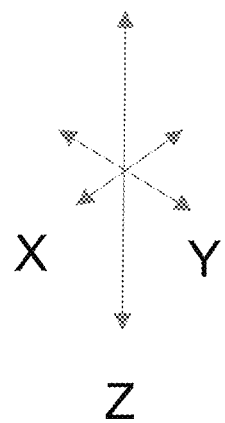
FIG. 29B

PERFUSION ENABLED BIOREACTORS

CROSS-REFERENCE TO RELATED APPLICATIONS

This application is a continuation-in-part of International Application No. PCT/US2019/017316, filed Feb. 8, 2019, which claims benefit of U.S. Provisional Application No. 62/628,011, filed Feb. 8, 2018, and U.S. Provisional Application No. 62/756,732, filed Nov. 7, 2018, which are hereby incorporated herein by reference in their entireties. This application also claims benefit of U.S. Provisional Application No. 62/912,396, filed Oct. 8, 2019, and U.S. Provisional Application No. 62/972,091, filed Feb. 10, 2020, which are hereby incorporated herein by reference in their entireties.

BACKGROUND

The printing or placement of biological samples (e.g., cells, cell layers, tissues) into a 3D support medium more accurately and reproducibly models cellular morphology, heterogeneity, and genetic profiles seen in vivo compared to conventional 2D culture. Some existing 3D cell culture techniques rely on polymer scaffolds in which cells are seeded and allowed to adhere. Once the cells are adhered to the scaffold, perfusion of growth media can begin. This method has several disadvantages: (1) cell migration is limited or precluded, (2) cell environments are defined by the structure of the polymer scaffold, (3) the experimental setup is not time-effective, and (4) does not include optical access for microscopy. In addition, cell viability for existing 3D culture methods is generally limited to several days; the passive 3D support medium cannot efficiently expel cellular waste, leading to localized cytotoxic environments and subsequent cell death.

SUMMARY

Disclosed herein is a bioreactor system that allows active perfusive flow through a porous support medium enabling 3D growth of biological samples. In some embodiments, the system comprises a sample well filled with a three-dimensional (3D) cell growth medium. The system can further comprise a liquid medium reservoir fluidly connected to the sample well by a first filter material. The system can further comprise a medium collection chamber fluidly connected to the sample well by a second filter material. In some embodiments, application of negative gage pressure to the medium collection chamber or positive pressure to the liquid medium reservoir draws fluid from the liquid medium reservoir, through the first filter material, into the sample well where it permeates the three-dimensional cell growth medium, through the second filter material, and finally into the medium collection chamber.

In some embodiments, a plurality of cells are disposed in a region of the 3D cell culture medium. One advantage of the disclosed system is the ability to have continuous optical access during the growth of the biological samples. Therefore, in some embodiments, the bottom of the sample well is optically transparent. For example, the bottom of the sample well can be composed of a glass or plastic material.

The disclosed bioreactor system can further comprise a vacuum apparatus operably connected to the medium collection chamber. For example, the vacuum apparatus can comprise a set screw rotatably mounted within the medium collection chamber. In some cases, the medium collection chamber comprises a vacuum port fluidly connected to the medium collection chamber that is releasably connectable to a vacuum apparatus.

The system can contain a single sample well. However, in some cases, the system comprises an array of sample wells isolated from each other that are all fluidly connected to the same medium collection chamber. Additionally, the sample medium collection chambers may be isolated and allow collection of liquid media for each well, thereby allowing isolated analyte collection. In these embodiments, each of the sample wells in the array can either be fluidly connected to separate liquid medium reservoirs, or fluidly connected to the same liquid medium reservoir.

In some embodiments, the system has an annular arrangement comprising an outer ring, a middle ring, and a central chamber. For example, the liquid medium reservoirs can be located in the outer ring, the sample well can be located in the middle ring, and the center chamber can be the medium collection chamber. In these embodiments, media flows radially inward, e.g., when negative gage pressure is applied to the central (media collection) chamber. As another example, the system can have an annular arrangement comprising an outer ring and a central chamber, where the sample well is located in the central chamber, the media collection chamber is in the outer ring, and the liquid medium reservoir is located above the sample well in the central chamber. In these embodiments, media flows radially outward, e.g., when negative gage pressure is applied to the outer ring (media collection chamber).

The disclosed system can be used with any 3D cell growth medium. In preferred embodiments, the 3D cell growth medium comprises a plurality of hydrogel particles and a liquid cell culture medium, wherein the hydrogel particles are swelled with the liquid cell culture medium to form a granular gel. In some cases, the 3D cell growth medium has a yield stress such that the cell growth medium undergoes a transition from a jammed state to an unjammed state upon application of a shear stress greater than the yield stress. For example, the yield stress can be on the order of 10 Pa. In some cases, the concentration of hydrogel particles is between 0.05% to about 1.0% by weight.

In some embodiments, the hydrogel particles have a size between about 0.1 μm to about 100 μm when swollen with the liquid cell culture medium. The filter materials of the disclosed systems ensure that none of the hydrogel particles or cells escape the sample well during perfusion. Therefore, in some embodiments, the second filter material has a porosity smaller than the size of the swollen hydrogel particles. Likewise, in some embodiments, the first filter material is not present or needed based on the direction of flow. When present, the first filter material can be present to confine the 3D cell growth medium in the sample well, e.g. during shipping. In general, when present, the first filter material has a porosity smaller than the size of the swollen hydrogel particles.

In some embodiments, the second filter material contains one or more agents that can bind and sequester biological targets in the waste media, such as enzymes, cytokines, and chemokines. In this way, the filter may be removed for subsequent analysis to determine the state of health of the living biological sample suspended in the perfusion chamber. The agent can be, for example, a functionalized nanoparticle. In particular, the nanoparticle can contain on its surface a binding agent, such as an antibody or aptamer, which specifically binds the biological targets.

The details of one or more embodiments of the present disclosure are set forth in the accompanying drawings and the description below. Other features, objects, and advantages of the present disclosure will be apparent from the description and drawings, and from the claims.

Described herein are microscopy-enabled bioreactor systems. Microscopy-enabled bioreactor systems as described herein can comprise: one or more bioreactor units, wherein each of the one or more bioreactor units can comprise: a sample well filled with a three-dimensional (3D) cell growth medium, wherein the 3D cell culture medium comprises a plurality of hydrogel particles and a liquid cell culture medium, wherein the hydrogel particles are swelled with the liquid cell culture medium to form a granular gel, and a medium collection chamber fluidly connected to the sample well by a first filter material; wherein the system is configured so that application of negative gage pressure to the medium collection chamber or positive pressure to the sample well actively permeates fluid from the sample well through the three-dimensional cell growth medium, through the first filter material, and finally into the medium collection chamber; wherein the first filter material has a porosity smaller than the size of the swollen hydrogel particles.

Microscopy-enabled bioreactor systems can further comprise a liquid medium reservoir fluidly connected to the sample well by a second filter material, wherein the system can be further configured so that the application of negative gage pressure to the medium collection chamber or positive pressure to the liquid medium reservoir actively perfuses fluid from the liquid medium reservoir, through the second filter material then through the three-dimensional cell growth medium, through the first filter material, and finally into the medium collection chamber The bottom of the sample well of microscopy enabled bioreactor systems as described herein can be optically transparent. A vacuum apparatus can be operably connected to the medium collection chamber. The vacuum apparatus can be a screw-driven actuator, the screw-driven actuator can be a set actuation screw rotatably mounted within the medium collection chamber configured to actively provide negative gauge pressure to the medium collection chamber. The medium collection chamber can comprise a vacuum port fluidly connected to the medium collection chamber that is releasably connectable to a vacuum apparatus.

Microscopy enabled bioreactor systems as described herein can be configured as an array of isolated sample wells that are all fluidly connected to the same medium collection chamber. Each of the sample wells in the array are fluidly can be connected to separate liquid medium reservoirs. Each of the sample wells in the array can be fluidly connected to the same liquid medium reservoir.

Aspects of the system can have an annular arrangement comprising an outer ring, an middle ring, and a central chamber, wherein the liquid medium reservoirs is located in the outer ring, wherein the sample well is located in the middle ring, and wherein the center chamber is the medium collection chamber.

Aspects of the system can have an annular arrangement comprising an outer ring and a central chamber, wherein the sample well is located in the central chamber, wherein the medium collection chamber is located in the outer ring, and wherein the liquid medium reservoirs is located above the sample well in the central chamber.

The three-dimensional cell growth medium can have a yield stress such that the cell growth medium undergoes a phase change from a first solid phase to a second liquid phase upon application of a shear stress greater than the yield stress. The yield stress can be on the order of 10 Pa. The concentration of hydrogel particles can be between 0.05% to about 1.0% by weight. The hydrogel particles can have a size between about 0.1 µm to about 100 µm when swollen with the liquid cell culture medium.

A plurality of cells can be disposed in a region of the 3D cell culture medium.

One or more bioreactor units can be configured for a horizontal flow path of fluid from the liquid medium reservoir to the sample well to the medium collection chamber.

A microscopy-enabled bioreactor system as described herein can further comprise a pipette guide configured to receive a pipette tip and provide a fixed height from the bottom of the sample well to the distal end of the pipette tip.

One or more bioreactor units of microscopy-enabled bioreactor systems as described herein can be discrete units not in fluidic communication with one another having a horizontal flow path of fluid from liquid reservoir to sample well to medium collection chamber.

Microscopy-enable bioreactor systems as described herein can comprise a cassette configured to securely store and transport a plurality of discrete bioreactor units.

Each of the discrete units of microscopy-enable bioreactor systems as described herein can comprise three or more apertures or annular frustroconical recesses on a bottom surface configured to receive a protrusion extending toward the top of the discrete unit. Other geometric shapes can be used to provide a snug interference fit.

The cassette of microscopy-enable bioreactor systems as described herein can comprise a chamber configured to receive a plurality of bioreactor units, the chamber having a bottom surface with a plurality of recesses, each recess of the plurality configured to securely seat an individual bioreactor unit.

Each of the recesses of the bottom surface of the bioreactor units of microscopy-enable bioreactor systems as described herein can comprise three or more tapered frustroconical posts extending upwards from the bottom surface and tapering towards an end distal to the bottom surface, each of the tapered posts configured to protrude into and securely mate with the apertures or annular frustroconical recesses of the discrete bioreactor units. The cassette of microscopy-enable bioreactor systems as described herein can have a gas port. The cassette of microscopy-enable bioreactor systems as described herein can be operably connected to a heat source. A lid can be configured to securely mate with the cassette of microscopy-enable bioreactor systems as described herein. The lid can have an optical viewing window configured to allow visual inspection of the discrete bioreactor units.

Microscopy-enable bioreactor systems as described herein can comprise one or more bioreactor lids, each of the one or more bioreactor lids being configured to securely mate with a unique discrete bioreactor unit and allow gas exchange between the discrete unit and the environment. Each of lids can have an aperture configured to receive the vacuum apparatus. Each of the lids further can have an optically transparent viewing window configured to provide a user visual inspection of the sample well, the liquid medium reservoir, or both. Each of the lids can be color-coded.

Microscopy-enable bioreactor systems as described herein can further comprise an injection port for drug delivery in fluid connection with the horizontal flow path positioned in the flow path between the liquid reservoir and the sample reservoir. The injection port can be configured to receive a volume of about 1 µL to about 1 mL. The injection port can have an aperture of a diameter of about 1 mm to about 50 mm into which a drug can be injected with an injection device. The injection port can have an aperture of a diameter configured to minimize capillary action.

The first filter material and the second material of microscopy-enable bioreactor systems as described herein can be the same, and can comprise a 3D hydrogel foam configured to immobilize the 3D cell growth medium in the sample well. Other nanoporous filters may be used.

Screw-driven actuators of microscopy-enabled bioreactor systems as described herein can further comprise a pressure relief set screw operably connected to the medium collection chamber.

The media collection chamber of microscopy-enabled bioreactor systems as described herein can comprise a silicon plug providing a self-healing annular seal configured to seal the chamber from the atmosphere and receive the vacuum apparatus.

Microscopy-enabled bioreactor systems as described herein can further comprise an overflow chamber in fluidic communication with the liquid reservoir.

Microscopy-enabled bioreactor systems as described herein can further comprise a plug on a surface of the 3D culture medium of the sample well.

Microscopy-enabled bioreactor systems as described herein can further comprise a labyrinth of channels configured to receive the 3D hydrogel foam or other nanoporous filter. The labyrinth of channels can further configured to mechanically immobilize the 3D hydrogel foam within the channels.

Described herein are high-throughput bioreactor systems. High-throughput bioreactor systems as described herein can comprise a well plate, wherein the well plate comprises a plurality of apertures, each of the plurality of apertures comprising a sample well filled with a three-dimensional (3D) cell growth medium, wherein the 3D cell culture medium comprises a plurality of hydrogel particles and a liquid cell culture medium, herein the hydrogel particles are swelled with the liquid cell culture medium to form a granular gel; a filter; a center plate, the center plate comprising a plurality of apertures; and a base plate, the base plate comprising one or more medium collection chambers fluidly connected to the sample well by a filter material; wherein the bottom of the well plate is configured to mate with the top of center plate and sandwich the filter, the bottom of the center plate configured to mate with the top of the base plate, so that when mated, the sample wells of the well plate are in fluidic communication with the center plate through the filter, the center plate being in fluidic communication with the one or more medium collection chambers thereby forming a plurality of bioreactors having a vertical fluid flow path from the well plate through the filter and center plate to the base plate; wherein the system is configured so that application of negative gage pressure to the medium collection chamber actively draws fluid from the sample well where it permeates the three-dimensional cell growth medium, through the filter, and finally into the medium collection chamber; and wherein the filter material has a porosity smaller than the size of the swollen hydrogel particles.

High-throughput bioreactor systems as described herein can further comprise a vacuum apparatus operably connected to the medium collection chamber. The vacuum apparatus can comprise a screw-driven actuator, the screw-driven actuator comprising a set actuation screw rotatably operably connected to the medium collection chamber configured to actively provide negative gauge pressure to the medium collection chamber.

High-throughput bioreactor systems as described herein can comprise one or more medium collection chambers comprising a vacuum port fluidly connected to the medium collection chamber that is releasable connectable to a vacuum apparatus.

The first and second filter material of high-throughput bioreactor systems as described herein can be different.

High-throughput bioreactor systems as described herein can comprise an array of isolated sample wells that are all fluidly connected to the same medium collection chamber.

High-throughput bioreactor systems as described herein can be configured so each of the sample wells in the array are fluidly connected to separate liquid medium reservoirs. Each of the sample wells in the array can be fluidly connected to the same liquid medium reservoir.

High-throughput bioreactor systems as described herein can comprise an annular arrangement comprising an outer ring, an middle ring, and a central chamber, wherein the liquid medium reservoirs is located in the outer ring, wherein the sample well is located in the middle ring, and wherein the center chamber is the medium collection chamber.

High-throughput bioreactor systems as described herein can comprise an annular arrangement comprising an outer ring and a central chamber, wherein the sample well is located in the central chamber, wherein the medium collection chamber is located in the outer ring, and wherein the liquid medium reservoirs is located above the sample well in the central chamber.

High-throughput bioreactor systems as described herein can comprise a three-dimensional cell growth medium having a yield stress such that the cell growth medium undergoes a phase change from a first solid phase to a second liquid phase upon application of a shear stress greater than the yield stress. The yield stress can be on the order of 10 Pa. The concentration of hydrogel particles can be between 0.05% to about 1.0% by weight. The hydrogel particles can have a size between about 0.1 μm to about 100 μm when swollen with the liquid cell culture medium.

A plurality of cells (i.e. a biological sample) are disposed in a region of the 3D cell culture medium of high-throughput bioreactor systems as described herein.

The screw-driven actuator of high-throughput bioreactor systems as described herein can comprise a pressure relief set screw operably connected to the medium collection chamber.

The media collection chamber of high-throughput bioreactor systems as described herein can comprise a silicon plug having a self-healing annular seal configured to seal the chamber from the atmosphere and receive the vacuum apparatus.

The base plate of high-throughput bioreactor systems as described herein can comprise comprises a plurality of medium collection chambers, each chamber comprising a wicking post extending from a bottom surface of the chamber upwards toward the center plate being configured to collect and wick liquid away from the surface of the center plate facing the base plate and into the media collection chamber.

Each of the plurality of apertures of the center plate of high-throughput bioreactor systems as described herein can comprise a skirt on the outer diameter of the aperture extending downward towards the base plate and configured to draw liquid away from the surface of the center plate facing the base plate. The skirt can be constructed from or coated with a hydrophobic substance. The center plate can be constructed from or coated with a hydrophobic substance.

Described herein are dual-flow bioreactor systems. Dual-flow bioreactor systems as described herein can comprise a first liquid reservoir; a sample well, wherein the sample well is filled with a three-dimensional (3D) cell growth medium, wherein the 3D cell culture medium comprises a plurality of hydrogel particles and a liquid cell culture medium, wherein the hydrogel particles are swelled with the liquid cell culture medium to form a granular gel; a first medium collection chamber; a second liquid reservoir; a second medium collection chamber; a first vacuum apparatus; a second vacuum apparatus; wherein the first vacuum apparatus is operably connected to the first medium collection chamber; wherein the second vacuum apparatus is operably connected to the second medium collection chamber; wherein the first liquid reservoir is in fluidic communication with the sample well through a first filter material, which is in fluid communication with the first medium collection chamber through the first filter material, thereby forming a first perfusion flow path, wherein the first filter material has a porosity smaller than the size of the swollen hydrogel particles; wherein the second liquid reservoir is in fluidic communication with the sample well through a second filter material, which is in fluidic communication with the second medium collection chamber through the second filter media, thereby forming a second perfusion flow path, wherein the second filter material has a porosity smaller than the size of the swollen hydrogel particles; wherein the system is configured so that the first flow path and second flow path are orthogonal to one another and at different heights in the sample well from the bottom of the system; wherein the system is further configured so that application of negative gage pressure to the first medium collection chamber, second medium collection chamber, or both, actively draws fluid from the first liquid reservoir, the second liquid reservoir, or both, where it permeates the three-dimensional cell growth medium, through the first filter, the second filter, or both, and finally into the first medium collection chamber, the second collection chamber, or both.

Dual-flow bioreactor systems as described herein can further comprise a third filter material in the sample well in between the first flow path and the second flow path.

Dual-flow bioreactor systems as described herein can further comprise an optically transparent bottom below the culture chamber.

The first vacuum apparatus of dual-flow bioreactor systems as described herein can comprise a first screw-driven actuator, the first screw-driven actuator comprising a first set actuation screw rotatably mounted within the first medium collection chamber configured to actively provide negative gauge pressure to the first medium collection chamber.

The second vacuum apparatus of dual-flow bioreactor systems as described herein can comprise a second screw-driven actuator, the screw-driven actuator comprising a second set actuation screw rotatably mounted within the second medium collection chamber configured to actively provide negative gauge pressure to the second medium collection chamber.

The first medium collection chamber of dual-blow bioreactor systems as described herein can comprise a first vacuum port fluidly connected to the medium collection chamber that is releasably connectable to a vacuum apparatus, the first vacuum port formed by puncture of a first self-healing annular seal operably connected to the second medium collection chamber.

The second medium collection chamber of dual-flow bioreactor systems as described herein can comprise a second vacuum port fluidly connected to the medium collection chamber that is releasably connectable to a vacuum apparatus, the second vacuum port formed by puncture of a second self-healing annular seal operably connected to the second medium collection chamber.

The three-dimensional cell growth medium of dual-flow bioreactor systems as described herein can have a yield stress such that the cell growth medium undergoes a phase change from a first solid phase to a second liquid phase upon application of a shear stress greater than the yield stress. The yield stress can be on the order of 10 Pa. The concentration of hydrogel particles can be between 0.05% to about 1.0% by weight. The hydrogel particles can have a size between about 0.1 μm to about 100 μm when swollen with the liquid cell culture medium. A plurality of cells are disposed in a region of the 3D cell culture medium of dual-flow bioreactor systems as described herein.

The first flow path and the second flow path of dual-flow bioreactor systems as described herein can be configured for a horizontal flow path of fluid. In certain aspects, the flow paths can be orthogonal to one another but other configurations of angles other than about 90 degrees can be realized.

Dual-flow bioreactor systems as described herein can further comprise a pipette guide configured to receive a pipette tip and provide a fixed height from the bottom of the sample well to the distal end of the pipette tip.

Dual-flow bioreactor systems as described herein can further comprise a cassette configured to securely store and transport a plurality of discrete dual-flow bioreactor units, the cassette comprising a base container and a lid.

Each cassette of the dual-flow bioreactor systems can comprise three or more apertures or annular frustroconical recesses on a bottom surface configured to receive a protrusion extending toward the top of the discrete unit.

The base container of the cassette of the dual-flow bioreactor system can comprise a chamber configured to receive a plurality of dual-flow bioreactor units, the chamber having a bottom surface with a plurality of recesses, each recess of the plurality configured to securely seat an individual bioreactor unit.

Each of the recesses of the bottom surface of the cassettes of the dual-flow bioreactor system can comprise three or more tapered frustroconical posts extending upwards from the bottom surface and tapering towards an end distal to the bottom surface, each of the tapered posts configured to protrude into and securely mate with the apertures or annular frustroconical recesses of the discrete bioreactor units.

Each cassette of dual-flow bioreactor systems as described herein can further comprise a gas port. The cassette of dual-flow bioreactor systems as described herein can operably connected to a heat source. The lid of the cassette can have an optical viewing window configured to allow visual inspection of the discrete bioreactor units.

Dual-flow bioreactor systems as described herein can comprise a one or more bioreactor lids, each of the one or more bioreactor lids being configured to securely mate with a unique discrete bioreactor unit and allow gas exchange between the discrete unit and the environment. Each of lids comprises an aperture configured to receive the vacuum apparatus. Each of the lids further comprises an optically transparent viewing window configured to provide a user visual inspection of the sample well, the liquid medium reservoir, or both. Each of the lids can be color-coded.

Dual-flow bioreactor systems as described herein can comprise a first injection port for drug delivery in fluid connection with the first flow path positioned in the first flow path between the first liquid reservoir and the sample well. The first injection port can be configured to receive a volume of about 1 µL to about 1 mL. The first injection port can have an aperture of a diameter of about 1 mm to 50 mm into which a drug can be injected with an injection device.

The first injection port can have an aperture of a diameter configured to minimize capillary action.

Dual-flow bioreactor systems as described herein can further comprise a second injection port for drug delivery in fluid connection with the second flow path positioned in the second flow path between the second liquid reservoir and the sample well. The second injection port can be configured to receive a volume of about 1 µL to about 1 mL. The second injection port can have an aperture of a diameter of about 1 mm to 50 mm into which a drug can be injected with an injection device. The second injection port can have an aperture of a diameter configured to minimize capillary action.

The first filter material and the second filter material of dual-flow bioreactor systems as described herein can be the same, and comprise a 3D hydrogel foam configured to immobilize the 3D cell growth medium in the sample well. Other nanoporous filter materials may be used.

The first screw-driven actuator of dual-flow bioreactor systems as described herein can further comprise a pressure relief set screw operably connected to the first medium collection chamber.

The second screw-driven actuator of dual-flow bioreactor systems as described herein can further comprises a pressure relief set screw operably connected to the second medium collection chamber.

The first medium collection chamber of dual-flow bioreactor systems as described herein can comprise a first silicon plug providing a self-healing annular seal configured to seal the chamber from the atmosphere and receive the vacuum apparatus.

The second medium collection chamber of dual-flow bioreactor systems as described herein can comprise a second silicon plug providing a self-healing annular seal configured to seal the chamber from the atmosphere and receive the vacuum apparatus.

Dual-flow bioreactor systems as described herein can further comprise a first overflow chamber in fluidic communication with the first liquid reservoir.

Dual-flow bioreactor systems as described herein can further comprise a second overflow chamber in fluidic communication with the second liquid reservoir.

Dual-flow bioreactor systems as described herein can further comprise a plug on a surface of the 3D culture medium of the sample well.

Dual-flow bioreactor systems as described herein can further comprise a labyrinth of channels in the first flow path, second flow path, or both configured to receive the 3D hydrogel foam. The labyrinth of channels is further configured to mechanically immobilize the 3D hydrogel foam within the channels.

Described herein are methods of using perfusion-enabled bioreactor systems as described herein. A method of using a perfusion-enabled bioreactor, can comprise providing a bioreactor system as described herein; providing a biological sample; providing a 3D growth media; placing the 3D growth media in a culture chamber of the bioreactor; pipetting the biological sample into the 3D growth media; applying a positive or negative gage pressure to the bioreactor thereby drawing fluid into the 3D growth media through active perfusion. Methods as described herein can further comprise applying a composition into the injection port of the bioreactor after applying the positive or negative gage pressure.

Described herein are kits. Kits as described herein can comprise one or more bioreactors as described herein. Kits as described herein can further comprise a 3D grow media. Kits as described herein can further comprise one or more pipette guides.

Kits as described herein can further comprise a vacuum apparatus and/or a pressure gauge. The pressure gauge can be operably connected and in fluid communication with the vacuum apparatus. Kits as described herein can further comprise a cassette configured to receive and securely hold the one or more bioreactors.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10 displays an embodiment of a mechanical pipetting guide for use with bioreactor systems as disclosed herein for the purpose of precise and repeatable placement of features within bioreactor systems as described herein.

FIG. 19A is a top view, FIG. 19B a cross-sectional side view, and FIG. 19C a bottom view.

FIG. 21 is a cross-sectional view of the culture chamber (LLS chamber) of the embodiment of the aspect of the bioreactor system having dual flow paths.

FIGS. 23A-23D is an embodiment of an aspect of bioreactor systems as described herein having dual flow paths. FIG. 23A shows a perspective view, FIG. 23B a top view; FIG. 23C a side view; and FIG. 23D a bottom view.

FIGS. 24A-24C is another illustration of the embodiment of FIGS. 23A-23D. A top view is shown in FIG. 24A, and cross-sectional side views are shown in FIGS. 24B and 24C.

FIG. 26 is a photograph of an embodiment 2000 of an array of perfusion-enabled bioreactors configured in a multi-well high throughput setup.

FIGS. 29A-29B. FIG. 29A is a cross-sectional perspective view of the embodiment 2000 of FIG. 26 showing a vacuum source apparatus inserted in a self-healing annular seal of a well of the plate. FIG. 29B is an enlarged view of 29A.

DETAILED DESCRIPTION

Figure 1:
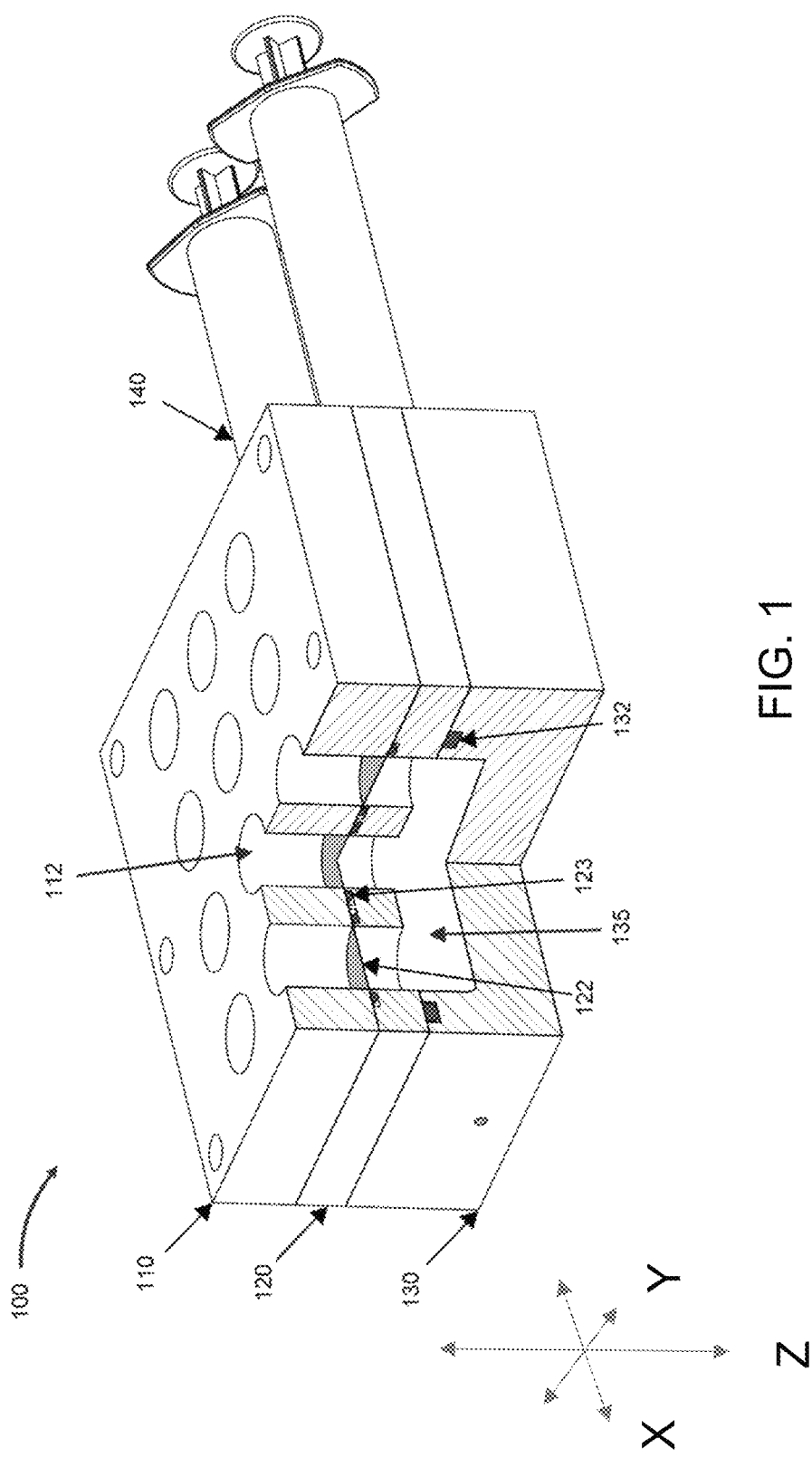
FIG. 1 is a perspective view of embodiment of a bioreactor system according to the present view, with a cutout showing aspects of the internal environment.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

To combat stagnant toxic environment in 3D culture, a perfusive flow can be induced through the support medium, thereby flowing in nutrient solution and flowing out waste products. Disclosed herein are systems and methods that provide for such. The disclosed systems and methods can vastly improve upon the current standard by introducing a specialized jammed microgel system that allows for cellular migration and perfusion and is experiment ready as soon as the cells are placed within it. The device that houses this gel includes a filter and a vacuum system which allows the nutrient media to perfuse through the system without disturbing the cellular environment. Since the perfusion relies on a vacuum, pulsatile flow, which can affect cell behavior, can easily be achieved. Such pulsatile flow can be active pulsatile flow. Furthermore, this system can allow for continuous optical access during the growth of the biological samples.

Disclosed herein is a bioreactor system that can involve a single-well, multi-well, or continuous-well platform with optional integrated optical pathways for direct observation of biological samples in bioreactor units. Such single-well platforms can be discrete units housed in a cassette, and multi-well platforms can be analogous to multi-well plates. Perfusive flow is used through a unique porous support medium in the bioreactor enabling 3D growth of biological samples. Optical pathways enable microscopy of biological samples without interruption of perfusion, and allows long-term growth and behavior to be studied without disturbing the environment.

Perfusion-enabled bioreactor systems as described herein allow for 3D tissue culture of biological samples in a 3D growth media, also referred to herein as a liquid-like solid or LLS.

Bioreactor systems as described herein can comprise a pressure generating means, a feed media source, a culture chamber with 3D growth media (also referred to herein as a liquid-like solid or LLS), a filter, and a media collection chamber (also referred to herein as an effluent chamber, effluent collection chamber, analyte chamber, analyte collection chamber, waste chamber, or waste collection chamber). In certain embodiments according to the present disclosure, the feed media source is media in the culture chamber, whereas in other embodiments, it is a physically separate liquid reservoir that is a distinct structure component from the culture chamber. Bioreactor systems as described herein can also comprise drug delivery ports for the study of application of precise and efficient delivery of drugs (small molecules, proteins, nucleic acids, sugars, and the like) to cells of interest.

Application of positive or negative pressure from the pressure generating means drives the perfusion of fluid from the feed media source to the 3D growth media, through the filter, and into the media collection chamber. In certain aspects systems as described herein are configured for a horizontal fluid perfusion path to allow for microscopy-enabled systems, in other aspects, the system is configured for a vertical fluid perfusion path for high throughput-enabled systems.

The filter can be a 3D hydrogel material, or other filters.

Bioreactor systems as described herein can be constructed of a single piece of material, for example by milling, or can be constructed of multiple pieces fastening or otherwise glued together.

Culture chambers as described herein are configured to hold a volume of 3D growth media in which biological samples can be cultured.

Filter Material

The disclosed bioreactor systems comprise one or more filters that allows the liquid media to perfuse through the system without disturbing the cellular environment.

The filter material can be any combination of biocompatible, or inert, materials which can form a solid and retain a porosity equal to or smaller than the size of the 3D support matrix polymer. Prime examples include pHEMA polymerized to a degree to which spinodal decomposition occurs, producing a porosity on the order of the 3D support matrix polymer; sintered microparticles including polyether ether ketone (PEEK), borosilicate, steel, or various ceramics.

In designs such as that in FIG. 1, filter material may be composed of nanoporous sheet membranes of material polycarbonate, nylon, or various other materials which produce the same effect while remaining biocompatible or inert.

In certain embodiments, such as those described herein and shown in FIGS. 4-7 and 10-25, the filter material can be a 3D hydrogel. The 3D hydrogel is a cross-linked hydrogel foam. It acts as a filter to prevent LLS from moving through it but allows liquid such as growth media to flow through. It is not a "liquid-like solid." It has a relatively large pore size in comparison to the LLS, approximately 10 um but can be in the range of 5 um-20 um. It is much more structural than the LLS and does not behave like a liquid. It can be made out of various substances, such as acrylamide or polyhydroxyethylmethacrylate. The 3D hydrogel can be configured so that it holds and immobilizes 3D growth media as further described herein, thereby preventing disturbance or perturbation of the growth media by the application of a vacuum or positive pressure.

The filter material can have a porosity that is smaller than components of the 3D growth media, which is described in detail below.

Vacuum Source

The disclosed bioreactor systems can use any source of positive or negative gage pressure to draw fluid through the system. Such pressure can be created by a vacuum source, also referred to herein as a pressure generating device or apparatus. In some cases, a vacuum is applied. Negative and positive pressure can be created using various known means. In some cases, the pressure is generated using mechanical means, including but not limited to a peristaltic pump, syringe, piston, or screw. Passive systems for generating pressure are also known, and include osmotic gradients and capillary forces. For example, an osmotic gradient can be generated by placing unswollen polymer powder in the collection chamber.

In embodiments of the present disclosure, the vacuum source is a screw-driven actuator configured so that turns of the screw provide negative pressure or positive pressure to the system, depending on how the screw is turned.

In embodiments of the present disclosure, the vacuum source is operatively coupled to the system by the puncture of a self-healing annular seal by a device such as a needle, which is a part of and operatively connected to a device that provides a vacuum, such as those as described above. Such embodiments can optionally include pressure gauges for monitoring the pressure in the system so as to inform a user of the pressure.

Vacuum sources as described herein can be releasably connected to the system, through connections such as Luer locks and self-healing annular seals. Examples of self-healing annular seals as described herein include rubber stoppers such as those used in blood collection tubes which are ubiquitous in the medical professions.

3D Medium

Liquid-like solid (LLS) three-dimensional (3D) cell growth medium (also referred to herein as "liquid-like solid", "LLS", "3D growth medium", or "3D cell growth medium") for use in with the disclosed bioreactor system is disclosed in WO2016182969A1 by Sawyer et al., which is incorporated by reference in its entirety for the description of how to make and uses this LLS medium.

Liquid-like solids (LLS) have properties that provide a combination of transport, elastic, and yielding properties, which can be leveraged to design a support material for the maintenance of living cells in three-dimensional culture. These materials may be composed predominantly of solvent that freely diffuses and can occupy more than 99% of their volume, but they also have a finite modulus and extremely low yield-stress in their solid state. Upon yielding, these materials shear and behave like classical fluids. Packed granular microgels are a class of liquid-like solids that have recently been adopted as a robust medium for precise three dimensional fabrication of delicate materials. The unrestricted diffusion of nutrients, small molecules, and proteins can support the metabolic needs of cells and provide an easy route to the development of combinatorial screening methods. Unperturbed, LLS materials can provide support and stability to cells and to cell-assemblies, and facilitate the development and maintenance of precise multi-cellular structures.

Briefly, the 3D cell growth medium may comprise hydrogel particles dispersed in a liquid cell growth medium. Any suitable liquid cell growth medium may be used; a particular liquid cell growth medium may be chosen depending on the types of cells which are to be placed within the 3D cell growth medium, as one of skill in the art would understand. For example, suitable cell growth medium may be human cell growth medium, murine cell growth medium, bovine cell growth medium or any other suitable cell growth medium. Depending on the particular embodiment, hydrogel particles and liquid cell growth medium may be combined in any suitable combination. For example, in some embodiments, a 3D cell growth medium comprises approximately 0.5% to 1% hydrogel particles by weight. In some embodiments, the hydrogel particles can have a size in the range of about 0.1 μm to about 100 μm when swollen with the liquid cell culture medium. In some embodiments, the hydrogel particles can have a size in the range of about 1 μm to about 10 μm when swollen with the liquid cell culture medium.

In accordance with some embodiments, the hydrogel particles may be made from a bio-compatible polymer.

The hydrogel particles may swell with the liquid growth medium to form a granular gel material. Depending on the particular embodiment, the swollen hydrogel particles may have a characteristic size at the micron or submicron scales. For example, in some embodiments, the swollen hydrogel particles may have a size between about 0.1 μm and 100 μm. Furthermore, a 3D cell growth medium may have any suitable combination of mechanical properties, and in some embodiments, the mechanical properties may be tuned via the relative concentration of hydrogel particles and liquid cell growth medium. For example, a higher concentration of hydrogel particles may result in a 3D growth medium having a higher elastic modulus and/or a higher yield stress.

According to some embodiments, the 3D cell growth medium may be made from materials such that the granular gel material undergoes a temporary phase change due to an applied stress (e.g. a thixotropic or "yield stress" material). Such materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Stress may be applied to such materials in any suitable way. For example, energy may be added to such materials to create a phase change. The energy may be in any suitable form, including mechanical, electrical, radiant, or photonic, etc.

Regardless of how cells are placed in the medium, the yield stress of the yield stress material may be large enough to prevent yielding due to gravitational and/or diffusional forces exerted by the cells such that the position of the cells within the 3D growth medium may remain substantially constant over time. As described in more detail below, placement and/or retrieval of groups of cells may be done manually or automatically.

A yield stress material as described herein may have any suitable mechanical properties. For example, in some embodiments, a yield stress material may have an elastic modulus between approximately 1 Pa and 1000 Pa when in a solid phase or other phase in which the material retains its shape under applied stresses at levels below the yield stress. In some embodiments, the yield stress required to transform a yield stress material to a fluid-like phase may be between approximately 1 Pa and 1000 Pa. In some embodiments, the yield stress may be on the order of 10 Pa, such as 10 Pa+/−25%. When transformed to a fluid-like phase, a yield stress material may have a viscosity between approximately 1 Pa s and 10,000 Pa s. However, it should be understood that other values for the elastic modulus, yield stress, and/or viscosity of a yield stress material are also possible, as the present disclosure is not so limited.

A group of cells may be placed in a 3D growth medium made from a yield stress material via any suitable method. For example, in some embodiments, cells may be injected or otherwise placed at a particular location within the 3D growth medium with a syringe, pipette, or other suitable placement or injection device, such as automated liquid handler. In some embodiments an array of automated cell dispensers may be used to inject multiple cell samples into a container of 3-D growth medium. Movement of the tip of a placement device through the 3D growth medium may impart a sufficient amount of energy into a region around the tip to cause yielding such that the placement tool may be easily moved to any location within the 3D growth medium. In some instances, a pressure applied by a placement tool to deposit a group of cells within the 3D growth medium may also be sufficient to cause yielding such that the 3D growth medium flows to accommodate the group of cells. Movement of a placement tool may be performed manually (e.g. "by hand"), or may performed by a machine or any other suitable mechanism.

In some embodiments, multiple independent groups of cells may be placed within a single volume of a 3D cell growth medium. For example, a volume of 3D cell growth medium may be large enough to accommodate at least 2, at least 5, at least 10, at least 20, at least 50, at least 100, at least 1000, or any other suitable number of independent groups of cells. Alternatively, a volume of 3D cell growth medium may only have one group of cells. Furthermore, it should be understood that a group of cells may comprise any suitable number of cells, and that the cells may of one or more different types.

Depending on the particular embodiment, groups of cells may be placed within a 3D cell growth medium according to any suitable shape, geometry, and/or pattern. For example, independent groups of cells may be deposited as spheroids, and the spheroids may be arranged on a 3D grid, or any other suitable 3D pattern. The independent spheroids may all comprise approximately the same number of cells and be approximately the same size, or alternatively different spheroids may have different numbers of cells and different sizes. In some embodiments, cells may be arranged in shapes such as embryoid or organoid bodies, tubes, cylinders, toroids, hierarchically branched vessel networks, high aspect ratio objects, thin closed shells, or other complex shapes which may correspond to geometries of tissues, vessels or other biological structures.

According to some embodiments, a 3D cell growth medium made from a yield stress material may enable 3D printing of cells to form a desired pattern in three dimensions. For example, a computer-controlled injector tip may trace out a spatial path within a 3D cell growth medium and inject cells at locations along the path to form a desired 3D pattern or shape. Movement of the injector tip through the 3D cell growth medium may impart sufficient mechanical energy to cause yielding in a region around the injector tip to allow the injector tip to easily move through the 3D cell growth medium, and also to accommodate injection of cells. After injection, the 3D cell growth medium may transform back into a solid-like phase to support the printed cells and maintain the printed geometry. However, it should be understood that 3D printing techniques are not required to use a 3D growth medium as described herein.

According to some embodiments, a 3D cell growth medium may be prepared by dispersing hydrogel particles in a liquid cell growth medium. The hydrogel particles may be mixed with the liquid cell growth medium using a centrifugal mixer, a shaker, or any other suitable mixing device. During mixing, the hydrogel particles may swell with the liquid cell growth medium to form a material which is substantially solid when an applied shear stress is below a yield stress, as discussed above. After mixing, entrained air or gas bubbles introduced during the mixing process may be removed via centrifugation, agitation, or any other suitable method to remove bubbles from 3D cell growth medium.

In some embodiments, preparation of a 3D cell growth medium may also involve buffering to adjust the pH of a hydrogel particle and liquid cell growth medium mixture to a desired value. For example, some hydrogel particles may be made from polymers having a predominantly negative charge which may cause a cell growth medium to be overly acidic (have a pH which is below a desired value). The pH of the cell growth medium may be adjusted by adding a strong base to neutralize the acid and raise the pH to reach the desired value. Alternatively, a mixture may have a pH that is higher than a desired value; the pH of such a mixture may be lowered by adding a strong acid. According to some embodiments, the desired pH value may be in the range of about 7.0 to 7.4, or, in some embodiments 7.2 to 7.6, or any other suitable pH value which may, or may not, correspond to in vivo conditions. The pH value, for example may be approximately 7.4. In some embodiments, the pH may be adjusted once the dissolved $CO_2$ levels are adjusted to a desired value, such as approximately 5%.

Yield stress can be measured by performing a strain rate sweep in which the stress is measured at many constant strain rates. Yield stress can be determined by fitting these data to a classic Herschel-Bulkley model ($\sigma=\sigma_y+k\dot{\gamma}^n$). (b) To determine the elastic and viscous moduli of non-yielded LLS media, frequency sweeps at 1% strain can be performed. The elastic and viscous moduli remain flat and separated over a wide range of frequency, behaving like a Kelvin-Voigt linear solid with damping. Together, these rheological properties demonstrate that a smooth transition between solid and liquid phases occurs with granular microgels, facilitating their use as a 3D support matrix for cell printing, culturing, and assaying.

An example of a hydrogel with which some embodiments may operate is a carbomer polymer, such as Carbopol®. Carbomer polymers may be polyelectrolytic, and may comprise deformable microgel particles. Carbomer polymers are particulate, high-molecular-weight crosslinked polymers of acrylic acid with molecular weights of up to 3-4 billion Daltons. Carbomer polymers may also comprise co-polymers of acrylic acid and other aqueous monomers and polymers such as poly-ethylene-glycol.

While acrylic acid is a common primary monomer used to form polyacrylic acid the term is not limited thereto but includes generally all α-β unsaturated monomers with carboxylic pendant groups or anhydrides of dicarboxylic acids and processing aids as described in U.S. Pat. No. 5,349,030. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be cross-linked with polyfunctional materials as divinyl benzene, unsaturated diesters and the like, as is disclosed in U.S. Pat. Nos. 2,340,110; 2,340,111; and 2,533,635. The disclosures of all of these U.S. patents are hereby incorporated herein by reference for their discussion of carboxylic polymers and copolymers that, when used in polyacrylic acids, form yield stress materials as otherwise disclosed herein. Specific types of cross-linked polyacrylic acids include carbomer homopolymer, carbomer copolymer and carbomer interpolymer monographs in the U.S. Pharmocopia 23 NR 18, and Carbomer and C10-30 alkylacrylate crosspolymer, acrylates crosspolymers as described in PCPC International Cosmetic Ingredient Dictionary & Handbook, 12th Edition (2008).

Carbomer polymer dispersions are acidic with a pH of approximately 3. When neutralized to a pH of 6-10, the particles swell dramatically. The addition of salts to swelled Carbomer can reduce the particle size and strongly influence their rheological properties. Swelled Carbomers are nearly refractive index matched to solvents like water and ethanol, making them optically clear. The original synthetic powdered Carbomer was trademarked as Carbopol® and commercialized in 1958 by BF Goodrich (now known as Lubrizol), though Carbomers are commercially available in a multitude of different formulations.

Hydrogels may include packed microgels—microscopic gel particles, ~5 μm in diameter, made from crosslinked polymer. The yield stress of Carbopol® is controlled by water content. Carbopol® yield stress can be varied between roughly 1-1000 Pa. Thus, both materials can be tuned to span the stress levels that cells typically generate. As discussed above, while materials may have yield stresses in a range of 1-1000 Pa, in some embodiments it may be advantageous to use yield stress materials having yield stresses in a range of 1-100 Pa or 10-100 Pa. In addition, some such materials may have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

In one non-limiting example, a 3D cell growth medium comprises approximately 0.2% to about 0.7% by mass Carbopol® particles (Lubrizol). The Carbopol® particles are mixed with and swell with any suitable liquid cell growth medium, as described above, to form a 3D cell growth medium which comprises approximately 99.3% to about 99.8% by mass cell growth medium. After swelling, the particles have a characteristic size of about 1 μm to about 10 μm. The pH of the mixture is adjusted to a value of about 7.4 by adding a strong base, such as NaOH. The resulting 3D cell growth medium is a solid with a modulus of approximately 100-300 Pa, and a yield stress of approximately 20 Pa. When a stress is applied to this 3D cell growth medium which exceeds this yield stress, the cell growth medium transforms to a liquid-like phase with a viscosity of approximately 1 Pa s to about 1000 Pa s. As described above, the specific mechanical properties may be adjusted or tuned by varying the concentration of Carbopol®. For example, 3D cell growth media with higher concentrations of Carbopol® may be stiffer and/or have a larger yield stress.

In an embodiment, a LLS can be prepared with 0.9% (w/v) Carbopol® ETD 2020 polymer (Lubrizol Co.) was dispersed in cell growth media under sterile conditions. The pH of the medium is adjusted by adding NaOH until pH 7.4 is reached under the incubation condition of 37° C. and 5% C02, and the completely formulated material is homogenized in a high-speed centrifugal mixer. Carbopol® ETD 2020 swells maximally at this pH, making it suitable for cell culture applications. The gel medium was incubated at 37° C. and 5% C02.

The hydrogels for the LLS may be dispersed in solutions (e.g., solutions with cell growth medium) in various concentrations to form the LLS. One example of a concentration is below 2% by weight. Another concentration example is approximately 0.5% to 1% hydrogel particles by weight, and another is approximately 0.2% to about 0.7% by mass.

Hydrogels may include packed microgels—microscopic gel particles, ~5 μL in diameter, made from crosslinked polymer. The yield stress of Carbopol® is controlled by water content. Carbopol® yield stress can be varied between roughly 1-1000 Pa. Thus, both materials can be tuned to span the stress levels that cells typically generate. As discussed above, while materials may have yield stresses in a range of 1-1000 Pa, in some embodiments it may be advantageous to use yield stress materials having yield stresses in a range of 1-100 Pa or 10-100 Pa. In addition, some such materials may have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

Those skilled in the art will appreciate that materials having a yield stress will have certain thixotropic properties, such as a thixotropic time and a thixotropic index. As used herein, a thixotropic time is a time for shear stress to plateau following removal of a source of shear. The inventors recognize that thixotropic time may be measured in different ways. As used herein, unless indicated otherwise, thixotropic time is determined by applying to a material, for several seconds, a stress equal to 10 times the yield stress of the material, followed by dropping the stress to 0.1 times the yield stress. The amount of time for the shear rate to plateau following dropping of the stress is the thixotropic time.

As used herein, a thixotropic index (for a yield stress material) is defined as the ratio of viscosity at a strain-rate of 2 $s^1$ to viscosity at a strain-rate of 20 $s^1$.

Yield stress materials with desirable yield stresses may also have desirable thixotropic properties, such as desirable thixotropic indexes or thixotropic times. For example, desirable yield stress materials (including hydrogel materials having a yield stress below 100 Pascals, some of which are described in detail below, such as Carbopol® materials) may have thixotropic times less than 2.5 seconds, less than 1.5 seconds, less than 1 second, or less than 0.5 seconds, and greater than 0.25 seconds or greater than 0.1 seconds. An exemplary Carbopol® solution may exhibit a yield stress below 100 Pascals (and below 25 Pascals in some embodiments), as well as low thixotropic times. The thixotropic times of the Carbopol® solutions having a yield stress below 100 Pascals may be less than 2.5 seconds, less than 1.5 seconds, less than 1 second, or less than 0.5 seconds, and greater than 0.25 seconds or greater than 0.1 seconds.

In some embodiments, for hydrogel yield stress materials with a yield stress below 100 Pascals (including those discussed in detail below, like Carbopol® solutions), the thixotropic index is less than 7, less than 6.5, or less than 5, and greater than 4, or greater than 2, or greater than 1.

Desirable yield stress materials, like hydrogels such as the Carbopol® solutions described herein, may thus have thixotropic times less than 2.5, less than 1.5 seconds, less than 1 second, or less than 0.5 seconds, and greater than 0.25 seconds or greater than 0.1 seconds, and/or thixotropic indexes less than 7, less than 6.5, or less than 5, and greater than 4, or greater than 2, or greater than 1.

Because of the yield stress behavior of yield stress materials, materials deposited into a yield stress material (such as through 3D printing techniques described herein) may remain fixed in place in the yield stress material, without the yield stress material or the deposited material needing to be cured or otherwise treated to reverse a phase change (e.g., by heating to cross-link, following printing). Rather, the yield stress materials permit an indefinite working time on deposition of materials inside yield stress materials, including printing of cell clusters within yield stress materials.

In another non-limiting embodiment, a method for preparing a 3D cell growth medium is described. The method begins when hydrogel particles are mixed with a liquid cell culture medium. Mixing may be performed with a mechanical mixer, such as a centrifugal mixer, a shaker, or any other suitable mixing device to aid in dispersing the hydrogel particles in the liquid cell culture medium. During mixing, the hydrogel particles may swell with the liquid cell culture medium to form a granular gel, as discussed above. In some instances, the mixing act may result in the introduction of air bubbles or other gas bubbles which may become entrained in the gel. Such entrained gas bubbles are removed at via centrifugation, gentle agitation, or any other suitable technique. The pH of the mixture may then be adjusted; a base may be added to raise the pH, or alternatively an acid may be added to lower the pH, such until the pH of the mixture reaches a desired value. In some embodiments, the final pH value after adjustment is about 7.4.

System

Turning now to the figures, specific non-limiting embodiments of bioreactor system are described in more detail.

FIG. 1, FIG. 2A, FIG. 2B, and FIG. 2C depict a first embodiment of a bioreactor system 100 that comprises a plurality of sample wells for culturing cells (such as tumor samples) in a 3D cell growth medium, which allows the nutrient media to actively perfuse through the system without disturbing the cellular environment. The perfusion can also be used to create pulsatile flow, which can affect cell behavior.

The wells of the embodiment of the bioreactor system 100 are preferably arrayed in columns and rows as depicted in FIG. 1 and FIG. 2A-2C. The depicted embodiment of the bioreactor system 100 uses a syringe 140 to create a vacuum to draw media from the sample wells 112 through a filter material 122 and into a media collection chamber 135. In this embodiment, the media travels with gravity in a vertical direction, and the active perfusive flow is vertical flow. As best appreciated in the exploded views of FIGS. 2A to 2C, the depicted embodiment of the bioreactor system 100 is assembled from three horizontal plates, a well plate 110, a center plate 120, and a base plate 130.

Figure 2A:
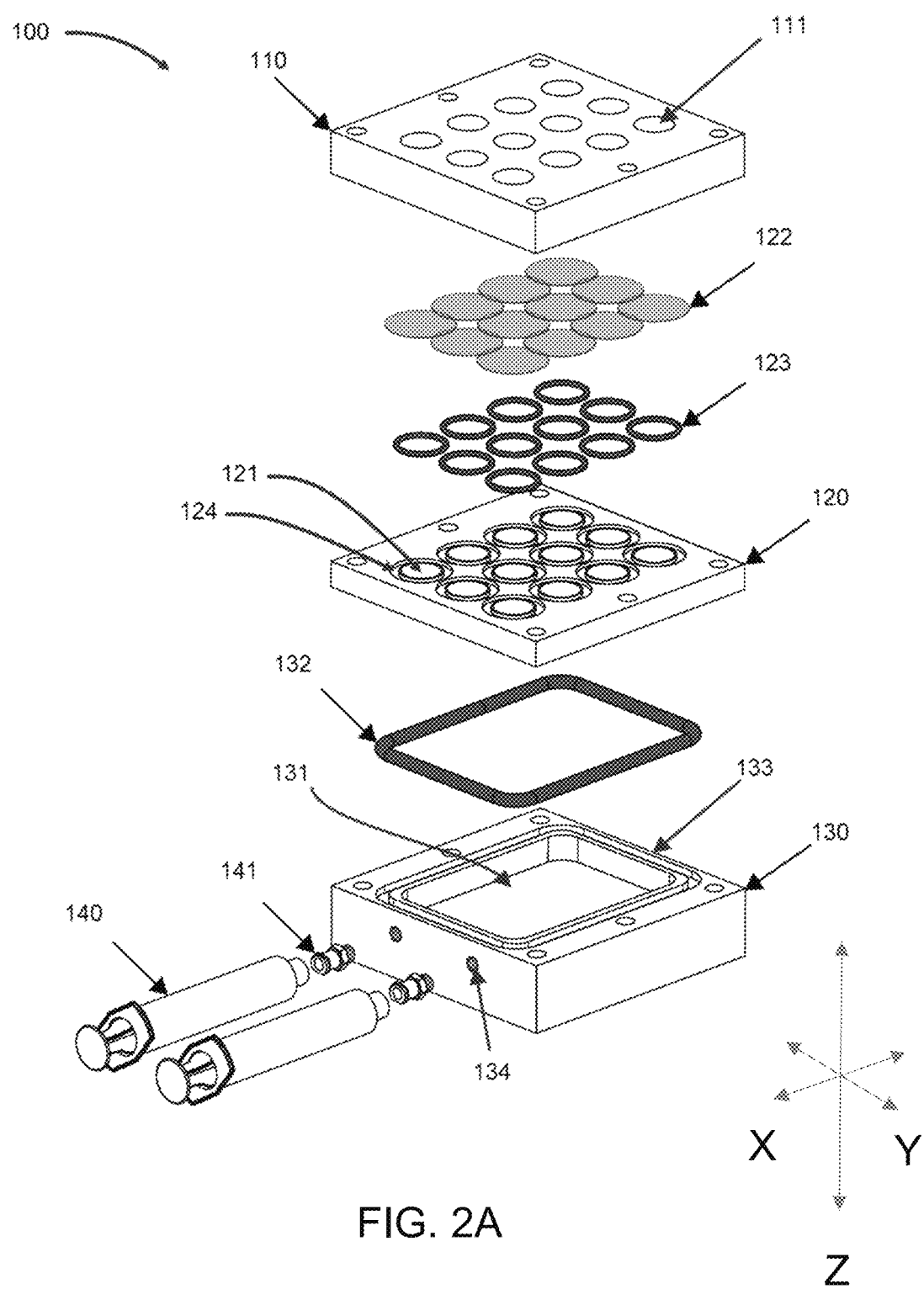
FIG. 2A-2C are exploded views of bioreactor systems as described herein.
Figure 2B:
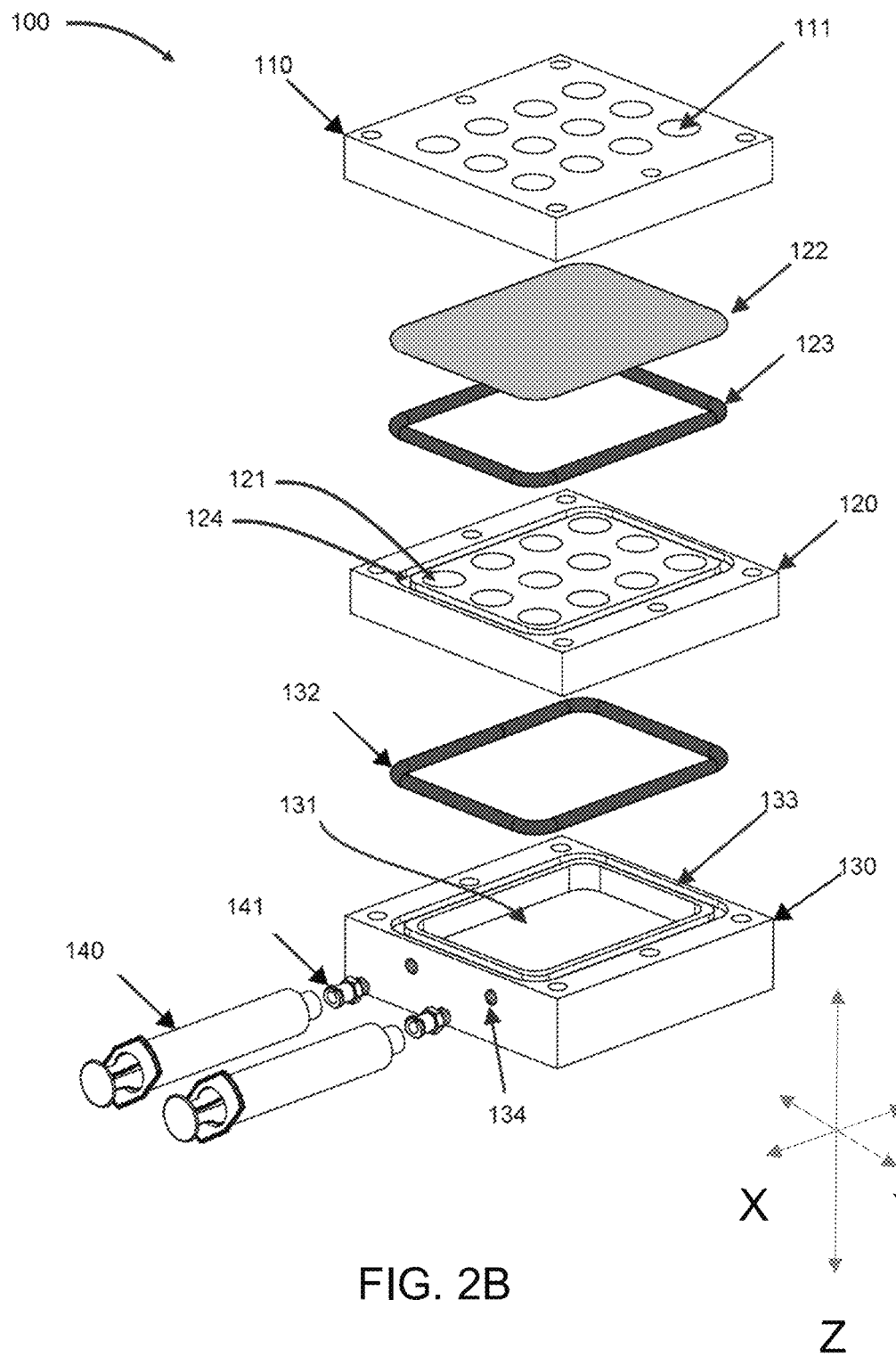
Figure 2C:
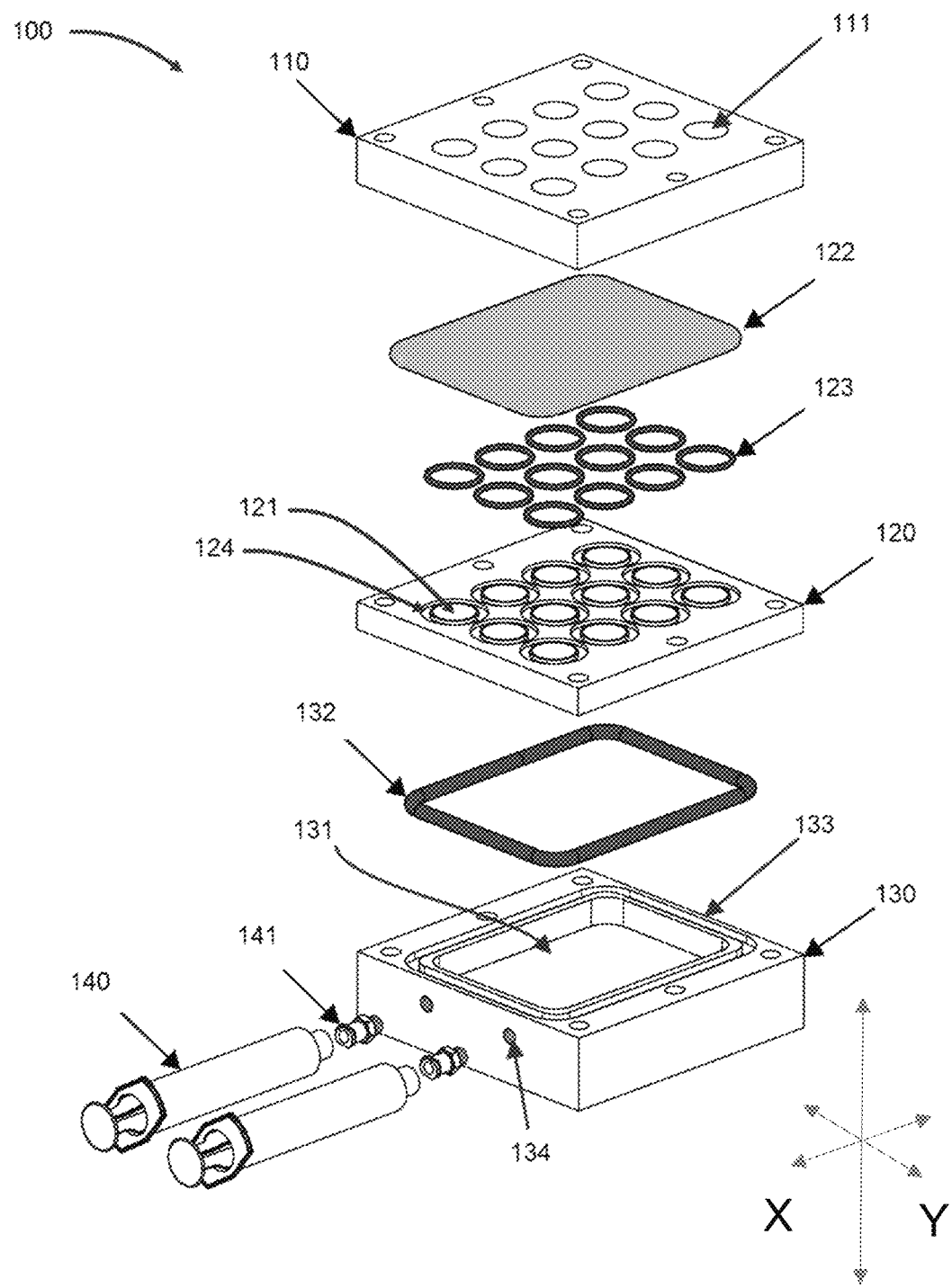

The depicted well plate 110 is a planar material having a top surface, a bottom surface, and a thickness corresponding to the desired well height. The sample wells 112 are defined by orifices 111 extending from the top surface to the bottom surface of the well plate 110 and a filter material 122 positioned below the well plate 110. The bottom of each well 112 is therefore defined by the filter material 122 compressed between the well plate 110 and the center plate 120. In some cases, as shown in FIG. 2A, there are a plurality of filters 122, such as one for each well 112. In some cases, as shown in FIGS. 2B and 2C, there is a single filter material 122 acting as the bottom for all of the wells 112. Optionally, the wells of the well plate can be tapered so that the diameter of the top of the well is different than the diameter of the bottom of the well. In certain aspects, the diameter of the top of the well can be larger than the diameter of the bottom of the well. The planar material can be an inert material. The planar material can be delrin and/or peek. This component can also be injection molded using materials such as polystyrene. The planar material is a material that exhibits low liquid absorption and low thermal expansion.

The depicted center plate 120 can comprise a plurality of apertures 121 configured to align with the orifices 111 when the plates are stacked together, mated, abutted, or otherwise operably assembled. In order to provide a seal, one or more gaskets 123 can be positioned between the center plate 120 and the filter material 122. Therefore, the center plate 120 can contain one or more grooves 124 for seating the one or more gaskets 123. As shown in FIGS. 2A and 2C, these grooves 124 can be positioned around the perimeter of each aperture 121, or, as depicted in FIG. 2B, these grooves 124 can be posited around the perimeter of the array of apertures 121 when a single filter material 122 is used. As will be appreciated by one of skill in the art, the grooves 124 and filter material 122 should be sized and positioned to provide a seal when the gasket 123 is seated in the groove 124. The seal that is formed can be a seal suitable for the creation of a vacuum. The center plate can be made of a hydrophobic material. This can aid in droplet formation on the bottom of the filter and the skirt (if present), as well as force the droplet down into the hydrophilic base. The center plate can be made of polytetrafluoroethylene (PTFE). This component can also be injection molded.

The depicted base plate 130 is a planar material having a top surface, a bottom surface, and a thickness, that has a cavity 131 in its top surface that defines a media collection chamber 135 below the center plate 120 when the plates are stacked together. The cavity 131 is sized to be in fluid communication with all of the orifices 111 and apertures 121 when the plates are stacked. In order to provide a seal, a second gasket 132 can be positioned between the base plate 130 and the center plate 120. Therefore, the base plate 130 can contain a trench 133 for seating the second gasket 132 positioned around the perimeter of the cavity 131. The base plate can be hydrophilic to preferentially draw the effluent from the intermediate plate into the effluent collection chamber. The material can be polyether ether ketone (PEEK), and delrin can also be used. This component can also be injection molded.

The bioreactor system 100 functions by creating a vacuum in the media collection chamber 135, which creates a negative pressure that draws media from the wells 112, through the filter material 122, and into the media collection chamber 135. Therefore, as shown in FIGS. 1, 2A, 2B, and 2C, one or more vacuum sources, such as syringes 140, can be attached or releasably attached to the base plate 130 at one or more openings 134 that are in fluid communication with the cavity 131. Connectors 141, such as Luer lock connectors, can be used to facilitate this attachment.

Figure 3:
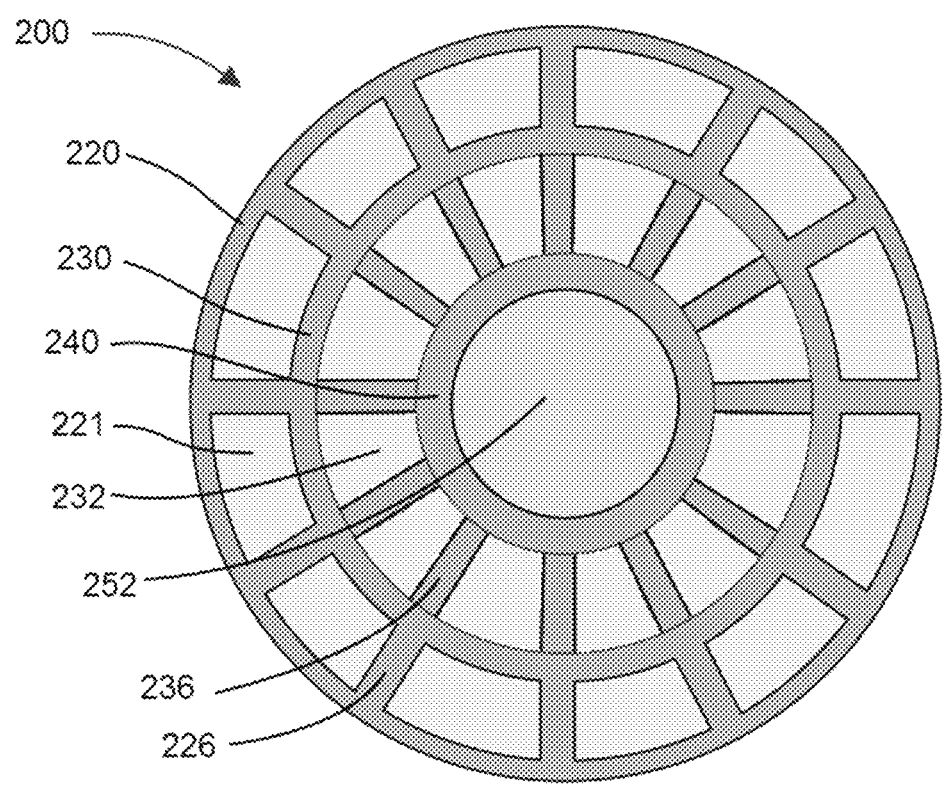
FIG. 3 is a top view of one embodiment of a bioreactor system disclosed herein.
Figure 4:
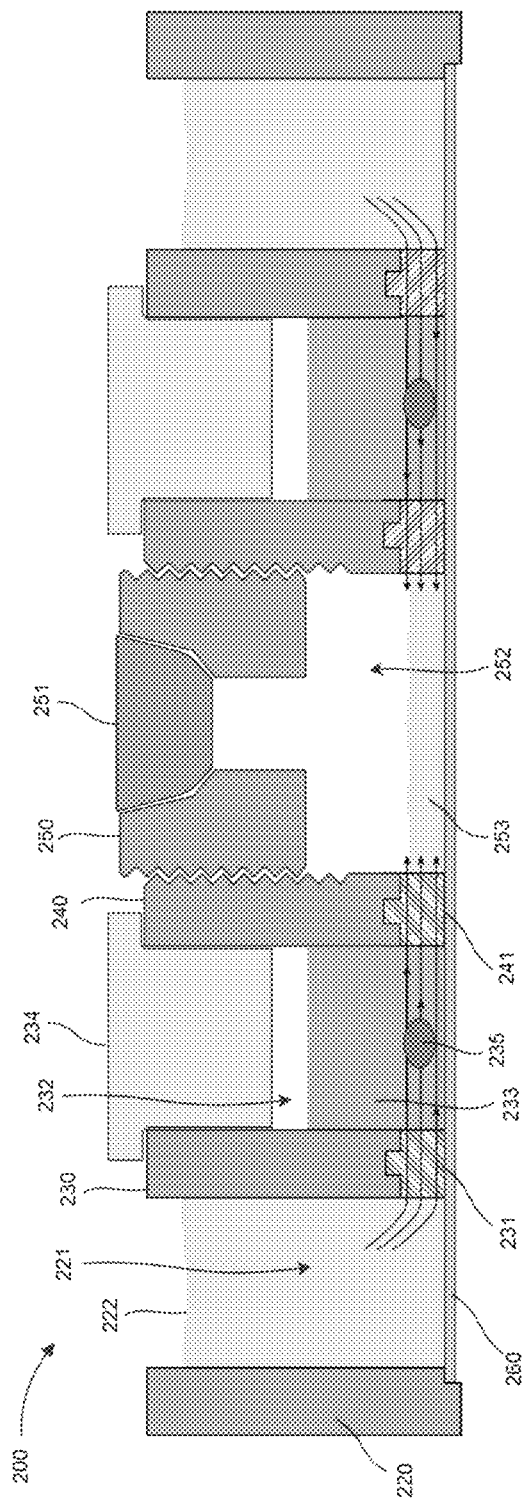
FIG. 4 is a cross-sectional view of one embodiment of a bioreactor system disclosed herein.

FIGS. 3 and 4 depict a second embodiment of a bioreactor system 200 that allows for continuous optical access during the growth of the biological samples. This embodiment has three concentric walls, an outer wall 220, a mid wall 230, and an inner wall 240, all affixed to a bottom plate 260. Also depicted are a plurality of outer spokes 226 connecting the outer wall 220 to the mid wall 230. There are also a plurality of inner spokes 236 connecting the mid wall 230 to the inner wall 240. Together, these walls, spokes, and plate define a plurality of outer (media) chambers 221, a plurality of mid (culture) chambers 232, and a center (media collection) chamber 252, where liquid media 222 flows radially inward from the outer chambers 221, through the mid chambers 232, and into the center chamber 252. Note that in some embodiments, the outer spokes are omitted and there is a single outer chamber feeding media 222 to all mid chambers. The walls are affixed to the bottom plate. The filter material is not continuous around the ring. There are channels cut (shown in the figures) for each separated well the only allow flow through each individual well. This can preferentially direct the flow to the location of the biological sample instead of creating one large inward flow front. It also secures the filter in place to ensure it doesn't detach or shift.

Each of the outer 220, mid 230, and inner walls 240 have a top and bottom surface, as well as an outer surface, and an inner surface. The outer spokes, if present, are affixed to the inner surface of the outer wall, the outer surface of the mid wall, and the bottom plate to provide a seal. The inner spokes are affixed to the inner surface of the mid wall, the outer surface of the inner wall, and the bottom plate to provide a seal. The bottom surface of the outer wall 220 is affixed to the bottom plate 260 to provide a seal. The bottom surface of the mid wall 230 is affixed to a first filter material 231, which is affixed to the bottom plate 260. The bottom surface of the inner wall 240 is affixed to a second filter material 241, which is affixed to the bottom plate 260. This filter is made of the same material as the 3D hydrogel foam that was previously described.

The outer chambers 221 are sized and configured to hold fresh liquid media 222 suitable for the growth of the desired cell type of interest. The mid (culture) chambers 232 are sized and configured to hold 3D cell growth media as well for cell culture. When negative gage pressure is created in the center (media collection) chamber 252, liquid medium 222 is pulled from the outer chamber(s) 221, through the first filter 231, and into the mid (culture) chambers 232. Old liquid medium from the mid (culture) chambers is simultaneously pulled through the second filter 241 and into the center (media collection) chamber 252, where it collects as drawn cell medium 253.

Negative gage pressure can be created in the center chamber 252 using various means. As depicted in FIG. 4, one option is the use of a set screw 250, which acts as a screw-driven actuator. For example, the inner surface of the inner wall 240 can be threaded to receive a set screw 250. If this threading is air-tight, and the screw is properly plugged 251, then the tightening and loosening of the screw 250 alters air pressure in the center chamber 252. Suitable materials for the plug include, but are not limited to, silicone or any type of stiff rubber material that will not negatively interact with the biological materials. In certain embodiments, polydimethylsiloxane (PDMS) or momentiv is used.

As shown in FIG. 4, the mid chambers 232 where samples are cultured can be shielded with a cover 234 to control atmosphere and protect against contamination. The cover 234 can allow for the exchange of gases, and for example, the cover can be produced using a material that is highly permeable to oxygen. In some cases, the cover 234 is produced from polydimethylsiloxane (PDMS). In some cases, the cover 234 is produced from Comfilcon A, Lotrafilcon B, or a combination thereof. In some embodiments, the cover 234 is a single annular structure. In some cases, however, individual covers are used for each mid chamber 232. The cover 234 can be optically transparent so as to allow visual inspection of the underlying chamber without removing the cover.

In preferred embodiments, the bottom plate 260 is optically transparent. Therefore, the bottom plate 260 can be produced from any optically transparent material that is biocompatible, such as glass or polycarbonate.

In some embodiments of the bioreactor system, medium flows radially outward instead of inward. As one of skill in the art would appreciate, this system could be produced in the same manner as the first embodiment, except that negative gage pressure would be produced in the outer chamber, and fresh medium would be added to the center chamber. Likewise, positive pressure could be used instead of negative gage pressure.

Figure 5:
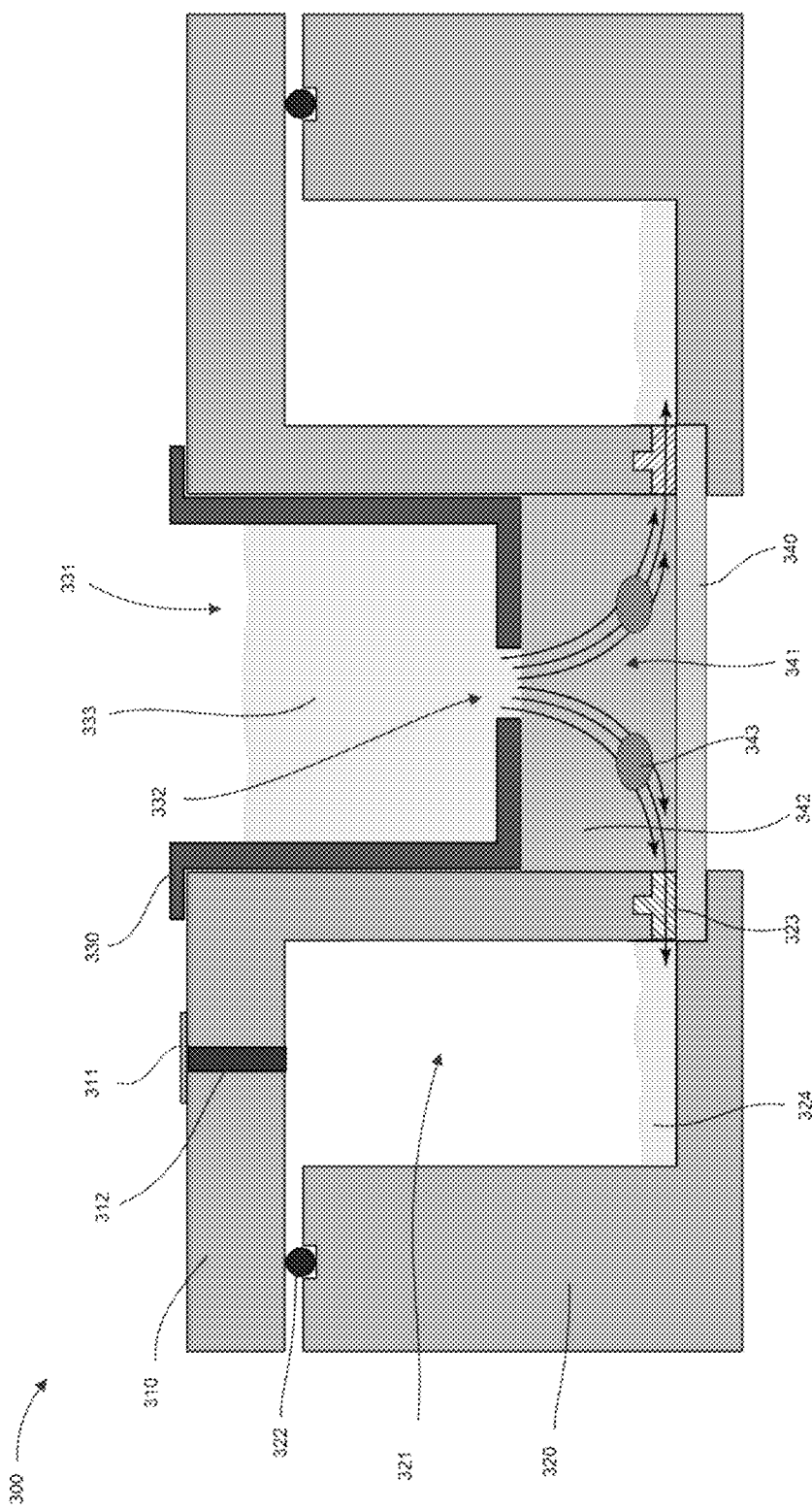
FIG. 5 is a cross-sectional view of one embodiment of a bioreactor system disclosed herein.
Figure 6:
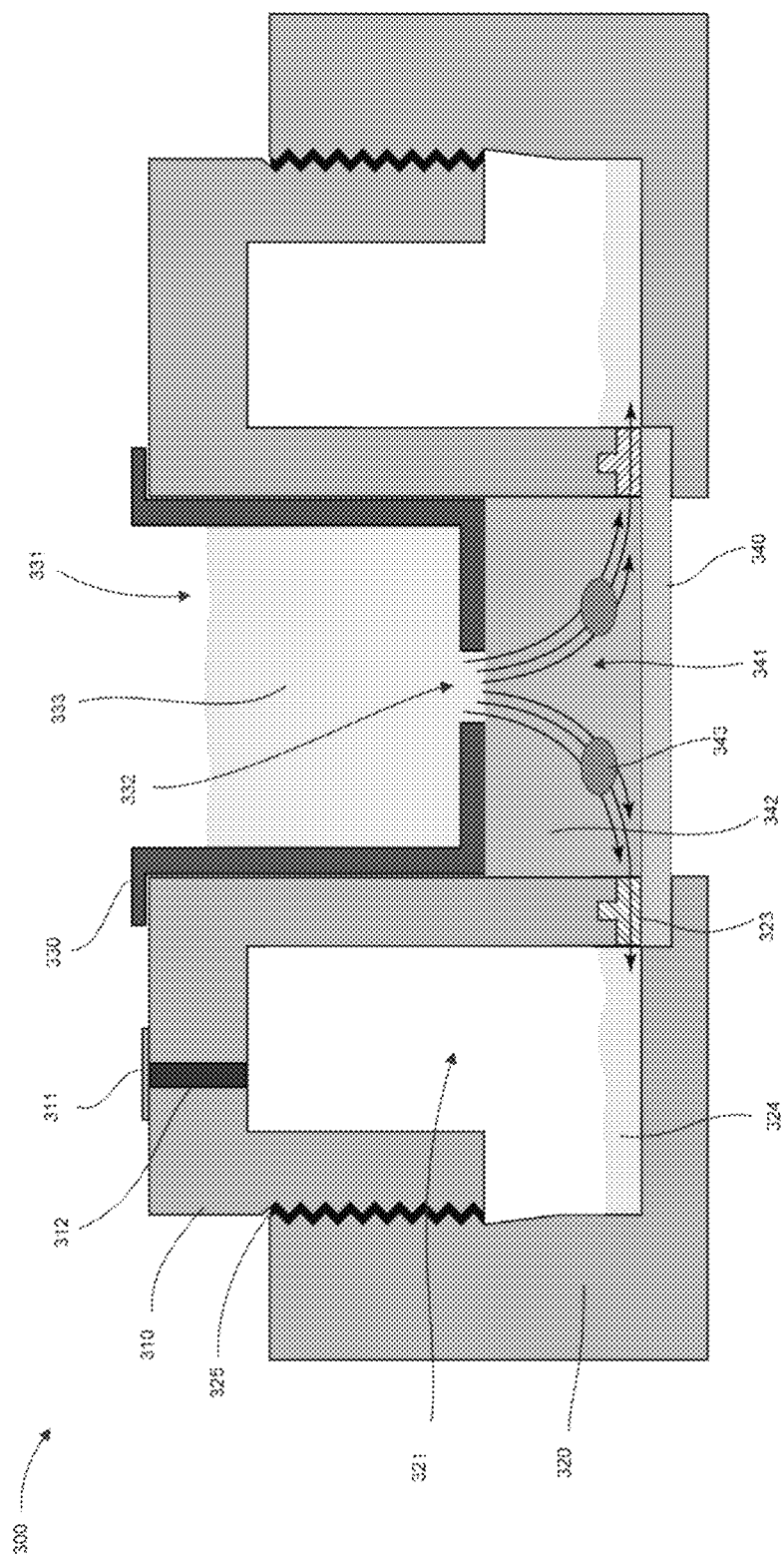
FIG. 6 is a cross-sectional view of one embodiment of a bioreactor system disclosed herein.

FIGS. 5 and 6 depict a third embodiment of a bioreactor system 300 that has radially outward flow where the media 333 flows from a media chamber 331 into a culture chamber 341 nested below and into the 3D growth media (LLS) 342 containing the biological sample 343, and then radially outward from the culture chamber 341 into a media collection chamber 321. The depicted system 300 is assembled from a top dish 310, a bottom dish 320, and a media insert 330. The media insert can be removable. It can have a single hole or multiple holes depending on desired flow.

The depicted top dish 310 comprises a vertical annular wall having an inner surface, an outer surface, a bottom surface, a thickness, and a planar lip extending radially at the top. The bottom surface of this annular wall is affixed to a filter material 323, which is affixed to a bottom plate 340 to form a seal. Therefore, the inner surface of the vertical wall of the top dish 310 and the top surface of the bottom plate 340 form a cylinder that defines a culture chamber 341 having an inner diameter and height.

The depicted bottom dish 320 has a planar portion having a thickness, a top surface and a bottom surface, and annular walls extending vertically having an outer surface, an inner surface, and a top surface. At least one surface of the annular wall is configured to engage the lip of the top dish 310 with an air-tight seal. As shown in FIG. 5, the top surface of the bottom dish 320 annular wall can be configured to receive a gasket 322 that forms a seal between the top surface of the bottom dish 320 annular wall and the bottom surface of the top dish 310 lip. As shown in FIG. 6, the top dish 310 lip can further extend downward into a rim with an outer surface and an inner surface such that it is the outer surface of the rim that engages the inner surface of the bottom dish 320 annular wall. This connection can also be sealed with a gasket. However, as shown in FIG. 6, these surfaces can also be threaded or ridged 422. Materials such as vacuum grease can be used to improve the seal in these embodiments. Any other configuration for engaging the dishes with air-tight seals are contemplated for use in the disclosed system.

When these dishes are engaged (or otherwise mated or operably assembled), a media collection chamber 321 is defined by the outer surface of the top dish 310 annular wall, the bottom surface of the top dish 310 lip, the top surface of the bottom dish 320 planar portion, and the inner surface of the bottom dish 320 annular wall. As shown in FIGS. 5 and 6, a vacuum port 311 can be connected to an opening 312 anywhere in either the top dish 310 or bottom dish 320 so long as it is fluidly connected to the media collection chamber 321.

Liquid medium 333 can be added directly to the culture chamber 341. However, in the depicted embodiments, a media insert 330 is positioned above the culture chamber 341 to define a separate media chamber 331, which can be filled with liquid medium 333. This insert 330 can be a cylinder having an outer diameter less than the inner diameter of the culture chamber 341 and a height that is less than the height of the culture chamber 341. The height of the culture chamber 341 less the height of the media insert 330 defines the area available for cell culture, in which the 3D growth media is housed. To keep the media insert 330 above the culture area, the insert 330 can have a lip extending radially so it will rest on the top surface of the top dish 310 lip. The media insert 330 can have an opening 332 in the bottom so that the media chamber 331 is in fluid communication with the culture chamber 341.

Negative gage pressure can be created by applying a vacuum to the vacuum port 311. As would be appreciated by the skilled artisan, the positioning of this port is not limited to what is depicted in FIG. 5. This will draw liquid medium 333 from the media chamber 331 through the opening 332 in the media insert 330, into the culture chamber 341. At the same time, old medium is pulled from the culture chamber 341, through the filter material 323, into the media collection chamber 321 where drawn cell medium 324 is collected.

Figure 7:
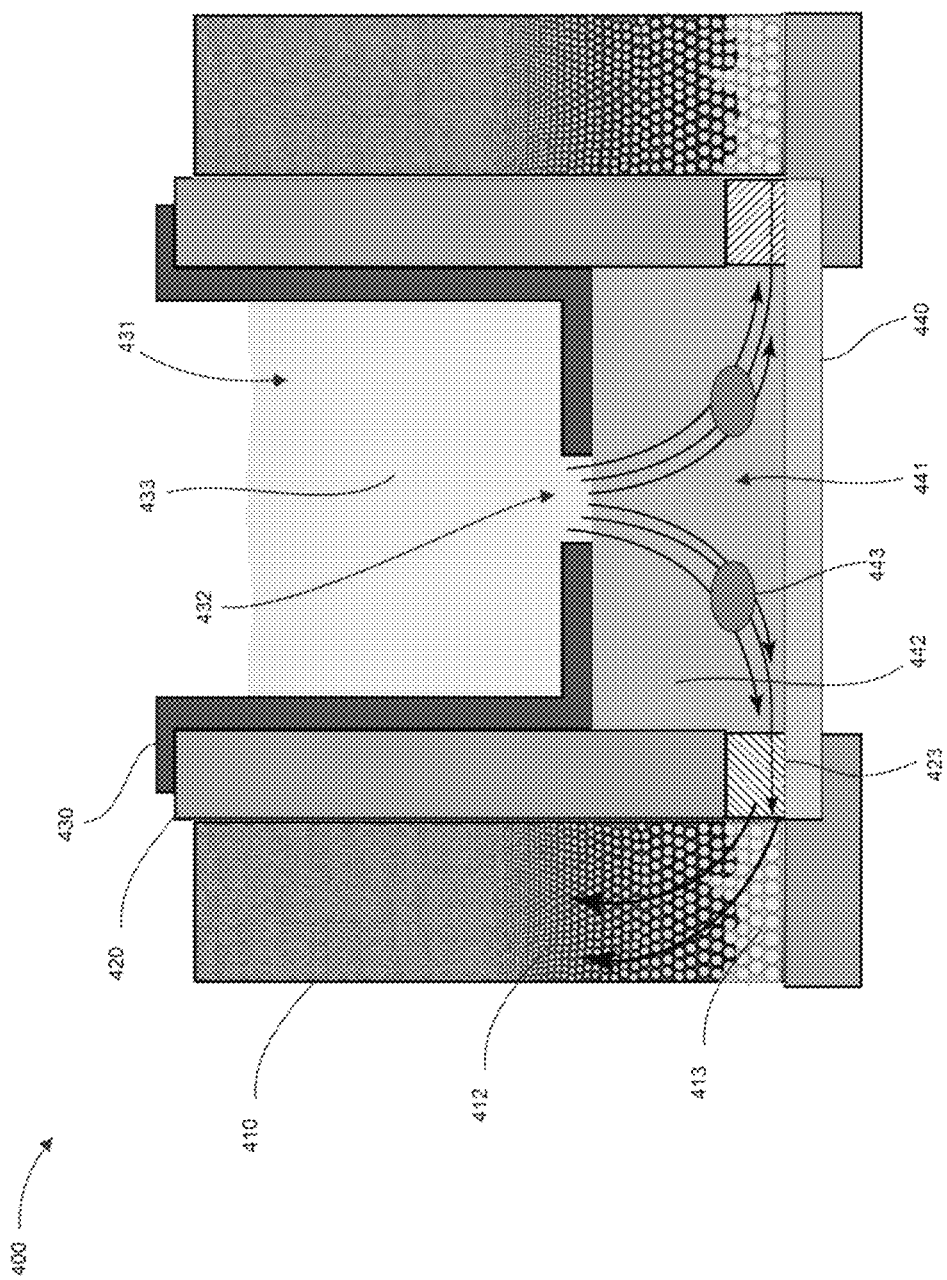
FIG. 7 is a cross-sectional view of one embodiment of a bioreactor system disclosed herein.

FIG. 7 depicts a fourth embodiment of a bioreactor system 400 that differs from the third embodiment in that capillary force is used to draw the medium radially outward. Therefore, the fourth embodiment of a bioreactor system 400 has radially outward flow where the media 433 flows from a media chamber 431 into a culture chamber 441 nested below, and then radially outward from the culture chamber 441 into a media collection chamber 421. The depicted system 400 is assembled from a bottom dish 420, a media insert 430, and a capillary device 410 in fluid communication with the culture chamber 441.

The capillary device 410 can comprise microradius glass tubule. The capillary device 410 can comprise sintered microparticles that have innate contact angle with liquid media that produces significant wetting and therefore large capillary forces. Suitable examples include borosilicate glass, steel, and various ceramics; however, materials can be engineered to generate a specific pressure gradient and induce a specific flow velocity.

The depicted bottom dish 420 comprises a vertical annular wall having an inner surface, an outer surface, a bottom surface, and a thickness. The bottom surface of this annular wall is affixed to a filter material 423, which is affixed to a bottom plate 440 to form a seal. Therefore, the inner surface of the vertical wall of the bottom dish 420 and the top surface of the bottom plate 440 form a cylinder that defines a culture chamber 441 (housing the 3D growth media) having an inner diameter and height.

Materials such as vacuum grease can be used to improve the seal in these embodiments. Any other configuration for engaging the dishes with air-tight seals are contemplated for use in the disclosed system.

Liquid medium 433 can be added directly to the culture chamber 441. However, in the depicted embodiments, a media insert 430 is positioned above the culture chamber 341 to define a separate media chamber 431, which can be filled with liquid medium 433. This insert 430 can be a cylinder having an outer diameter less than the inner diameter of the culture chamber 341 and a height that is less than the height of the culture chamber 441. The height of the culture chamber 441 less the height of the media insert 430 defines the area available for cell culture (where the 3D growth media is placed). To keep the media insert 430 above the culture area, the insert 430 can have a lip extending radially so it will rest on the top surface of the bottom dish 420. The media insert 430 can have an opening 432 in the bottom so that the media chamber 431 is in fluid communication with the culture chamber 441.

Figure 8:
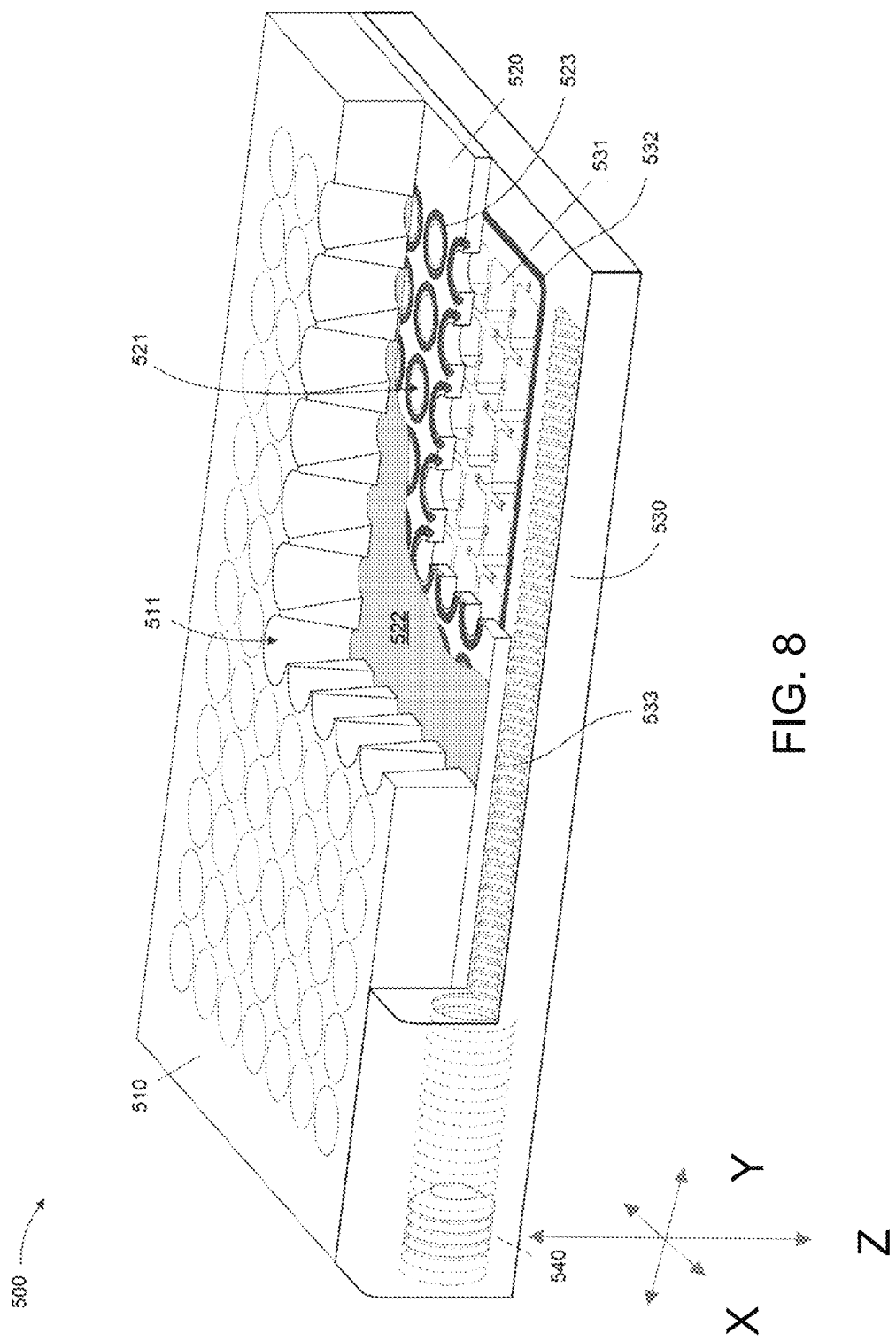
FIG. 8 is a cutaway view of one embodiment of a bioreactor system disclosed herein showing a high-throughput multi-well configuration.
Figure 9A:
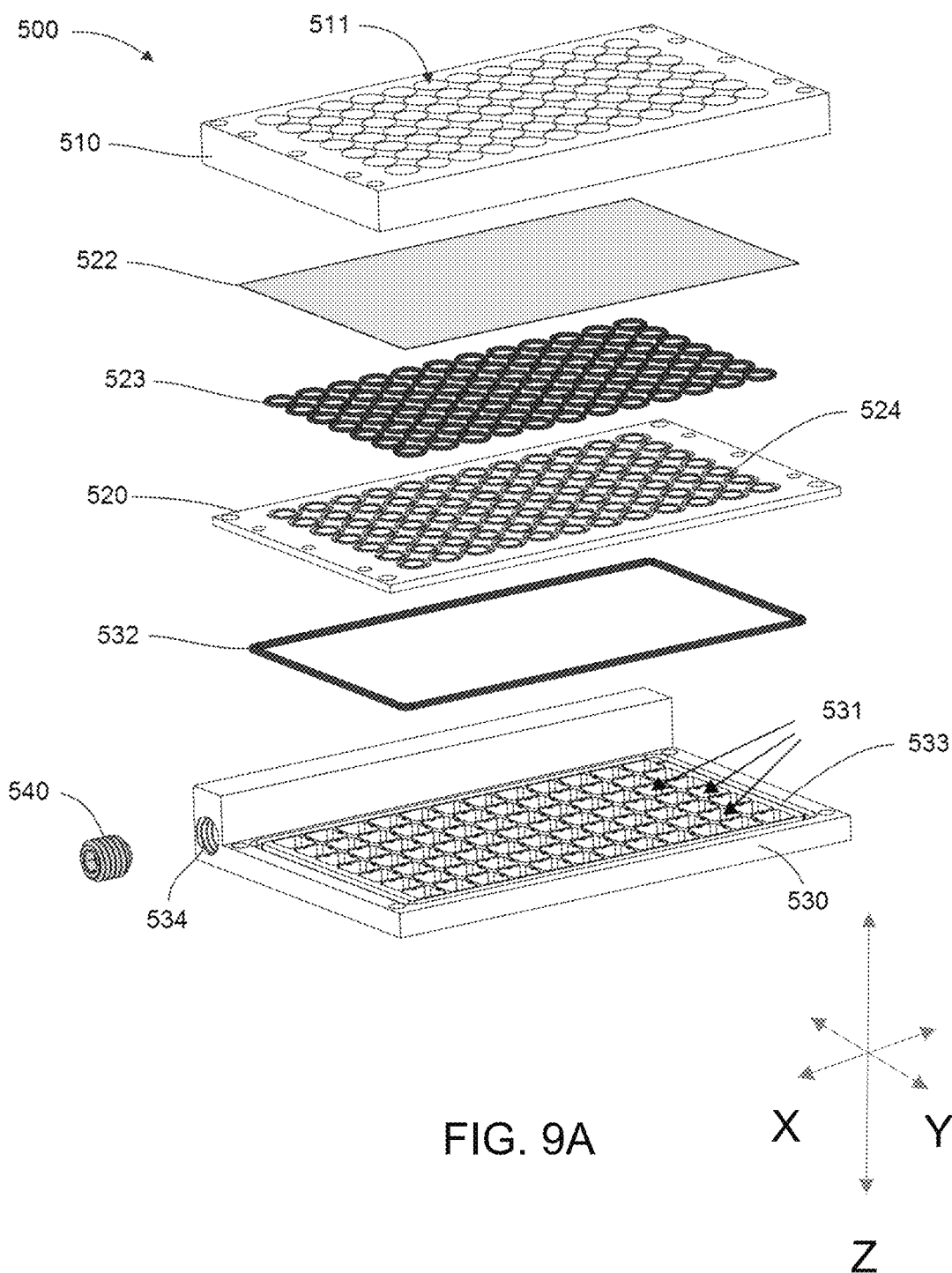
FIG. 9 is an exploded view of one embodiment of a bioreactor system disclosed herein.
Figure 9B:
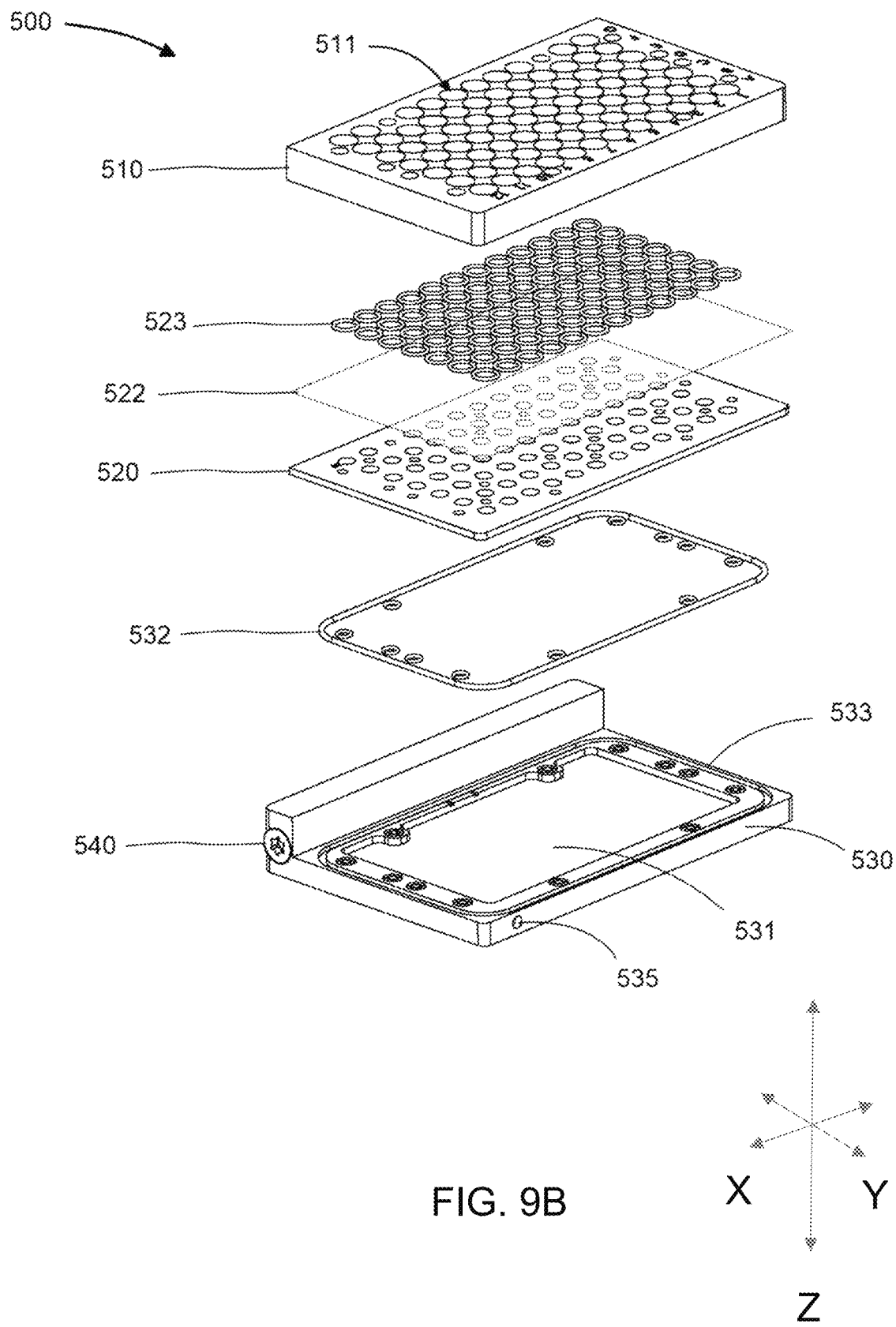

FIGS. 8, 9A, and 9B depict a fifth embodiment of a bioreactor system 500 that differs from the first embodiment in how the negative gage pressure is created. As with the first embodiment, the wells of the bioreactor system 500 are preferably arrayed in columns and rows. The depicted bioreactor system 500 uses a set screw 540 rotatably mounted within the base plate 530 to create a vacuum to draw media from the sample wells 511 through a filter material 522 and into a media collection chamber(s) 531.

As best appreciated in the exploded views of FIGS. 9A and 9B, the depicted bioreactor system 500 is assembled from three horizontal plates, a well plate 510, a center plate 520, and a base plate 530.

As depicted in FIGS. 8, 9A, and 9B, negative gage pressure can be created using a set screw 540 rotatably mounted within the base plate 530 (i.e. a screw-driven actuator). For example, a vacuum chamber 534 fluidly connected to the media collection chamber(s) 531 can be threaded to receive a set screw 540. If the vacuum chamber 534 and threading is air-tight, then the tightening and loosening of the screw 540 alters air pressure in the media collection chamber(s) 531.

The depicted well plate 510 is a planar material having a top surface, a bottom surface, and a thickness corresponding to the desired well height. The sample wells are defined by orifices 511 extending from the top surface to the bottom surface of the well plate 510 and a filter material 522 positioned below the well plate 510. The bottom of each well is therefore defined by the filter material 522 compressed between the well plate 510 and the center plate 520. In some cases, there are a plurality of filters 522, such as one for each well. In some cases, as shown in FIGS. 8 and 9, there is a single filter material 522 acting as the bottom for all of the wells.

The depicted center plate 520 can comprise a plurality of apertures 521 configured to align with the orifices 511 when the plates are staked together. In order to provide a seal, one or more gaskets 523 can be positioned between the center plate 520 and the filter material 522. Therefore, the center plate 520 can contain one or more grooves 524 for seating the one or more gaskets 523. As shown in FIGS. 8 and 9, these grooves 524 can be positioned around the perimeter of each aperture 521, or these grooves 524 can be posited around the perimeter of the array of apertures 521. As will be appreciated by one of skill in the art, the grooves 524 and filter material 522 should be sized and positioned to provide a seal when the gasket 523 is seated in the groove 524.

The depicted base plate 530 is a planar material having a top surface, a bottom surface, and a thickness, that forms one or more media collection chambers 531 below the center plate 520 when the plates are stacked together. In order to provide a seal, a second gasket 532 can be positioned between the base plate 530 and the center plate 520. Therefore, the base plate 530 can contain a trench 533 for seating the second gasket 532 positioned around the medium collection chamber(s) 531. In some embodiments, the base plate 530 contains a drainage port 535 fluidly connected to the medium collection chamber(s) 531.

As described above, the 3D cell growth medium (also referred to herein as LLS) for each of the above depicted systems may include a thixotropic or yield stress material, or any material suitable for temporary phase changing. In some examples, the thixotropic or yield stress material may include a soft granular gel. The soft granular gel may be made from polymeric hydrogel particles swelled with a liquid cell culture medium. Depending on the particular embodiment, the hydrogel particles may be between 0.5 μm and 50 μm in diameter, between about 1 μm and 10 μm in diameter, or about 5 μm in diameter when swelled.

Sensors can be used to detect changes in pressure, pH, oxygen levels, specific metabolites such as glucose, presence or absence of an indicator molecule such as a viral protein, or any other indicia of an effect on the tissues or a material exposed to the tissues within the bioreactor.

Liquid Medium

Liquid medium composition must be considered from two perspectives: basic nutrients (sugars, amino acids) and growth factors/cytokines. The composition of the liquid medium for the system will depend upon the cells which are to be cultured by bioreactor systems as described herein. The choice of liquid medium is routine in the art to the skilled artisan. Co-culture of cells often allows reduction or elimination of serum from the medium due to production of regulatory macromolecules by the cells themselves. The ability to supply such macromolecular regulatory factors in a physiological way is a primary reason 3D perfused co-cultures are used. A serum-free medium supplemented with several growth factors suitable for long-term culture of primary differentiated hepatocytes has been tested and found to support co-culture of hepatocytes with endothelial cells. ES cells are routinely maintained in a totipotent state in the presence of leukemia inhibitory factor (LIF), which activates gp130 signaling pathways. Several medium formulations can support differentiation of ES cells, with different cytokine mixes producing distinct patterns of differentiation. Medium replacement rates can be determined by measuring rates of depletion of key sugars and amino acids as well as key growth factors/cytokines. If cell culture medium with sodium bicarbonate is used, the environmental control can be provided by e.g. placing the module with bioreactor/reservoir pairs into a $CO_2$ incubator.

Cells

A variety of different cells can be applied to the 3D growth medium of the disclosed systems. In the some embodiments, these are normal human cells or human tumor cells. The cells may be a homogeneous suspension or a mixture of cell types. The different cell types may be seeded onto and/or into the medium sequentially, together, or after an initial suspension is allowed to attach and proliferate (for example, endothelial cells, followed by liver cells). Cells can be obtained from cell culture or biopsy. Cells can be of one or more types, either differentiated cells, such as endothelial cells or parenchymal cells, including nerve cells, or undifferentiated cells, such as stem cells or embryonic cells. In one embodiment, the medium is seeded with a mixture of cells including endothelial cells, or with totipotent/pluripotent stem cells which can differentiate into cells including endothelial cells, which will form "blood vessels", and at least one type of parenchymal cells, such as hepatocytes, pancreatic cells, or other organ cells.

Cells can be cultured initially and then used for screening of compounds for toxicity. Cells can also be used for screening of compounds having a desired effect. For example endothelial cells can be used to screen compounds which inhibit angiogenesis. Tumor cells can be used to screen compounds for anti-tumor activity. Cells expressing certain ligands or receptors can be used to screen for compounds binding to the ligands or activating the receptors. Stem cells can be seeded, alone or with other types of cells. Cells can be seeded initially, then a second set of cells introduced after the initial bioreactor tissue is established, for example, tumor cells that grow in the environment of liver tissue. The tumor cells can be studied for tumor cell behaviors or molecular events can be visualized during tumor cell growth. Cells can be modified prior to or subsequent to introduction into the apparatus. Cells can be primary tumor cells from patients for diagnostic and prognostic testing. The tumor cells can be assessed for sensitivity to an agent or gene therapy. Tumor cell sensitivity to an agent or gene therapy can be linked to liver metabolism of set agent or gene therapy. Cells can be stem or progenitor cells and the stem or progenitor cells can be induced to differentiate by the mature tissue. Mature cells can be induced to replicate by manipulation of the flow rates or medium components in the system.

Cells are cultured in bioreactor systems as described herein in the 3D growth media. Cells can be placed (or "plated") in the growth media by a variety of techniques in the art, such as manual pipetting by a user, robotic liquid handling systems, 3D printers, and the like.

Applications

The system has many different applications, such as identification of markers of disease; assessing efficacy of anti-cancer therapeutics; testing gene therapy vectors; drug development; screening; studies of cells, especially stem cells; studies on biotransformation, clearance, metabolism, and activation of xenobiotics; studies on bioavailability and transport of chemical agents across epithelial layers; studies on bioavailability and transport of biological agents across epithelial layers; studies on transport of biological or chemical agents across the blood-brain barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratinogenicity of chemical agents; studies on genotoxicity, carcinogenicity, and mutagenicity of chemical agents; detection of infectious biological agents and biological weapons; detection of harmful chemical agents and chemical weapons; studies on infectious diseases; studies on the efficacy of chemical agents to treat disease; studies on the efficacy of biological agents to treat disease; studies on the optimal dose range of agents to treat disease; prediction of the response of organs in vivo to biological agents; prediction of the pharmacokinetics of chemical or biological agents; prediction of the pharmacodynamics of chemical or biological agents; studies concerning the impact of genetic content on response to agents; filter or porous material below microscale tissue may be chosen or constructed so as bind denatured, single-stranded DNA; studies on gene transcription in response to chemical or biological agents; studies on protein expression in response to chemical or biological agents; studies on changes in metabolism in response to chemical or biological agents; prediction of agent impact through database systems and associated models; prediction of agent impact through expert systems; and prediction of agent impact through structure-based models.

Methods

Described herein are methods of using perfusion-enable bioreactor systems as described herein. Methods of use can comprise providing a bioreactor system as described herein. Methods of use can comprise providing and preparing a bioreactor system as described herein, providing and preparing the LLS of bioreactor systems as described herein, placing the LLS into the bioreactor system, providing one or more biological samples, and pipetting one or more biological samples into the LLS of the bioreactor system. Methods of use can further comprise providing a positive or negative gage pressure to the system to provide active perfusion flow through one or more flow paths of the system. Methods of use can further include providing one or more drugs (such as small molecules, proteins, nucleic acids, and the like) to a system as described herein. Methods of use can further include providing one or more drugs to a system as described herein, imaging the biological samples, and analyzing the images of the biological samples.

Kits

Described herein are kits. Kits as described herein can comprise a perfusion-enabled bioreactor system as described herein. A kit can comprise one or more perfusion-enabled bioreactor systems configured as one or more discrete imaging pods. A kit can comprise one or more perfusion-enabled bioreactor systems configured as one or more discrete imaging pods and a cassette with a base container and a lid. A kit can comprise one or more perfusion-enabled bioreactor systems configured as a high throughput multi-well plate-based array. Kits as described herein can further comprise a pressure generating means, such as a syringe with a needle configured to pierce a self-healing annular seal. Kits as described herein can further comprise a pressure gauge. Kits as described herein can further comprise a device for actuating the screw-driven actuator of a bioreactor system as described herein, for example a screwdriver. Kits as described herein can comprise the physical hardware needed for the perfusion-enabled bioreactor systems as described herein in addition to the components necessary to make and use the LLS. Kits as described herein can comprise the physical hardware needed for the perfusion-enabled bioreactor systems as described herein in addition to the components necessary to make and use the LLS and the 3D hydrogel filter.

Mechanical Pipetting Guide for Precision Placement of Features

The 3D printing of biological materials is often technologically complex and can also be expensive. For researchers who wish to observe 3D biological constructs, placing those constructs precisely without the use of a 3D printer or robotics can prove to be extremely difficult. Bioreactor systems as described herein can include mechanical pipetting guides, such as those described herein. Such mechanical pipetting guides will allow the user to precisely "3D print" biological materials with the use of a standard pipette, and without need to use expensive equipment they may not have access to.

Mechanical pipetting guides for precision placement of features in 3D as described herein can be an apparatus that enables the use of a mechanical pipette to disperse material at a precise location within a well of a bioreactor plate or any well plate. The device constrains the location of the pipette tip in three dimensions, allowing the user to insert the pipette into a well at a known height and known x and y location. This can be used as a way to "3D print" materials by hand in a gel based medium (i.e. 3D growth medium or LLS) without the use of electronics or robotics. In bioreactor plates with imaging capabilities, this allows materials to be placed at a precise and repeatable height where high magnification microscopy is possible due to the precise placement of features within the same focal plane relative to the imaging optics of the microscope. Such guides also allows for the creation of different arrays of shapes, where multiple material constructs can be placed relative to one another in a precise manner in 3D.

Aspects of the present disclosure include allowing the user to "print" in varying well plate types and at varying XYZ coordinates within the wells. The guide mimics the results achieved by a high precision 3D printer without the use of the printer or time and cost associated with this level of automation. The user can use a single guide to quickly and repeatedly print a construct into an imaging enabled plate for experimentation. The user can also have an assortment of guides, each specifying the construct shape and the maximum magnification level that can be used to image the construct. The guides can print multiple constructs allowing the user effectively infinite combinations of construct shapes and imaging magnification levels.

As one of skill in the art would understand, such guides can also form an array, enabling the use of a plurality of pipette tips at the same time, for example with standard laboratory multichannel micropipettes.

Because the guide can allow the user to "3D print" at any desired height or location within a well, users could place one biological material type in a well or could potentially study co-culture in 3D. This product could lower expenses for research labs who wish to simulate 3D printing of biological materials without the need for expensive equipment. The guide would allow a user to place material in 3D in an extremely precise manner. The set up and use of the guide is very user friendly and also is very time efficient, and can simplify the process of 3D printing biological samples.

Such mechanical pipette guides as described herein can be adjustable as to accommodate a variety of pipette tips of different sizes and from different manufacturers. Guides can be adjustable so as to have variable apertures in one dimension, and can be adjusted for height in other dimensions.

An embodiment of a mechanical pipette guide 600 as described herein is shown in the cross-sectional view of FIG. 10. As depicted in FIG. 10, the mechanical pipette guide 600 can be configured to abut one or more top surfaces 612 of an aspect of a bioreactor system 614 in which the user desires to pipette features, for example cells 640, into the 3D growth medium contained in a culture chamber 617. The mechanical pipette guide 600 can also be configured with a lip 614 around the outer periphery of the device 600 extending downward that is configured to abut one or more outer sides of a structure 610 into which pipetting will take place.

FIG. 10 illustrates an embodiment 600 according to the present disclosure. As can be seen from the cross-sectional view of FIG. 10, the pipette 620 (also a disposable pipette tip) is constrained in several dimensions (for example Z and X and Y). The allows the precise placement of features, such as cells 640, into the bioreactor system 610 with a known and repeatable height 630 relative to the bottom of the culture chamber 616, the media collection chamber, or the liquid reservoir.

Cassette-Based Multiwell Plates:

Imaging perfusion pods (also referred to herein as discrete bioreactor units) allow for biological samples (such as cells) to be cultured in a 3D environment with lifespans longer than other culture methods. In situ imaging can be performed on the biological samples, allowing users to track growth and changes within the same sample over prolonged periods of time. In order to image, each pod must be individually transported to a microscope and placed into a preexisting fixture on the microscope. By using a cassette-based multiwell system, several imaging pods can be fixtured to the same container to allow for easier transport and imaging.

Aspects of the present disclosure include of a cassette-based multiwell system which includes a base container and a lid. The cassette can hold multiple imaging pods, which can be securely fixtured to the base. Each imaging pod is fixed to a number of tapered posts (for example six tapered posts—three on each side of the pod) that mount the imaging pod inside the cassette via an over constrained interference fit. The base of the cassette has viewing ports to allowing for imaging through the glass viewing window of each of the imaging pods. The lid of the cassette allows for access to view the wells of the pods. This lid also provides an air gap for adequate gas exchange, air flow, and can provide habitable conditions within the cassette. The lid can be removed and replaced with a different lid that can convert the entire cassette into an incubator. This conversion is as easy as putting on a new lid to the cassette and attaching any necessary gas lines (through one or more gas ports located anywhere on the cassette) and heat sources. This is especially useful during microscopy as the prolonged time out of an incubator environment can alter experimental results.

Aspects of the present disclosure include the ability to store, transport, and image all within the same system. The entire system can be incubated and imaging pods experience minimal individual handling during feeding and transport. The cassette provides precise repeatability in the XYZ location of the plate. The cassette also allows access to the viewing ports on the bottom of the plates for imaging purposes. The entire cassette can be placed on a microscope to study experiments with the ease that comes with a standard well plate. The XYZ locations of each well can be recorded and used for subsequent imaging to maintain the same orientation. The cassette features a sliding lid to protect the plates during handling. The lid features adequate gaps to allow for gas, humidity, and air flow around the plates in an incubator.

Aspects of the present disclosure will enable users to image imaging pods in a more precise manner, while also allowing for better handling, transport, and storing of imaging pods. Aspects of the present disclosure would result in a cassette that could be used in conjunction with imaging pods and other variations of this product. When tracking changes in biological samples, users can repeatable image in the same location due to the high repeatability in fixturing within the cassette and on the microscope. Any user of the imaging pods would also want to purchase this as an aid for imaging, storage, and handling.

Figure 11:
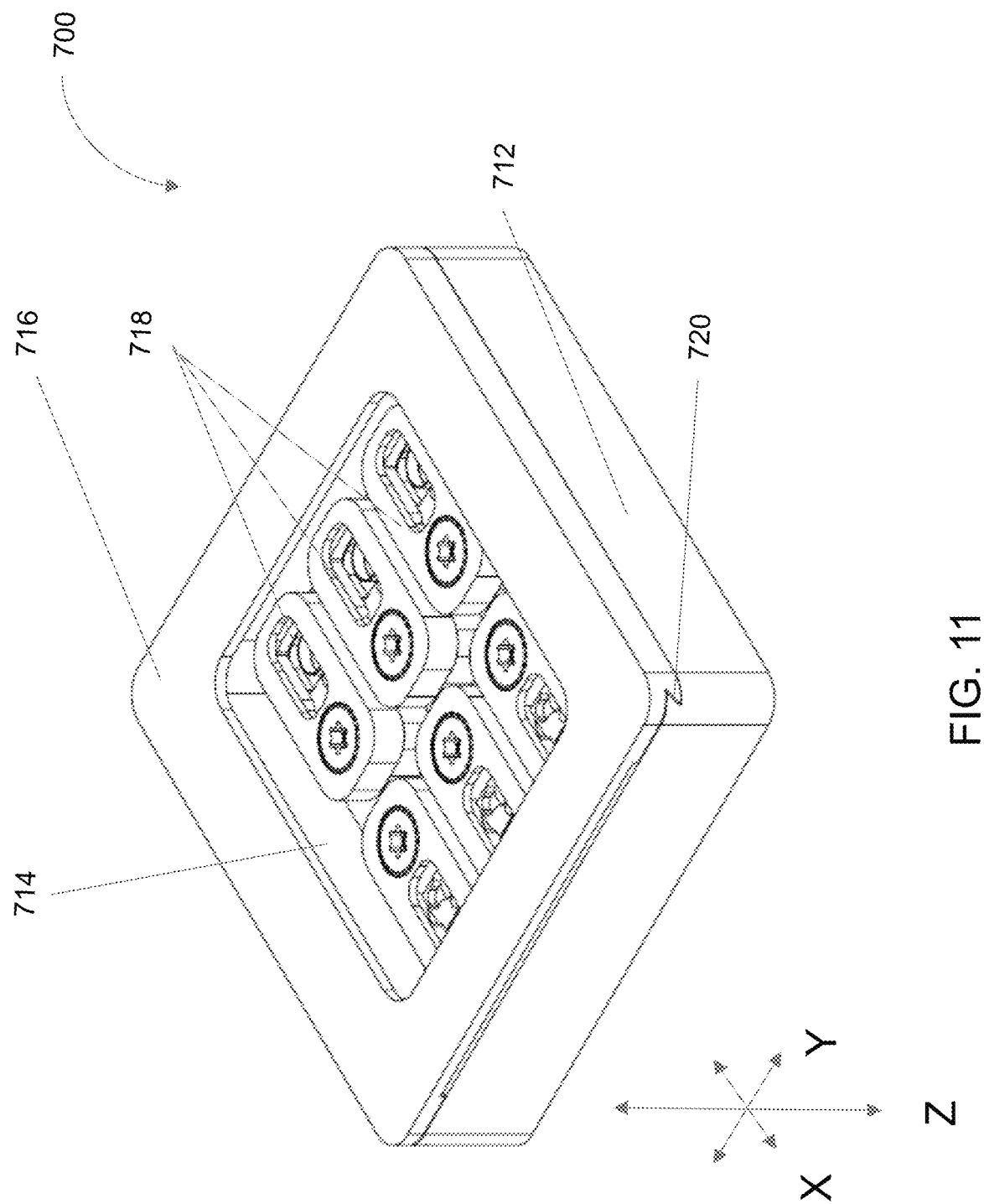
FIG. 11 is an embodiment of a cassette-based multi-well bioreactor system as described herein configured for a plurality (six) of discrete bioreactor units.

An embodiment of a cassette-based multiwall plate 700 is depicted in FIG. 11 in a closed or assembled position. As can be seen in FIG. 11, the embodiment of the cassette 700 comprises a base container 712 having a chamber 714 configured to receive discrete imaging perfusion pods 718 (also referred to herein as discrete bioreactor units) and a lid 716 that is configured to securely cover the base container 712. In the embodiment of FIG. 11, the lid-securing apparatus is a dovetail 720 that allows the lid 716 to slide onto the base container 712 so that it cannot be easily pried off without sliding. The embodiment 700 of FIG. 11 is square and configured to hold 6 imaging pods 718, but, as one of skill in the art would understand, the cassette 700 can be configured to any reasonable size or shape or for any reasonable number of discrete imaging pods 718 depending on the needs of the user.

As previously mentioned, the cassette can be operably coupled to one or more gas sources (for example oxygen, nitrogen, and carbon dioxide) through one of more gas ports which can be positioned on any surface of the cassette or the cassette lid.

The cassette can also be operably coupled to a heat source to provide heat to imaging pods, for example through a hot plate, water bath, or other common heating devices.

The cassette or cassette lid can be constructed of a plastic or other material, such as metal.

The lid of the cassette can contain an optically transparent viewing window of any size comprising an optically transparent material such as glass or plastic. In certain aspects, the cassette lid may not be optically transparent.

Figure 12:
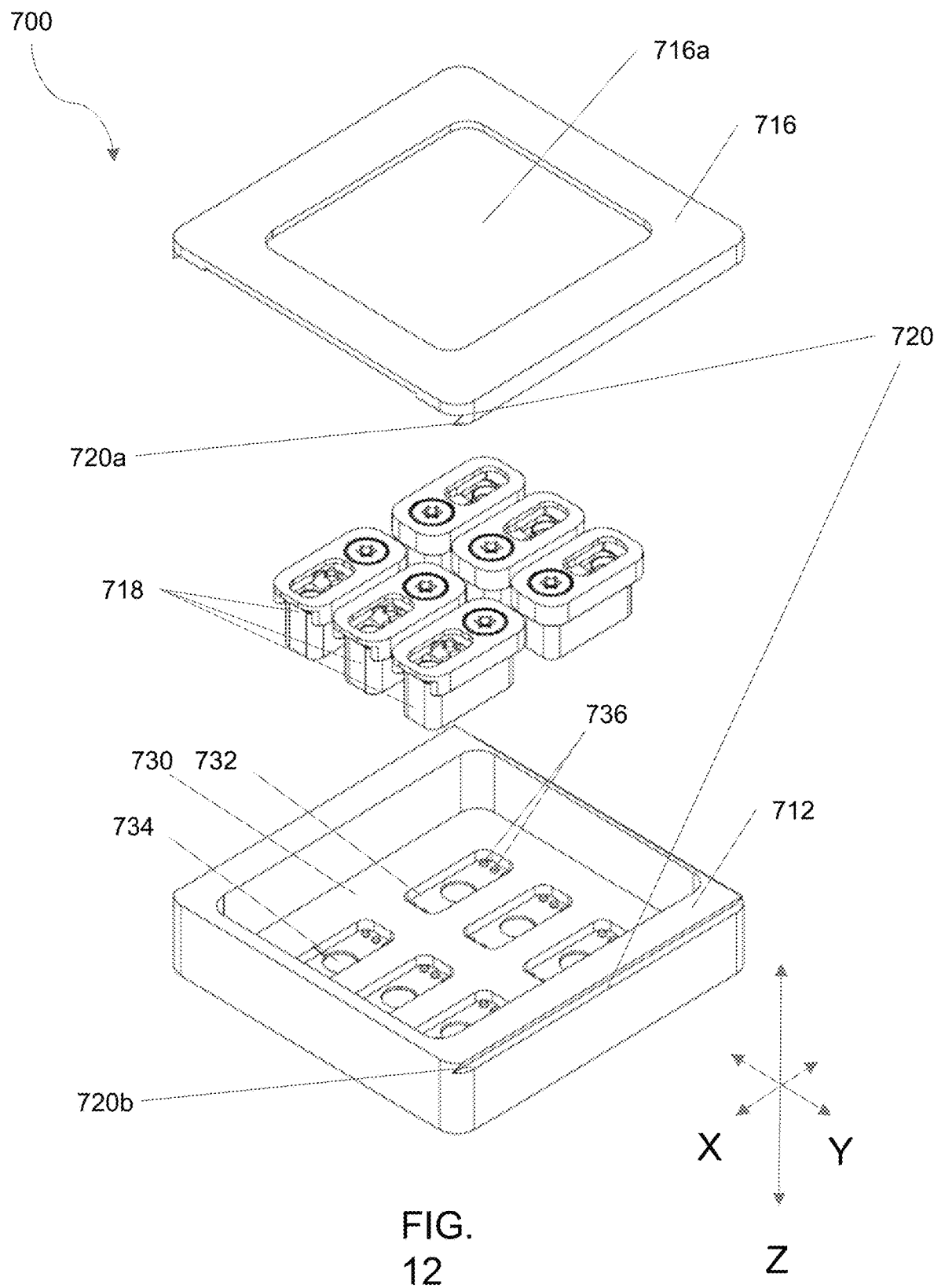
FIG. 12 is an exploded view of the cassette-based multi-well bioreactor system of FIG. 11.

The embodiment and other aspects of the cassette-based system 700 are illustrated in the exploded view of FIG. 12. As can be seen in the exploded view, the cassette 700 can comprise an optically transparent viewing window 716a (made of glass, plastic, or other transparent material), and one of skill in the art would understand the exact size and shape of the optically transparent portion can be varied according to the needs of a user.

The cassette lid 716 can be configured to securely mate with or assemble with the base container 712. The embodiment of FIG. 12 depicts a dove-tail structure 720 wherein a lip 720a on one or more outer edges of the lid 716 is configured to be placed in a groove 720b on one or more outer top areas of the base container 712, although other securing devices (such as interference fit posts and latches) can be used as one of skill in the art would understand.

As can be seen from the exploded view of FIG. 12, a surface 730 of the base container that faces the lid can have recesses 732 that are the shape of the bottom surface of the discrete imaging pods 718 so that a discrete imaging pod 718 can be secured to a recess. The recess can have an optically transparent imaging window 734 or hole to allow for a light path to illuminate a vertical column throughout that position of the cassette 700.

The recess can also have one or more pod-securing mechanisms 734. An embodiment of a pod-securing mechanisms is described below. In the embodiment, one or more frustoconical tapered annular posts 734 extending from the surface of the recess of the base container 732 that faces the lid toward the lid, wherein the post 734 is tapered so that the base has a larger diameter than the tip of the post. The discrete imaging pod 718 can have a receiving hole on the bottom or annular frustoconical recess configured to receive a post to provide a snug interference fit, thereby securing the imaging pod 718 within the cassette 700 in one or more of the X-, Y-, or Z-axis. The cassette 700 can also be configured so that the height of the cassette, from the bottom surface of the lid that faces the base container to the surface of the base container that faces the lid 730 is about the same height as the discrete imaging pod 718, thereby securing the pod in that manner.

Repeatable Positioning Method Using Tapered Post Fixturing:

Traditional kinematic mounting solutions are both precise and repeatable. However, some of the drawbacks are found in the ability for the necessary features to be manufactured and how well they can be implemented in various designs. The present disclosure describes a fixturing configuration that is easily manufactured and has a wide range of applications.

This aspect describes a fixturing configuration comprised, in an embodiment, of three or more tapered posts on component one of the assembly that mate to tapered alignment holes on the second component. Using multiple tapered posts allows for an over constrained interference fit to force the unfixed component into alignment. The taper engages the internal wall of the tapered alignment hole, centering each post and alignment hole pair. Once component one is fixtured, it is rigidly held in place. The component can then be removed easily from the tapered posts, and can be placed back onto the tapered posts with repeatable precision.

Aspects of the present disclosure include the simple yet effective geometry of the tapered post and the its tapered alignment hole counterpart. This geometry can be implemented in a wide array of designs and is much easier to manufacture than traditional kinematic mounting solutions. Utilization of the aspects of the present disclosure is easy as well, as placing and removing a component takes little vertical force to engage or disengage the tapered post on the wall of the alignment hole. However, it takes great lateral force to shift the system, making the component rigidly fixtured without issue in most applications.

Specific applications of this fixturing method include the repeated microscopy of biological samples and the repeatable placement of well plates during the 3D printing of biological materials. Microscopy enabled perfusion plates, or any microscopy enabled well plate, can be fixed to the microscope using this method. A microscope can have a receiving plate which includes the tapered post component of this fixturing system, while the microscopy enabled plate contains the alignment hole component. The sample can be placed on the microscope, imaged, and then can be removed. This sample can be imaged at different time points over several days and weeks at the same location within the well since it can be precisely fixtured in the same place each time. This allows for the precise tracking of mobile cells and growth of tissues. A similar system can be used during the 3D printing of biological samples. A well plate can be fixtured for printing, printed into, and then stored to allow the biological sample to mature. It can then be returned to the printer at a later time point and can be printed into again, which can be very useful when attempting co-culture in 3D.

Aspects of the present disclosure can be applied to a wide variety of products, including but not limited to well plates, microscopes, and biological 3D printing fixturing. For example, a wellplate and microscope plate insert can utilize this fixturing method, allowing the user to repeatably place a wellplate precisely on the microscope. For 3D printing, well plates can be fixtured precisely and securely during the printing process.

Aspects of the present disclosure allows for easy, repeatable, and precise placement of components. A user can easily place or remove an item with little vertical force applied, allowing for the user to gently fixture an item like a well plate without disturbing its contents. For manufacturing, the tapered posts and alignment holes are much simpler to machine and incorporate into designs. Aspects of the present disclosure also can increase accuracy during the microscopy of biological samples, allowing well plates to be imaged, removed from the microscope, and imaged again in the same region at a later time point.

Figure 13A:
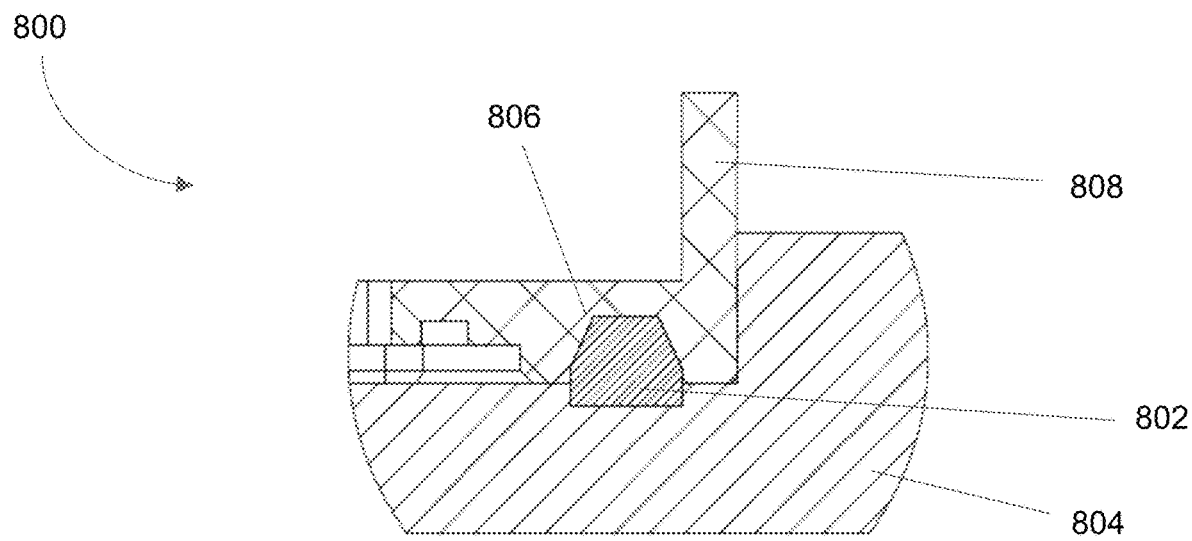
FIGS. 13A-13B is an embodiment of features of bioreactor systems as described herein that confer stable and repeatable positioning of discrete bioreactor units.

Aspects of such repeatable positioning system were described above and illustrated more closely in FIGS. 13A-13B. FIG. 13A shows an enlarged cross-sectional view of a repeatable positioning system as described herein, an embodiment of which is also shown in the cassette of FIG. 12. The cross-sectional view of FIG. 13A shows a substrate 804 (first component) engaged with a detachable specimen 808 (second component) through such a tapered post fixturing system 802. As can be seen in FIG. 13A, a tapered male post 802 exists on the substrate that extends upward towards the detachable specimen 808, and engages the detachable specimen 808 in recesses 806 that are configured to receive the post 802 and to complement the geometry of the post 802. In an embodiment, the post 802 is an annular frustoconical post and a recess 806 is configured to receive such, but the intent is not for the present disclosure to be limited to specifically that geometry, as one of skill in the art would understand.

Figure 13B:
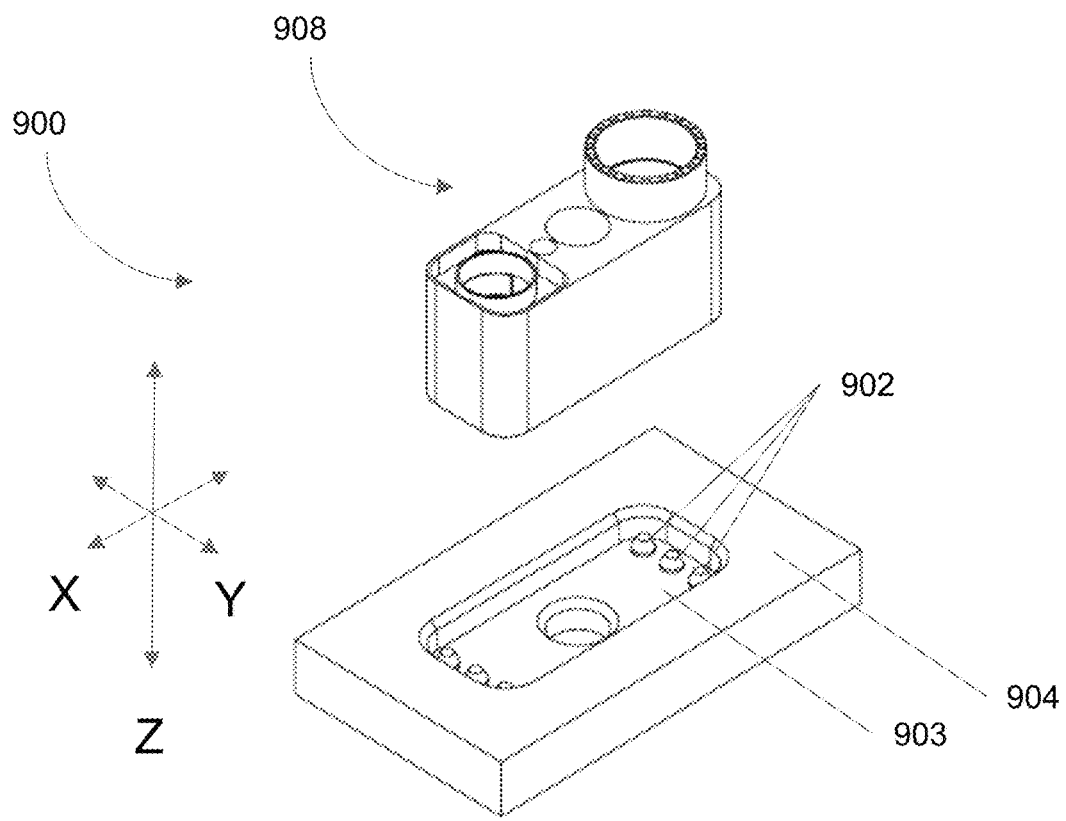

FIG. 13B illustrates an enlarged exploded view of the cross-sectional view 900 depicted in FIG. 13A. As can be seen from FIG. 13B, a detachable specimen 908 (for example a discrete imaging pod or discrete bioreactor unit similar to as shown in FIG. 12 or other figures through the present disclosure) can engage with and be fixtured to a substrate 904 (or a recess within the substrate) through the tapered-post fixturing system. As is apparent from the present disclosure, a substrate 904 can be configured for a single detachable specimen 908 (or discrete imaging pod), or the substrate 904 can be a surface of another aspect of bioreactor systems as described herein, such as a surface of a base container of a cassette-based multi-well system described above, an embodiment of which being depicted in FIGS. 11 and 12 and further described above. The posts 902 can extend upward from a surface 903 that is configured to receive the detachable specimen 908.

Covers for Microscopy Enabled Perfusion Plates

Standard multiwell plates use a clear lid in order to keep debris out of the wells and to allow for the transport of plates outside of an incubated or sterile space.

The culture imaging plates of bioreactor systems as described herein require the same type of system, but it must be altered due to the geometry of the plate and its uses. The covers used on the imaging plates of bioreactor systems as described herein can contain an optically transparent (such as a clear optically transparent) window for viewing aspects of the system, for example the feed well and the imaging well. This opening can also allow for light to pass through the main well for viewing on a standard microscope.

Covers as described herein can also contain an opening over media collection chamber, for the pressure actuation screw or other vacuum source, so that the screw can be accessed and utilized without the removal of the cover. The cover can also have space in between the plate and the cover that does not allow the cover to seal against the plate. This ensures adequate gas exchange, air flow, and humidity when in an incubated environment. The cover dramatically reduces evaporation in imaging plate may experience.

The covers can be labeled to easily identify the experiment. Lids can also be color coded to indicate the contents of the plate. A white lid, for example, can indicate a plate with no biomaterials. A black lid, for example, indicates a plate containing biomaterials. A red lid, for example, can indicate a plate that has been dosed with a drug or other carcinogenic substance. One of skill in the art would understand that any colors or combination of colors can be used to color-code lids according to the needs and desires of a user.

Figure 14A:
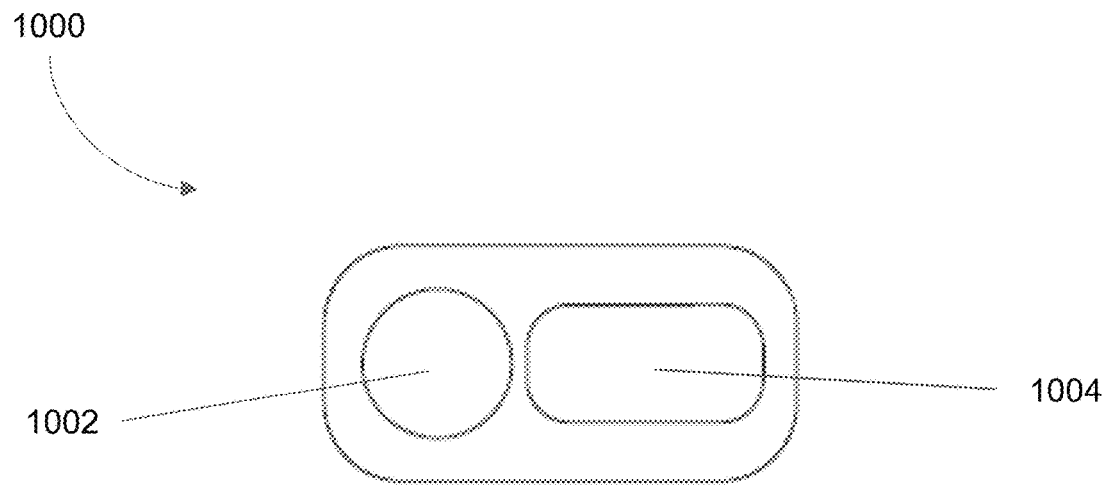
FIGS. 14A-14B depict an embodiment of covers for aspects of bioreactor systems as described herein. Such covers can have an optical viewing window and can be color-coded.
Figure 14B:
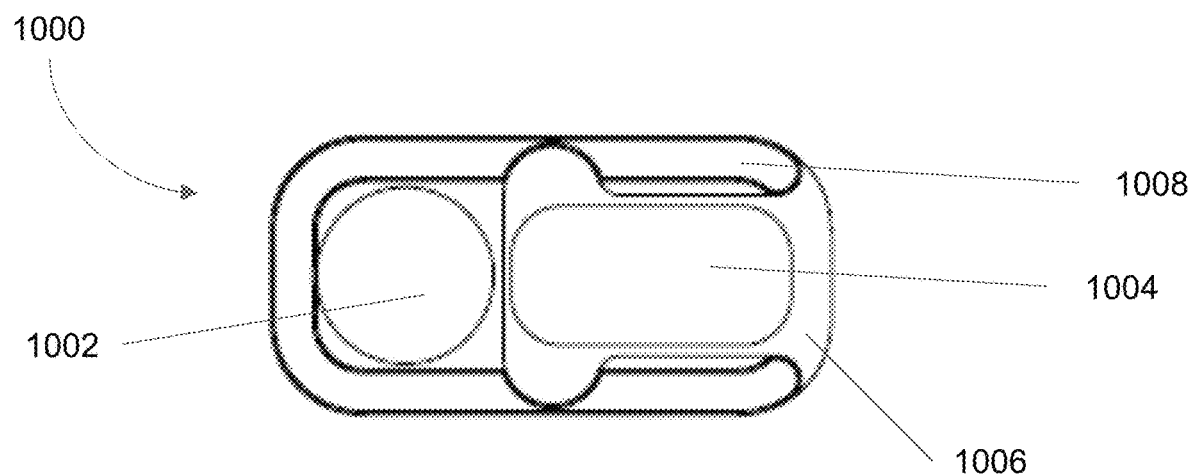

FIGS. 14A and 14B illustrate a top view and a bottom view of an embodiment of a cover 1000 for an aspect of a bioreactor system as described herein, for example the discrete imaging pods as shown at least in FIGS. 11-13. FIG. 14A depicts a top view of a cover 1000 for an aspect of a bioreactor system as described herein. As can be seen from the top view, the cover 1000 contains a hole 1002 that functions as an access source for the vacuum source, for example the actuation screw. As also shown in FIG. 14A, the cover 1000 has an optically transparent viewing window 1004, allowing a user to visualize aspects of the interior of the system, for example the culturing chamber, the liquid reservoir, or both.

The bottom of an embodiment of a cover 1000 as described herein is shown in FIG. 14B. As can be seen in the bottom view of FIG. 14B, a hole 1002 exists for the user to access the vacuum source, as well as an optically transparent viewing window 1004. The bottom of the cover 1000 can have a recess configured to fit and hold an optically transparent material 1006 for the viewing window, for example a glass microscope cover slide. The optically transparent material 1006 of the viewing window 1004 can be affixed to the surface of the cover.

Without intending to be limiting, the optically transparent material or device can be, for example, glass coverslips of size 0 or 1, and can be 9 mm×22 mm, but different embodiments of the design can use different external dimensions as one of skill in the art would appreciate. The optically transparent material can be very thin to maintain suitable image clarity.

They are affixed using optical glue around the edges to seal it and hold it in place.

As can be seen in the bottom view of FIG. 14B, the cover 1000 can also contain a lip 1008 extending downward from the bottom that is configured to abut the outer surface[s] of aspects of bioreactor systems as described herein, for example discrete imaging pods as shown in FIGS. 11-13 and as described above.

Figure 15A:
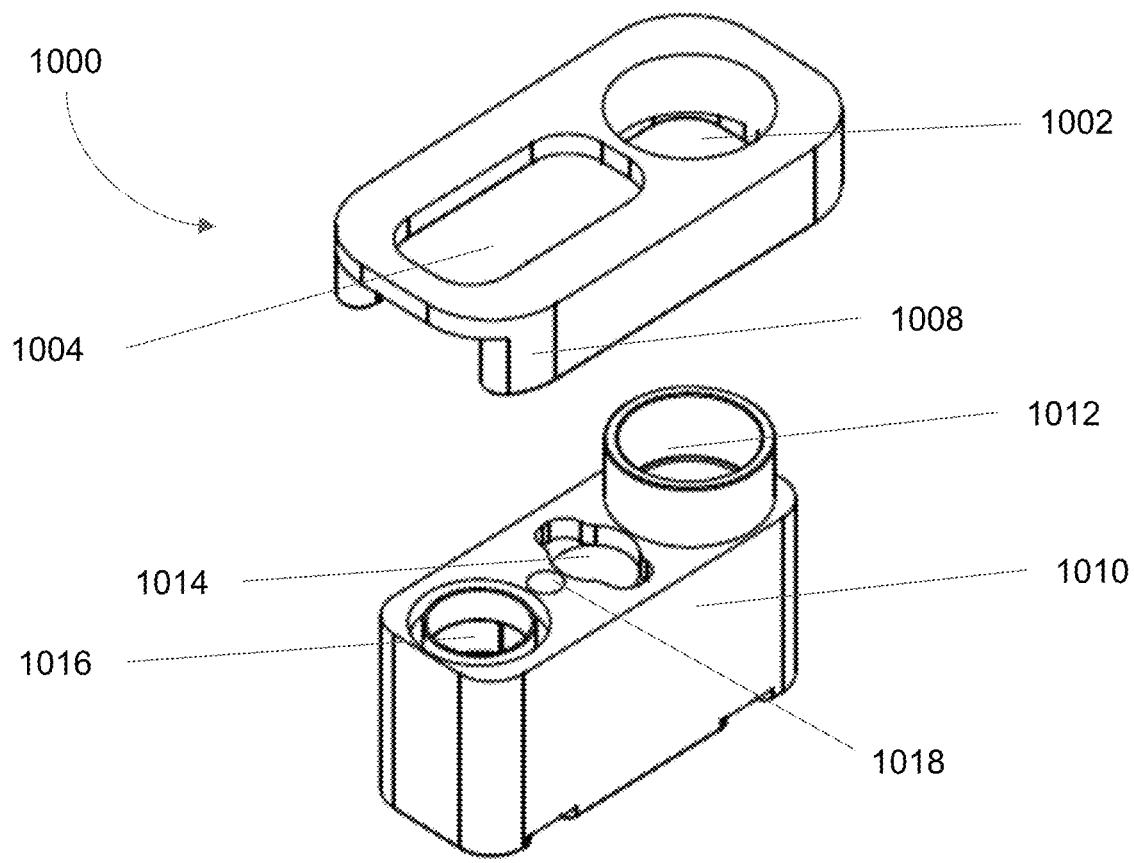
FIGS. 15A-15B depict an exploded (FIG. 15A) and assembled (FIG. 15B) view of an embodiment of an aspect of bioreactor systems as described herein.
Figure 15B:
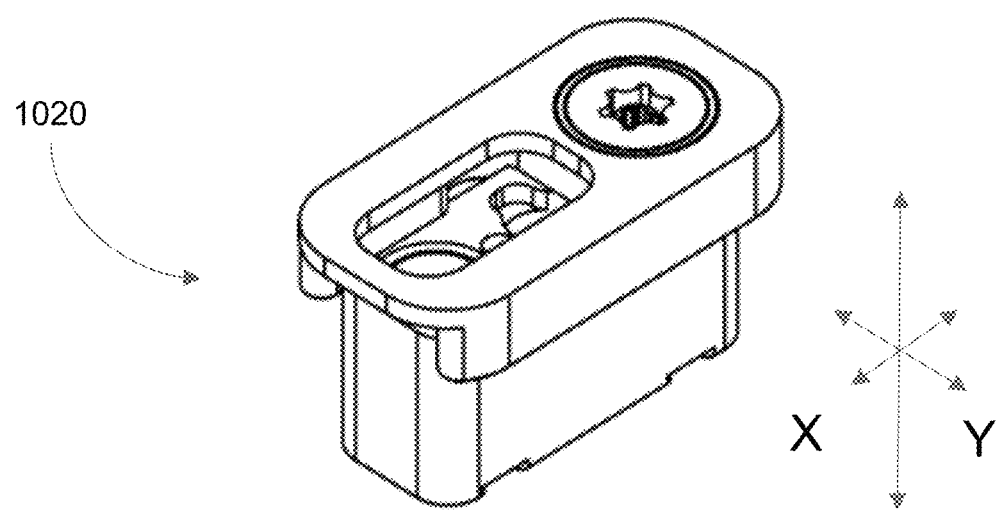

Additional aspects of embodiments of covers and imaging aspects of bioreactor systems as described herein are shown in FIGS. 15A and 15B. FIG. 15A depicts an exploded view of an embodiment of a discrete imaging pod 1010 and a cover 1000 that is configured to mate with such.

As can be seen in the exploded view of FIG. 15B, the cover 1000 has a window 1002, optical viewing window 1004, and a lip 1008. The lip is configured to mate with the imaging pod 1010 so that the vacuum apparatus assembly of the media collection well 1012 fits into the window 1002 of the cover 1000 when assembled. The viewing window 1004 of the cover 1000 allows visual inspection of the liquid reservoir 1016, injection port 1018, and/or culture well 1014 of the imaging pod 1010. The lip 1008 of the cover 1000 is configured to snugly abut the side of the imaging pod so that the cover 1000 is constraining by the lip 1008 in the x-axis, y-axis, or both when assembled with or mated to the imaging pod 1010.

FIG. 15B depicts a cover assembled with the discrete imaging pod of FIG. 15A, and shows an embodiment of an assembled discrete imaging pod 1020 according to the present disclosure.

Injection Port for Drug Delivery

When testing a drug (something which has a biological effect on a biological sample, which can have a known structure such as small molecules, proteins, nucleic acids, and the like) on biological sample under standard culture conditions, a known amount of a drug is added to known volume of liquid, so dosing can be consistent and controlled. In a well plate perfusion system, cell growth media is constantly circulated, so the amount of growth media per well at a time point is not as well known. In addition, larger volumes of the drug must be used to achieve the correct concentration within the well. Therefore, adding a known amount of drug to an unknown amount of growth media can lead to inconsistent dosing and can be expensive.

Aspects of the present disclosure proposes a solution by supplying a small amount of a drug of a known concentration directly to the biological sample being dosed through a drug injection port. The injection port is positioned in a flow path from liquid reservoir to culture chamber to media collection chamber in-between the liquid reservoir and the culture chamber, in order to ensure that the sample in the culture chamber directly receives the desired dose, and the only sample that receives the drug is the sample directly downstream from the injection port.

Aspects of the present disclosure describes a small port that is connected to the flow channel through which liquid is perfused through the system. This port is a known volume in which a drug of a known concentration can be injected. This then allows a desired drug dosage to be delivered to the biological sample. The feeder well (also referred to herein as liquid reservoir) for the system can additionally be plugged, enabling the injection port to be the only well supplying liquid to the perfusion system. Novel elements include the ability to more accurately dose biological samples by removing the uncertainty associated with adding drugs to an unknown volume of perfusion media. Aspects of the present disclosure also allows for the drugs to be delivered more quickly to the biological sample depending on the placement of the port relative to the perfusion channel. Aspects of the present disclosure also allows a smaller volume of drug to be used since it is applied directly instead of a larger volume being added to the feeding well.

Aspects of the present disclosure would allow users to more accurately and efficiently dose biological samples within perfusion systems. Aspects of the present disclosure is also cost effective, allowing users to use smaller volumes of a drug while achieving desired results.

Figure 16:
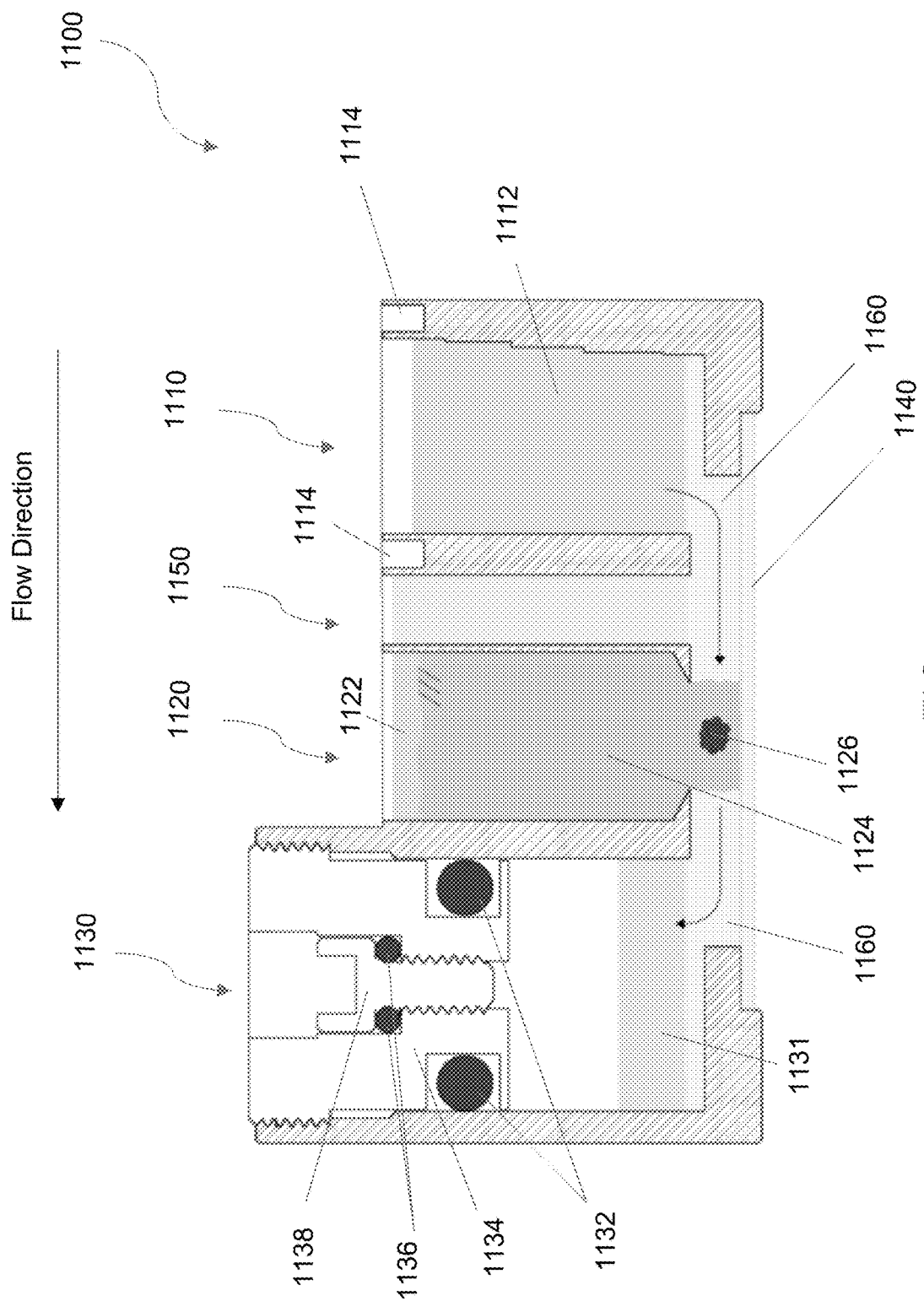
FIG. 16 illustrates a cross-sectional view of an embodiment of an aspect of bioreactor systems as described herein. In particular, the cross-section of FIG. 16 depicts an optional injection port which can be used to controllably and precisely deliver drugs (small-molecules, proteins, polymers, nucleic acids, and the like) to a flow path of the bioreactor, and thereby deliver the drugs to cells cultured within the bioreactor.

FIG. 16 shows a cross-section of a discrete imaging or bioreactor pod having incorporating the injection port as described herein. In certain aspects, the injection port can be configured for a volume of about 40 to about 80 μL. In certain aspects, the injection port can have an aperture for injection of the drug with a diameter of about 1 to about 3 mm in order to combat undesirable effects of capillary action.

As shown in the cross-sectional view of FIG. 16, the injection port 1150 is directly upstream in regards to the flow direction with biological sample 1126 in the culture chamber 1120 in a horizontal perfusion flow path of media 1112 through a hydrogel filter media 1160 comprising perfusion from a liquid reservoir 1110 to the injection port 1150 to the culture chamber 1120 to the media collection reservoir 1130.

Additional aspects of bioreactor systems as described herein can be seen in the cross-sectional view of the embodiment of FIG. 16. A substantially annular overflow reservoir 1114 can surround the upper portion of the liquid reservoir 1110 for the overflow of media 1112. An optically transparent material 1140 can form the bottom of the bioreactor system so as to enable the system to be microscopy-enabled. The culture chamber 1120 houses the 3D growth media (also referred to as the liquid-like solid or LLS) 1124 in which the biological sample 1126 is cultured. Media 1122 can also be placed in the culture chamber 1120.

The media collection chamber 1130 can house the vacuum source apparatus, or the apparatus which creates positive or negative pressure throughout the system. In the embodiment shown in FIG. 16, pressure is created by a screw-driven actuator. The embodiment of the screw-driven actuator as shown comprises an outer screw 1134 that creates pressure to drive fluid flow throughout the system, and an inner screw 1138 which acts as a pressure relief screw. The vacuum source apparatus can be operably connected to the media collection chamber through a combination of threads on the outer surface of the screw 1134 and the surface of the media collection chamber, and a series of gaskets, such as the outer gasket 1132 and inner gasket 1136 as shown.

The embodiment of FIG. 16 illustrates an embodiment of a bioreactor system having a horizontal flow path. In the embodiment of FIG. 16, the screw is turned so as to generate negative pressure in the system. Negative pressure draws the media 1112 from the liquid reservoir 1110 into the hydrogel filter media 1160 towards the biological sample 1126 in the 3D growth media 1124 of the culture chamber 1120. Any drugs or substances placed in the injection port 1150 will enter the perfusion flow stream on the way from the liquid media reservoir 1110 to the biological sample 1126. Effluent waste 1131 is then drawn from the culture chamber 1120 through the hydrogel media 1160 and into the media collection chamber 1130, where it can be removed with vacuum suction or manual pipetting (after detaching the vacuum source apparatus).

Additional aspects of microscopy-enabled bioreactor systems are described herein. Such additional aspects can allow for the horizontal perfusion of liquids through a single imaging well system, comprised of a feed well (also referred to herein as a liquid reservoir), a printing well with a viewport for imaging (also referred to herein as a culture well), and an effluent collection chamber (also referred to herein as a media collection chamber). Each of these components can be connected using a porous gel filter system, where the gel has a higher permeability and pore size than the LLS used in the printing well. This allows for liquids to be perfused through the gel filter and through the LLS, while not allowing the larger particles of LLS to pass through the filter.

Some of the additional aspects as described herein include an LLS "shelf" and acrylamide plug for greater gas exchange. This shelf was added to the interior of the printing well, where the LLS would be filled up to the shelf and the plug added on top. In the previous design, the LLS had to be filled nearly to the top of the printing well in order to ensure that the system would take the path of least resistance of flow, which would be from the media well, not from above the LLS. This tall column of LLS is undesirable for gas exchange. This plug accomplishes the same functional aspects, allowing the negative pressure chamber to cause perfusion across the LLS from the media well without affecting the height of the LLS and allows for greater gas exchange in the system. By adding the plug, the pressure in the printing well will equilibrate and liquid will flow along the desired path.

Other additional aspects include changes to the method of actuation in the negative pressure chamber. In an embodiment, a set screw was actuated in order to create a negative pressure, and the threads were used as both a method of mechanical actuation and for sealing. This functional design includes a screw that has threads for the method of mechanical actuation but has an o-ring embedded that acts as the sealing mechanism. The o-ring allows for a piston-like seal, moving up and down along the walls of the negative pressure chamber. This screw also has a pressure relief screw inlayed inside the allen key interface, which also incorporates an o-ring as the sealing mechanism. This pressure relief screw is removed before resetting the main screw to avoid backpressure and resistance in the system. It can also be used as a port to remove liquid effluent from the effluent chamber. The plate also includes markings near the screw to allow the user to track the number of rotations or partial rotations performed with the screw. Other embodiments can include the use of a self-healing annular seal (such as the seals of common blood collection tubes) instead of a screw, which can be pierced by a blunt needle, have a vacuum pulled, and then remove the needle from the system. After the needle is removed, the system re-seals itself. Vacuum can be pulled using this method as many times as necessary during the use of the system.

In regards to the feeder well, the well can include tier markings to allow the user to view the volume of media left in the well. This well has the capability to be plugged to allow flow from other chambers. Surrounding the well is an overflow reservoir. This collects and media that spills out of the feeder well when it is being plugged. The design can also incorporate a drug port, which is detailed further above. The drug port is connected to the same gel filter channel that the feeder well is connected to. When the feeder well is plugged, the system starts pulling liquid from the drug port. This drug port allows for small amounts of drug or labels to be perfused through the system independently of the feeder well. This reduces the amount of drug necessary to be delivered through the system since it does not have to be diluted into the feeder well.

In regards to the gel filter channel, a labyrinth in the channel can lengthen the overall length that the liquid has to travel during perfusion and to help anchor the gel filter in place and keep it from moving. By lengthening the distance that the liquid has to flow, LLS particles are more likely to be caught in the filter and not be able to perfuse, thereby only allowing liquid to be perfused through the system.

The present disclosure will enable real-time, non-invasive, in situ imaging of live biological tissues grown in 3D, living to in situ lifespans greater than seen before.

Existing in situ imaging of 3D cellular arrays exists as static environments; this leads to early cell death and limited cellular lifetime analysis. By using embodiments of the present disclosure, not only will researchers be able to directly observe the cells undergoing whatever process is occurring as they could previously, they will be able to observe them into time scales greater than ever before, all without ever touching the cells after placing them in their growth environment.

Figure 17:
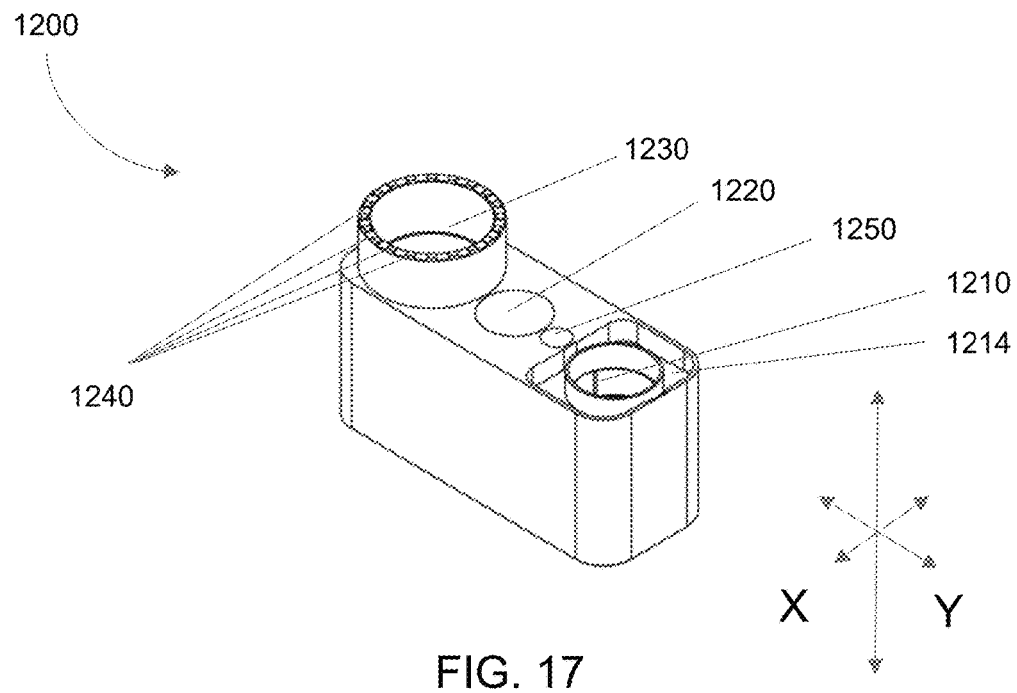
FIG. 17 depicts an embodiment of an aspect of a bioreactor system as described herein, in particular showing an optional media overflow well surrounding and abutting the outer diameter of the liquid reservoir and configured to catch and hold excess liquid from the liquid reservoir.

Such additional aspects can be seen in the figures. FIG. 17 depicts a perspective view of an aspect of a bioreactor system 1200 as described herein, which can be a discrete imaging pod or bioreactor unit. As can be seen, the port for screw-driven actuation can contain visual tick marks 1240, giving the user an indication of how much the screw is being turned. The injection port 1250 can also be seen in the top, as can the overflow well of the liquid reservoir 1214 (or feed well), which surrounds the outer diameter of the liquid reservoir 1210 and is configured to catch and hold overflow, in particular when the feed well is plugged. The culture chamber 1220 is also visible.

Figure 18:
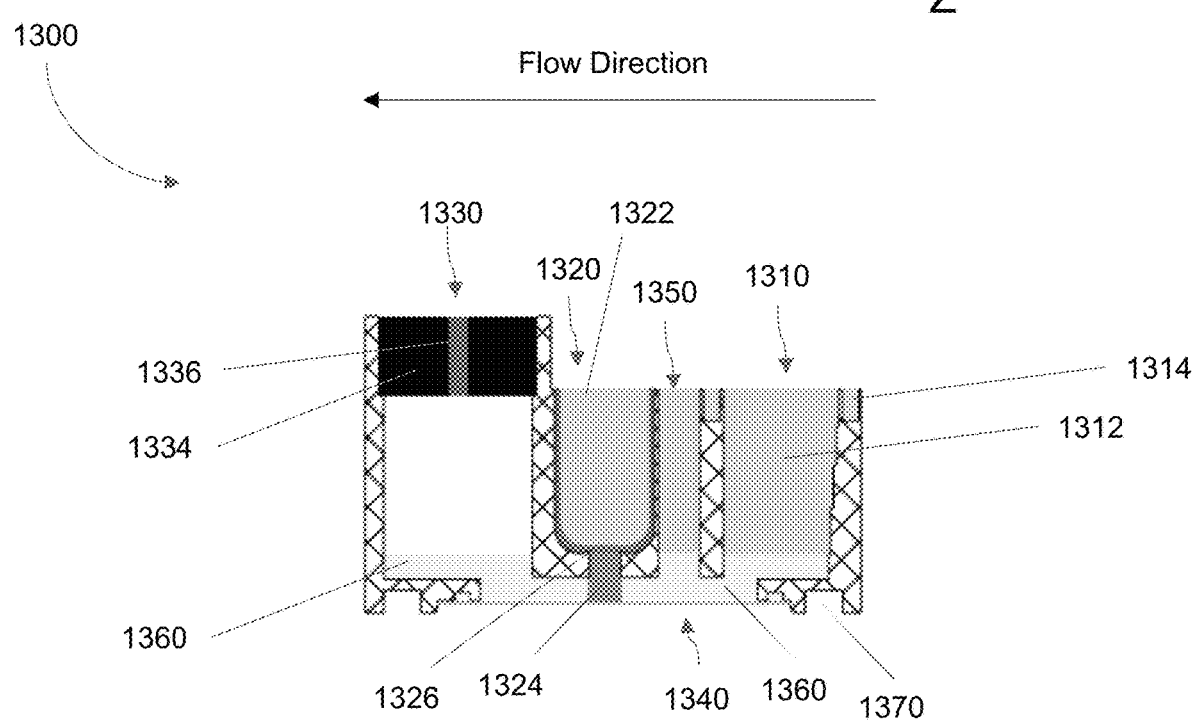
FIG. 18 depicts an embodiment of an aspect of a bioreactor system as described herein. As can be seen from the embodiment of FIG. 18, a self-healing annular seal can be used in the system in lieu of other pressure-delivery apparatuses as described herein (for example a screw driven actuator).

FIG. 18 depicts a cross-sectional view of an embodiment according to the present disclosure, illustrating a self-healing annular seal 1334 in place of a screw-driven actuator. Such self-healing annular seal 1334 can be punctured by a needle, for example at the position 1336, and pressure withdrawn or applied from/to the system accordingly. Like the embodiment of FIG. 16, the embodiment of FIG. 18 shows a liquid reservoir 1310 (with overflow well 1314), an injection port 1350, a culture chamber 1320, and a media collection chamber 1330.

The application of negative pressure draws fluid 1312 in a horizontal perfusion flow path from the liquid reservoir 1310, through the hydrogel media 1360, and towards the 3D growth media or LLS 1324 in which a biological sample would be housed. Any substance in the injection port 1350 would also be drawn into the perfusion stream. Liquid effluent waste can then be drawn from the culture chamber 1320 and the growth media 1324 through the hydrogel filter 1360 and into the media collection chamber 1330.

The embodiment of FIG. 18 also depicts a hydrogel "shelf" where the 3D growth media is firmly held into place as it is plated into a void of the hydrogel filter 1360. A plug 1326 can also line at least a portion of the culture chamber 1320 that is in fluid communication with the 3D growth media 1324.

Figure 19A:
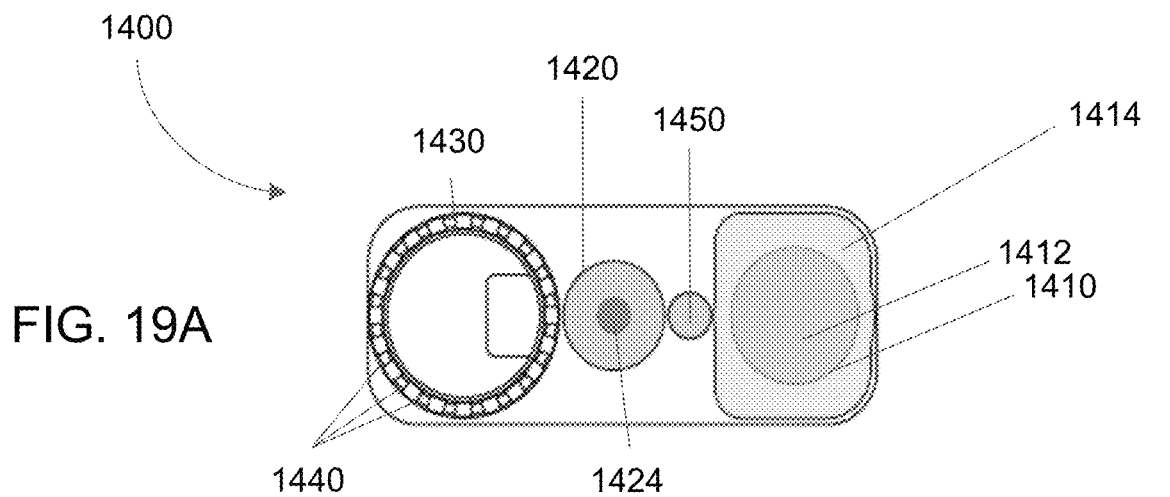
FIGS. 19A-19B depict another embodiment of an aspect of bioreactor systems as described herein.
Figure 19B:
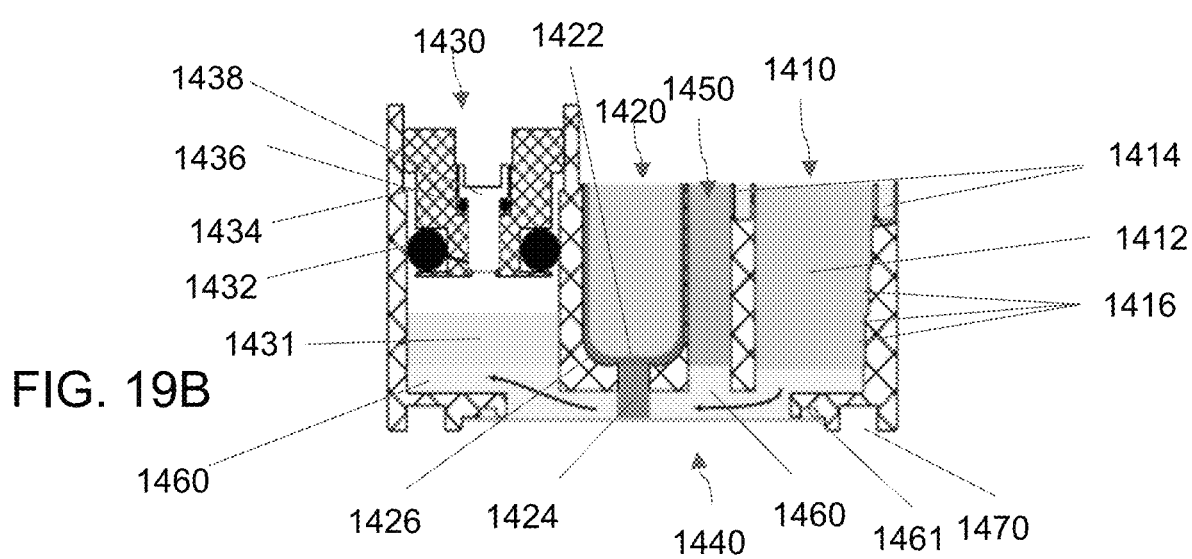
Figure 19C:
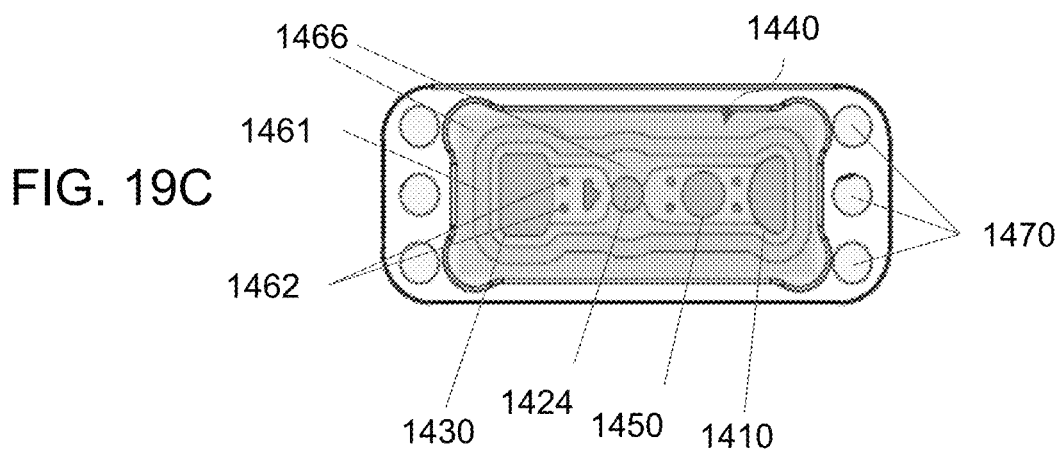

FIGS. 19A-19C depict additional aspect of systems as described herein. FIG. 19A depicts a top view of the embodiment of FIG. 17. Rotation tick marks 1440 for the screw-driven actuator can be seen, in addition to an overflow well 1414 for overflown media from the liquid feed well 1410. An injection port 1450 can also be visualized from this view, in addition to the culture chamber 1420 housing the 3D growth media 1424.

FIG. 19B is a cross-sectional view of an embodiment as described herein. As can be seen in the embodiment of FIG. 19B, the screw driven actuator can further comprise a pressure relieve set screw 1448 seated in the center of the actuation screw 1444 to relieve pressure (operably connected to the media collection chamber by gaskets 1442 and 1446). A plug 1422, which can be an acrylamide plug, can line the culture chamber 1420 and abut the 3D culture media 1424 seated in the system 1400, to improve functional characteristics of the system as described above. Volume tick marks 1414 can also be seen on the inner surfaces of the wells, providing the user a simple and easy visual indication of liquid volume within the wells. Additional aspects of the embodiment of the system can be seen in FIG. 19B. Recesses 1470 that are configured to receive posts of a repeatable position system are shown, as is the glue channel 1461 comprising glue for securing the bottom 1440 to the system (the bottom 1440 can be an optically transparent bottom.

A horizontal perfusion flow path is also shown. The application of negative pressure draws fluid 1314 in a horizontal perfusion flow path from the liquid reservoir

1410, through the hydrogel media 1460, and towards the 3D growth media or LLS 1424 in which a biological sample would be housed. Any substance in the injection port 1450 would also be drawn into the perfusion stream. Liquid effluent waste 1431 can then be drawn from the culture chamber 1420 and the growth media 1424 through the hydrogel filter 1340 and into the media collection chamber 1430.

FIG. 19C illustrates a bottom view of an embodiment according to the present disclosure. In the embodiment of FIG. 19C, an optically transparent glass coverslip 1440 (although other materials may be used) is affixed to the bottom by a glue in a channel 1461 to allow imaging via microscopy. Examples of glue that can be used can be Optical glue (UV cured). Biocompatible epoxies. Any glue that can resist both water and mild heat, as well as not being a biocide. Mechanical immobilizers 1462 are present comprising vertical posts spaced throughout the hydrogel volume 1460, similar to rebar in concrete. The recesses 1470 for the posts of the repeatable positioning system can also be seen, in addition to the liquid reservoir 1410, injection port 1450, 3D growth media 1424, and media collection chamber 1430. The glue surface 1466 is also shown.

Microscopy Enabled Dual Flow Bio-Reactor Plate

In traditional 2D cell culture, cells often behave differently than they do within the human body. Different methods of 3D culture have been developed in order to more closely mimic the conditions that cells typically experience. Most of these systems involve the use of matrigel, which locks cells in place in 3D and does not allow for much movement of the cells or nutrients within the system. This can hinder long term studies due to the lack of long term viability in these systems. In order for cells to survive for extended periods of time in a 3D culture system, nutrients must be replaced and the waste produced by the cells must be removed. The following aspects provide a way to promote long term cell viability in 3D culture as well as a way to study them in a high throughput system.

Aspects of the present embodiment describe a microscopy enabled dual flow bioreactor system in which two separate perfusive flows are used to supply nutrients to and remove waste from the cells and their surroundings. The perfusive flows are perpendicular (orthogonal to one another) and separated in height from each other to ensure there is not any cross flows within the imaging well (also referred to as the culture well). This allows for the co-culture of two cell types, each with their own distinct growth media. Each cell type is placed in the stream of its respective media to ensure nutrient delivery without being in the flow of the other cells media. This allows for the sustained, long term growth of two different cell types in close proximity to each other.

The flow is perfused through a "liquid like solid", or LLS, which is a porous support medium in which cells can be cultured. This LLS allows for liquids such as cell growth media to be perfused through the system in order to feed the cells and remove their waste. The liquid is forced to perfuse using a passive negative pressure system, pulling liquid through the LLS and the whole system itself. In this system, cell survivability extends to several months as opposed to days or weeks in other cell culture systems.

Aspects of the present embodiment can include the main plate, two pressure actuation screws, and two pressure relief screws with accompanying o-rings. A hydrogel filter with a pore size of one micron can be used as a filter to prohibit the LLS from moving within the LLS chamber. This can allow for the LLS to stay in place which allows for the liquid growth media to flow through the LLS particles, supplying the cells with nutrients and removing waste. The pores are smaller than the size of the LLS particles, allowing the filter to support the LLS in the well plate while allowing liquid to move past it into the effluent collection chamber. The plate also includes an overflow reservoir around each feed well and individual injection ports for each cell type. The injection ports are used to quickly perfuse low quantities of precious reagent. The volume is much lower than that of the feed well, but is in the direct path of perfusion flow. So ensure flow of the injection port, the feed well is plugged to force the perfusion to favor the injection port liquid. In plugging the feed well, some overflow is to be expected, so an overflow reservoir is added to each feed well to prohibit contamination and minimize cleanup.

Each feed well can contain steps machined along the length of the well that serve as a visual reference for the amount of growth media. Each steps can be equivalent to 100 microliters worth of volume. The plate utilizes a mechanical hydrogel locking system to prevent the hydrogel from compressing or moving when the vacuum is applied to the system. The mechanical hydrogel locking system includes of a series of obstacles machined into the channel in which the flow travels.

The microscopy enabled dual flow bioreactor system can feature six female tapered posts machined into the bottom of the plate. The recesses mate with the matching male to mechanically over-constrain the system into alignment. This allows for highly repeatable placements of the plate. This can prove to be very advantageous with long term microscopy. The user can image the plate and return it to an incubator and then reimage the plate at a later time and have very little placement error. This allows the user to gather multiple images over days without having to take a continuous time lapse. The placement is precise enough to where the same construct can be easily located and adjusted to composite images or videos.

Initially, a set screw can be actuated in order to create a negative pressure, and the threads were used as both a method of mechanical actuation and for sealing. The design includes a screw that has threads for the method of mechanical actuation but has an o-ring embedded that acts as the sealing mechanism. The o-ring allows for a piston-like seal, moving up and down along the walls of the negative pressure chamber. This screw also has a pressure relief screw inlayed inside the torx key interface, which also incorporates an o-ring as the sealing mechanism. This pressure relief screw is removed before resetting the main screw to avoid backpressure and resistance in the system. It can also be used as a port to remove liquid effluent from the effluent chamber. The plate also includes markings near the screw to allow the user to track the number of rotations or partial rotations performed with the screw.

The plate can also include a self-healing annular seal. The self-healing annular seal is punctured by a blunt needle on a syringe, vacuum is pulled in the syringe, and the needle is removed. The seal "selfheals" and holds in the vacuum. A syringe could be modified to accept a vacuum gage. This would allow the user to precisely actuate the desired pressure. This gage also serves as a leak checker as when the syringe is reinserted, the gage will read the vacuum pressure present in the plate. A separate syringe could also be used to collect the accumulated effluent for analysis. In testing the self-healing annular seal has proven to be a more ergonomic solution to vacuum generation that the screw assembly.

Aspects of the present disclosure include the ability to grow two different cell types in a more life-like environment and keep them viable for much longer periods of time than previously possible. In this plate each cell type is supplied its specific growth media and perfusion delivery is independent for each cell type. This allows for long term experimentation as well as analysis of the interactions of the two cell types in 3D. This process can be easily documented on a microscope or other optical forms of analysis.

Aspects of the present disclosure include a method to culture 2 different cell types in 3D under perfusion that is able to viewed at all stages on a microscope. This can be advantageous to any user that desires to complete experiments using this method. Aspects of the present disclosure has created a method to culture 2 different cell types in 3D under perfusion that is able to viewed at all stages on a microscope. This allows the user to track a single cell throughout the life of the experiment. The user can add two different cell types and see the interactions between the two cells types while still keeping the cell types alive using independent growth medias. Not only does the plate allow these two different cell types to be imaged in 3D, but it allows the cell types to live for much longer without the need for passaging.

A number of embodiments of the present disclosure have been described, which can include the functions of one or more of: two channels at different levels provided independent perfusion; different cell types are printed in the LLS chamber at different heights; separate medias and flow rates can be used; all cell constructs placed within 2 mm of glass.

Figure 20:
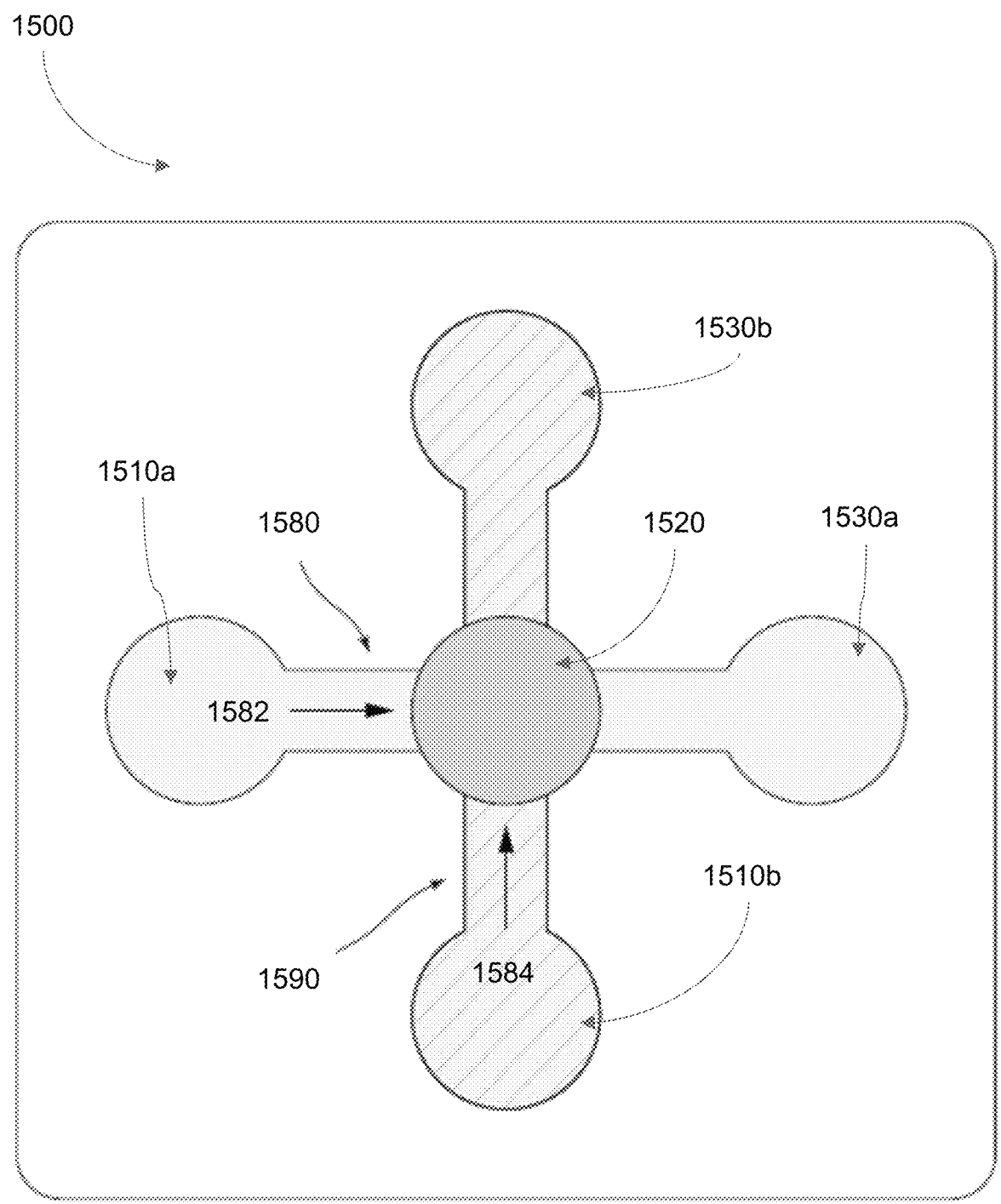
FIG. 20 is another embodiment of an aspect of a bioreactor system as described herein, illustrating two orthogonally opposed flow paths interesting in the common culture chamber shared between the flow paths and positioned in the middle of each flow path.

FIG. 20 illustrates as a top view of aspects of the embodiment of the dual-flow system 1500 as described herein. The system 1500 can comprise two flow paths, a first flow path 1582 (type 1) and a second flow path 1584 (type 2). The two flow paths are perpendicular or orthogonal to one another, and share a common culture chamber 1520 (also referred to herein as a culture chamber, imaging chamber or LLS chamber). This common culture chamber is also the point of intersection for the flow paths. Each of the flow paths 1582 and 1584 is at a different height so that there is not a physical intersection or combination of the flows. This allows for the interaction of cells within the column of LLS media, without cross-intersection of flows bound for one cell type to another cell type, which can be accomplished with the appropriate operating parameters (such as a flow rate of about 10 nm/s to about 1 mm/s).

As shown in FIG. 20, a perfusion flow path of the first flow path 1582 comprises flow of fluid from a liquid reservoir 1510a through a channel 1580, into a culture chamber 1520 and into a media collection chamber 1530a. A perfusion flow path of the second flow path 1584 comprises flow of fluid from a liquid reservoir 1510b through a channel 1590, into a culture chamber 1520 (that is the same as for the first flow path) and into a media collection chamber 1530b.

FIG. 21 is a cross-section of a perspective view 1600 of the culture chamber 1520 of the dual-flow system described herein and as shown in FIG. 20. As can be seen in the cross-sectional view 1600, two orthogonal perfusion streams (1582 and 1584) flow through a LLS column 1524 immobilized in a hydrogel filter 1560 (a 3D hydrogel) of the culture chamber 1520 at different heights Z relative to the bottom of the chamber 1540, feeding two distinct populations of cells 1526 and 1527. Although the flow paths are illustrated as orthogonal to one another, one of skill in the art would recognize that other angles can be employed.

Figure 22:
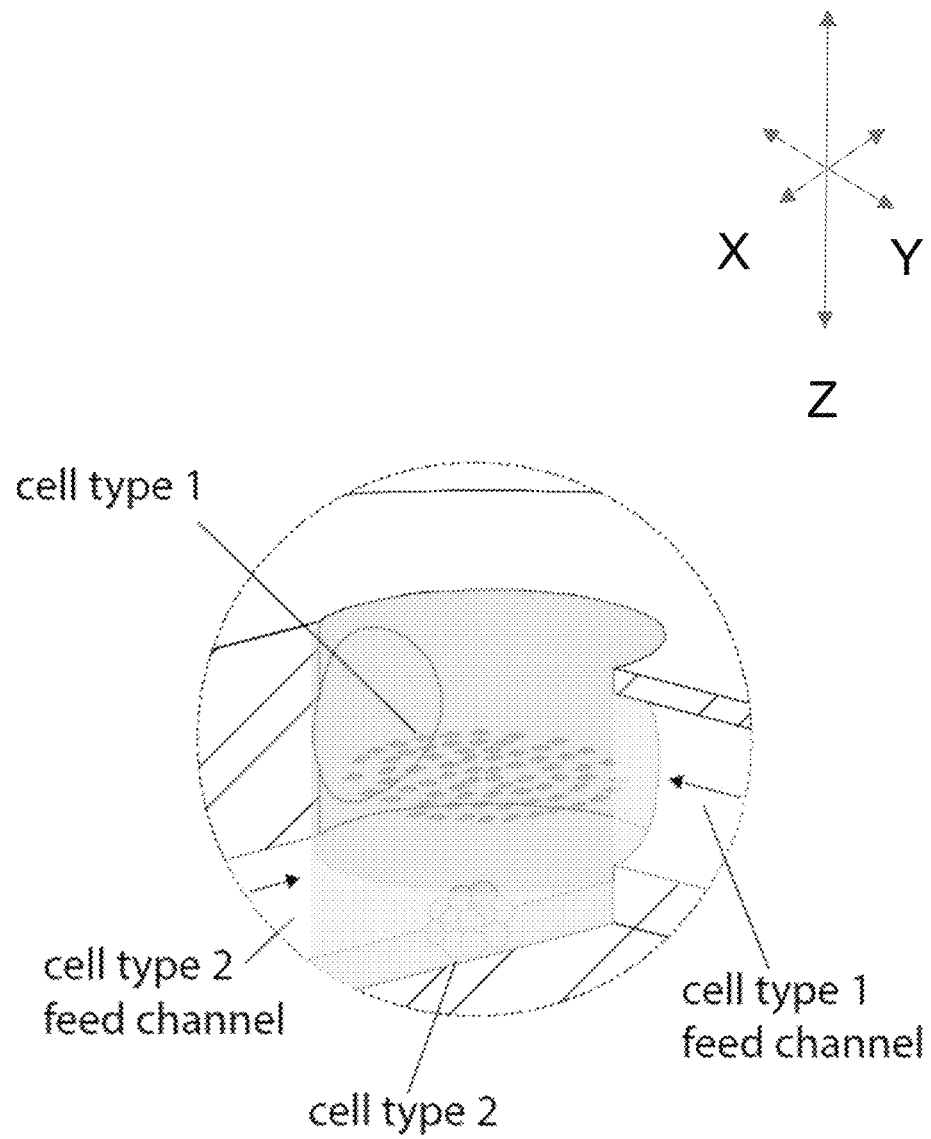
FIG. 22 is another cross-sectional depiction of the culture chamber (LLS chamber) of the embodiment of the aspect of the bioreactor system having dual flow paths.

FIG. 22 is an enlarged cross-sectional view of the LLS column of the LLS chamber as shown in FIGS. 21 and 22. As can be seen in FIG. 22, two orthogonal perfusion streams are perfused through the LLS column at different heights, feeding two distinct populations of cells printed at different heights in the LLS column of the LLS chamber of the dual-flow system.

FIGS. 23A-23D illustrate an embodiment of a dual-reactor flow system as described herein. FIG. 23A is a perspective view, FIG. 23B is a top view, FIG. 23C is a side view, and FIG. 23D is a bottom view.

As can be seen in the perspective view of the embodiment of a dual-flow bioreactor system as described herein, two flow paths are disposed orthogonally to one another. One flow path comprises a liquid reservoir 1710a, overflow well 1714a, culture chamber 1720, drug injection port 1750, and media collection chamber 1730a. A second flow path comprises a liquid reservoir 1710b, overflow well 1714b, culture chamber 1720, drug injection port 1750, and media collection chamber 1730b. Both flow paths share the same culture chamber, and cells for each flow path (which can be different types of cells—one type for one flow path, another type for another flow path) can be disposed in the culture chamber as shown in FIGS. 21 and 22.

FIG. 23B is a top view of the dual-flow bioreactor 1700 as shown in FIG. 23A. FIG. 23C is a side view of the dual-flow bioreactor 1700 as shown in FIG. 23A. FIG. 23D is a bottom view of the dual-flow bioreactor 1700 as shown in FIG. 23A. As can be seen in the bottom view, the embodiment of the dual-flow bioreactor can contain similar features as what is shown in the embodiment of a single flow bioreactor in FIG. 19C. Recesses 1770 are shown which help anchor the foam filter.

FIGS. 24A-24C illustrate other aspects of an embodiment of a dual flow bioreactor system 1800, for example visual tick marks and the actuation and relief screws. FIG. 24A is a top view, and FIGS. 24B and 24C are side cross-sectional views from different sides than one another.

FIG. 24A is a perspective view of an embodiment 1800 showing a flow path A and a flow path B orthogonal to each other. Each flow path has a liquid reservoir (1810a and 1810b), a shared culture chamber 1820, and a media collection chamber 1830a and 1830b. Liquid reservoir 1830 also has an overflow well 1814a in fluidic communication with the well, although such overflow well can be optional.

FIGS. 24B and 24C show cross-sectional views of the flow paths A and B of the embodiment 1800. Both flow paths of the embodiment utilize screw-driven actuators with a pressure relief screw to create pressure to drive fluid flow throughout the system. 1832a/b, 1836a/b, and 1838a/b show aspects of the screw driven actuator. 1820 is the shared culture chamber. 1870 illustrates receiving recesses for posts of the repeatable fixture positioning system. 1850a/b illustrate drug injection ports, 1810a/b the liquid reservoirs, and 1830a/b the media collection chamber operably connected to the vacuum source apparatus (a screw-driven actuator in this embodiment. Volume tick marks can also be present in the any of the liquid wells, and the liquid wells can additionally be tapered from the opening to the base in order in order to minimize the liquid needed and improve flow, or to provide other visual indicators (for example one tapered and one not tapered indicates different flow paths).

Figure 25:
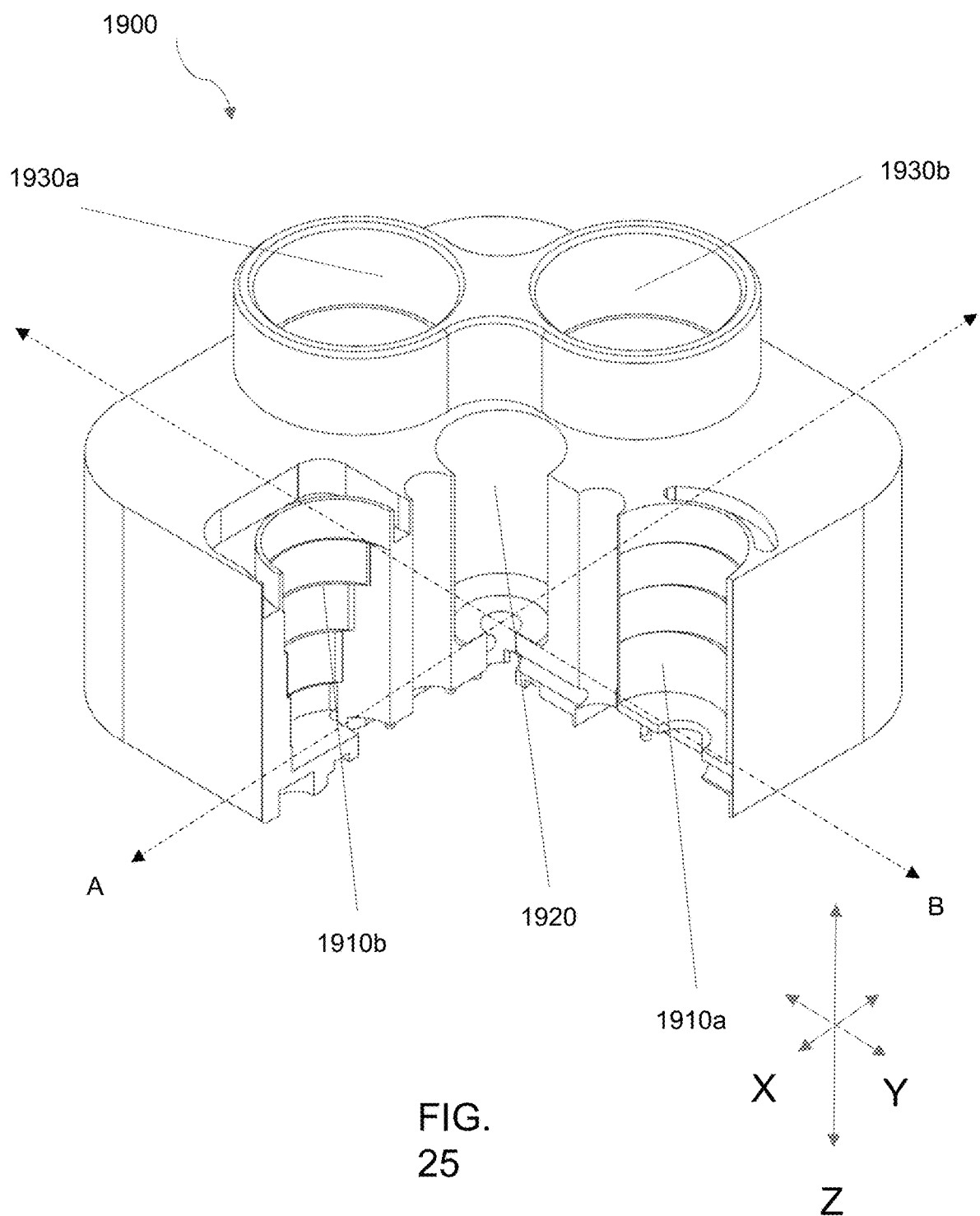
FIG. 25 is another cross-sectional view of the embodiment of FIG. 23.

FIG. 25 is an enlarged perspective view 1900 of the dual flow system of FIGS. 23A-23D. Flow paths A and B are shown, as is the shared culture chamber 1920, the liquid reservoirs 1910a/b, and media collection chambers 1930a/b.

Perfusion Enabled Multiwell Bioreactor Plate for 3D Cell Culture

In traditional 2D cell culture, cells often behave differently than they do within the human body. Different methods of 3D culture have been developed in order to more closely mimic the conditions that cells typically experience. Most of these systems involve the use of matrigel, which locks cells in place in 3D and does not allow for much movement of the cells or nutrients within the system. This can hinder long term studies due to the lack of long term viability in these systems. In order for cells to survive for extended periods of time in a 3D culture system, nutrients must be replaced and the waste produced by the cells must be removed. The following aspects provides a way to promote long term cell viability in 3D culture as well as a way to study them in a high throughput system.

Aspects of the present disclosure describe a multiwell bioreactor system in which perfusive flow is used to supply nutrients to and remove waste from the cells and their surroundings. The flow is perfused through a "liquid like solid", or LLS, which is a porous support medium in which cells can be cultured. This LLS allows for liquids such as cell growth media to be perfused through the system in order to feed the cells and remove their waste. The liquid is forced to perfuse using a passive negative pressure system, pulling liquid through the LLS and the whole system itself. In this system, cell survivability extends to several months as opposed to days or weeks in other cell culture systems.

Aspects of the present disclosure itself includes of a top plate, which serves as the well plate portion, a middle plate which acts as a sealing surface between interfaces, and a base plate which houses the necessary negative pressure that pulls liquid through the system into an effluent collection chamber. A microporous filter is sealed between the top plate and the middle plate. The pores are smaller than the size of the LLS particles, allowing the filter to support the LLS in the well plate while also allowing liquid to move past it into the effluent collection chamber. Several methods can be used to create negative pressure in the system, but the two used in this system are a screw that houses an o-ring, and a self-healing annular seal. The threads of the screw are used as a method of mechanical actuation and the o-ring seals the "piston" portion of the actuation screw. This screw is backed out to create a negative pressure in the base plate, which then creates a vacuum to pull liquid through the LLS. The self-healing annular seal is punctured by a blunt needle on a syringe, vacuum is pulled in the syringe, and the needle is removed. The seal "self-heals" and holds in the vacuum.

Aspects of the present disclosure include the ability to grow cells in a more life-like environment and keep them viable for much longer periods of time than previously possible. The plate's layout is set up to allow the use of plate readers, as the plate is designed to fit the standard dimensions of a well plate. This system can also be high throughput, allowing for many experiments to be run simultaneously within the same plate.

Products such as well plates capable of perfusion could result from aspects of the present disclosure. The plates could be designed to have many different layouts, having higher or lower throughput depending on the application. Laboratories and research facilities looking to perform long term studies on cells would be able to use aspects of the present disclosure to do so. Using the perfusive flow in the plate, researchers could study the effects of drugs and other changes to the cells environment by flowing these substances through the system.

In an embodiment of the present disclosure, a perfusion enabled multiwall plate is provided in which pressure is provided by a vacuum source detachably operably connected to the system through a self-healing annular seal. Such a mechanism not only removes the screw-driven actuator, but physically takes up less space and allows for more samples to be plated in the wells.

Additional Aspects of Perfusion Enabled Multiwell Bioreactor Plate for 3D Cell Culture Additional aspects of the perfusion-enabled multiwall plates are as follows. The first additional aspect includes the removal of the fasteners that clamp the top two plates to the base plate to seal along an o-ring. These fasteners can be omitted by using the internal vacuum pressure induced in the well plate as the force clamping the plates together. The top two plates can be assembled together as usual, using fasteners to seal the filter in between the two pieces, or the filters can be heat sealed to the plate itself, eliminating all fasteners. These top two plates are then placed on top of the base plate to prepare for assembly. The plates are compressed together, compressing the o-ring in the base plate forming a seal. Negative pressure is then created inside the plate using a needle, as described above. After this vacuum is created, there is enough force generated to keep the plates sealed together. Over time, as the internal vacuum decreases due to effluent collection, the plates will eventually release from each other. At this point, perfusion stops and the process can be repeated to continue on the experiment. To separate the plates while there is still internal negative pressure, the same needle used to create a vacuum can be used to introduce more air into the system. This will reduce the vacuum pressure and allow the plates to separate.

The second additional aspect is a mechanism to ensure that there is no cross contamination between effluent chambers. This can involves two components: a hollow cylinder extending down from the well into the effluent collection chamber and a post that protrudes up into the cylinder near the filter. The cylinder can extend downwards below the height of the dividers between collection wells. This makes it difficult for effluent to travel in between the collection wells. The other feature, the post, extends upwards from the base plate to just below the filter. As perfusion progresses, the liquid effluent will collect on the bottom of the filter and form a droplet. This droplet will then touch off onto the post and wick down into the effluent collection chamber. These two features can be used together or separately to ensure individual collection of liquid effluent with no cross contamination.

Aspects of the above mechanism can include one or more of the plates, posts, or skirts being constructed of or coated with a hydrophobic material, or hydrophilic material, depending upon how one chooses the effluent flow to go into a chamber.

FIGS. 26, 27, 28a and 28b, 29a and 29b illustrate such additional aspects of bioreactor systems as described herein.

FIG. 26 is a photograph of an embodiment of a multi-well high throughput bioreactor system 2000 as described herein.

Figure 27:
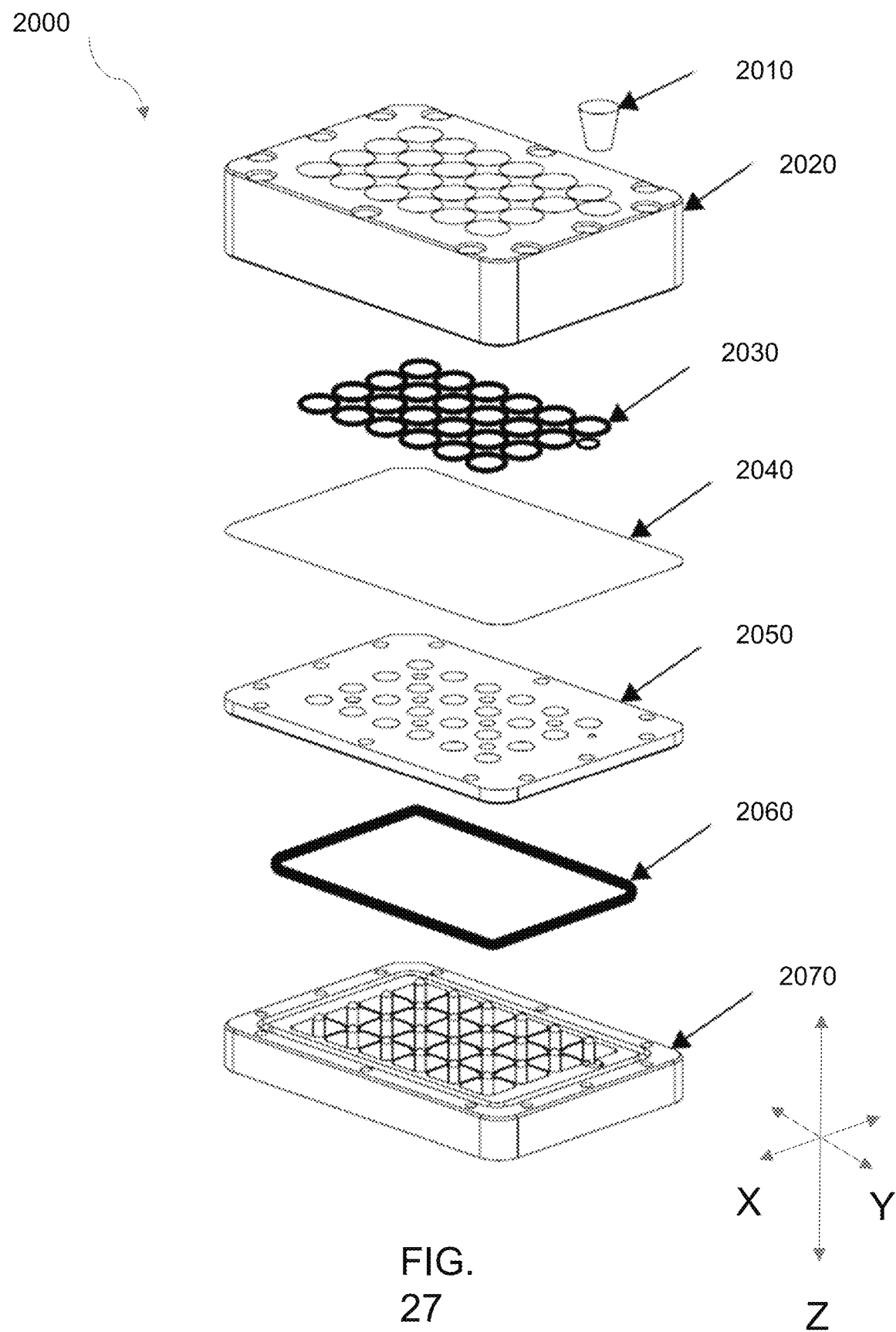
FIG. 27 is an exploded view illustration of the embodiment 2000 of FIG. 26.

FIG. 27 is an exploded view illustration of the embodiment 2000 of FIG. 26. Such a high-throughput setup is comprised of a top plate 2020, filter plate 2050, and effluent (i.e. media) collection chamber 2070. When assembled, the plates form a "sandwich" configuration with the top plate 2020 on top, the filter plate 2050 underneath the top plate 2020 with a filter 2040 and gaskets (or o-rings) 2030 to form a seal between the top plate 2020 and filter plate 2050. The effluent collection chamber 2070 is underneath the filter plate 2050 with one or more gaskets or o-rings 2060 in between the filter plate 2050 and effluent chamber 2070. 2010 is a self-healing annular seal that fits in the upper opening of each well of the top plate 2020 that can receive a vacuum source apparatus, such as a needle.

Figures 28A, 28B:
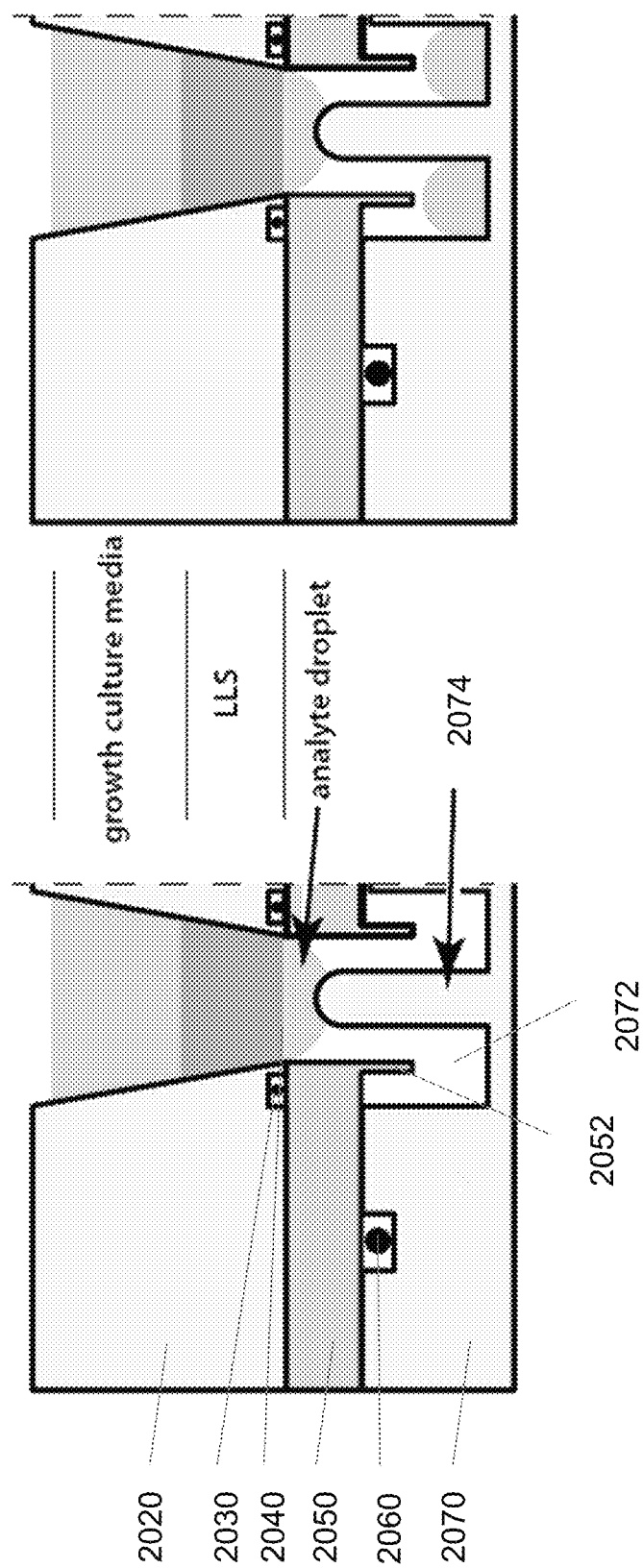
FIGS. 28A-28B are an enlarged view of an embodiment of a configuration of structures of the embodiment 2000 for facilitated the collection of analyte into individual effluent collection chambers while minimizing cross-contamination.

FIGS. 28A and 28B are illustrations of an embodiment of a configuration of structures to facilitate efficient collection of the analyte into single well of the effluent chamber 2070 while preventing cross-contamination of the wells in the multi-well high throughput bioreactor system 2000. A wicking post 2072 can extend upward from a surface of the effluent chamber 2070 towards the filter plate 2050 to help collect analyte pushed through the filter 2040 and filter plate 2050 from the wells of the top plate 2020. This collection can be facilitated by a skirt 2052, which is an annular lip around the diameter of the wells of the filter plate 2050 that extends downward from the filter plate 2050 towards the effluent chamber 2070. The filter plate 2050 and/or skirt 2052 can be constructed of or coated with a hydrophobic material. It can optionally be constructed from or coated with a hydrophilic material as well. FIG. 28A shows as the analyte drops from the bottom of the filter 2040 supported by the filter plate 2050 into the effluent well 2072 of the effluent chamber 2070. FIG. 28B shows analyte collected in the well 2072. The arrangement of skirt 2052 and post 2072 is an embodiment, and one of skill in the art would understand that a configuration of skirt-only or post-only is also plausible.

Figure 29A:
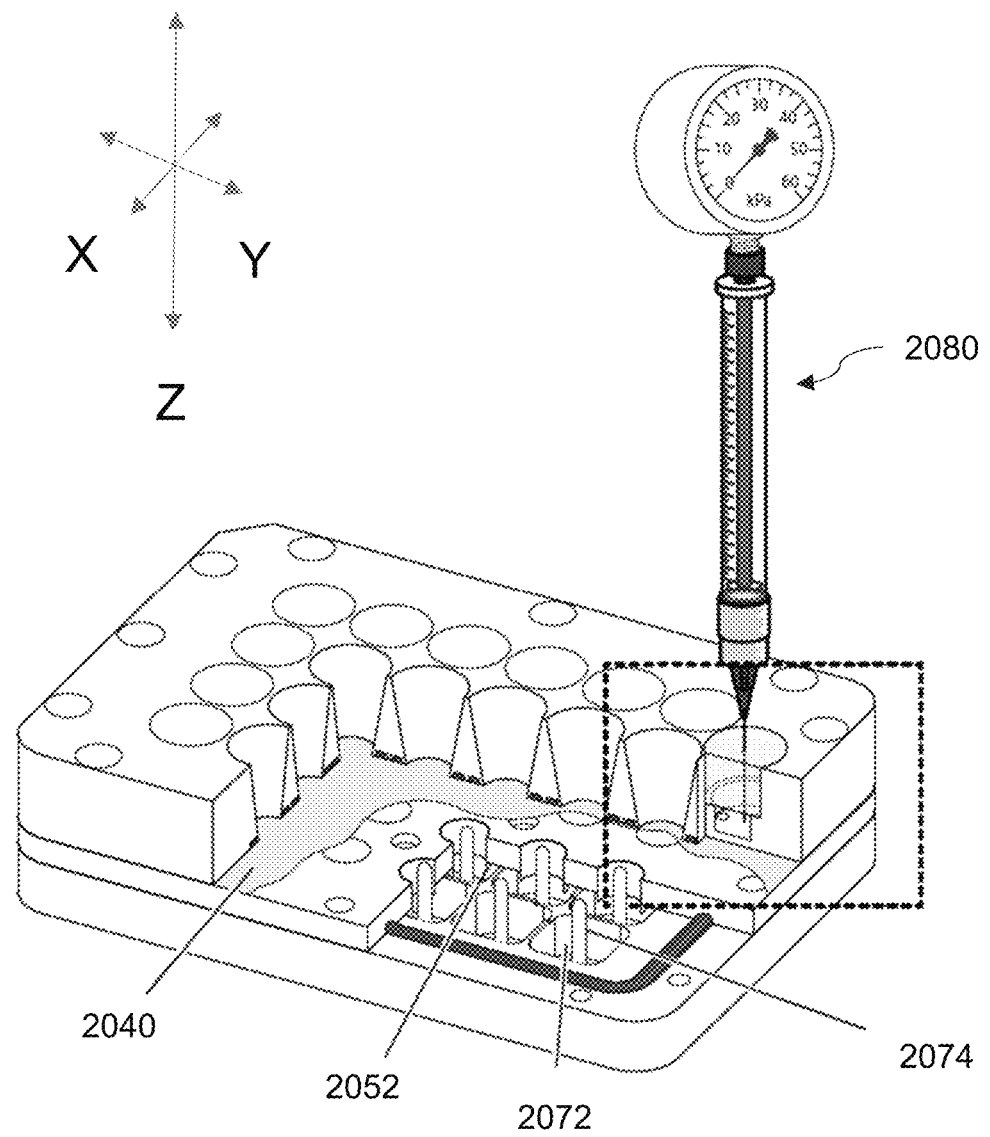

FIG. 29A is a cross-sectional perspective view of the embodiment 2000 with a pressure generating apparatus 2080 inserted into the self-healing annular seal 2010. The pressure generating apparatus 2080 has a pressure gauge to monitor the pressure, and comprises a needle and syringe with which negative or positive pressure can be created to drive the flow of fluid through the bioreactor columns created by the plate assembly. FIG. 29B is an enlarged view of insertion of a needle from the pressure generating apparatus 2080 into the self-healing annular seal 2010 of the embodiment 2000.

Figure 30:
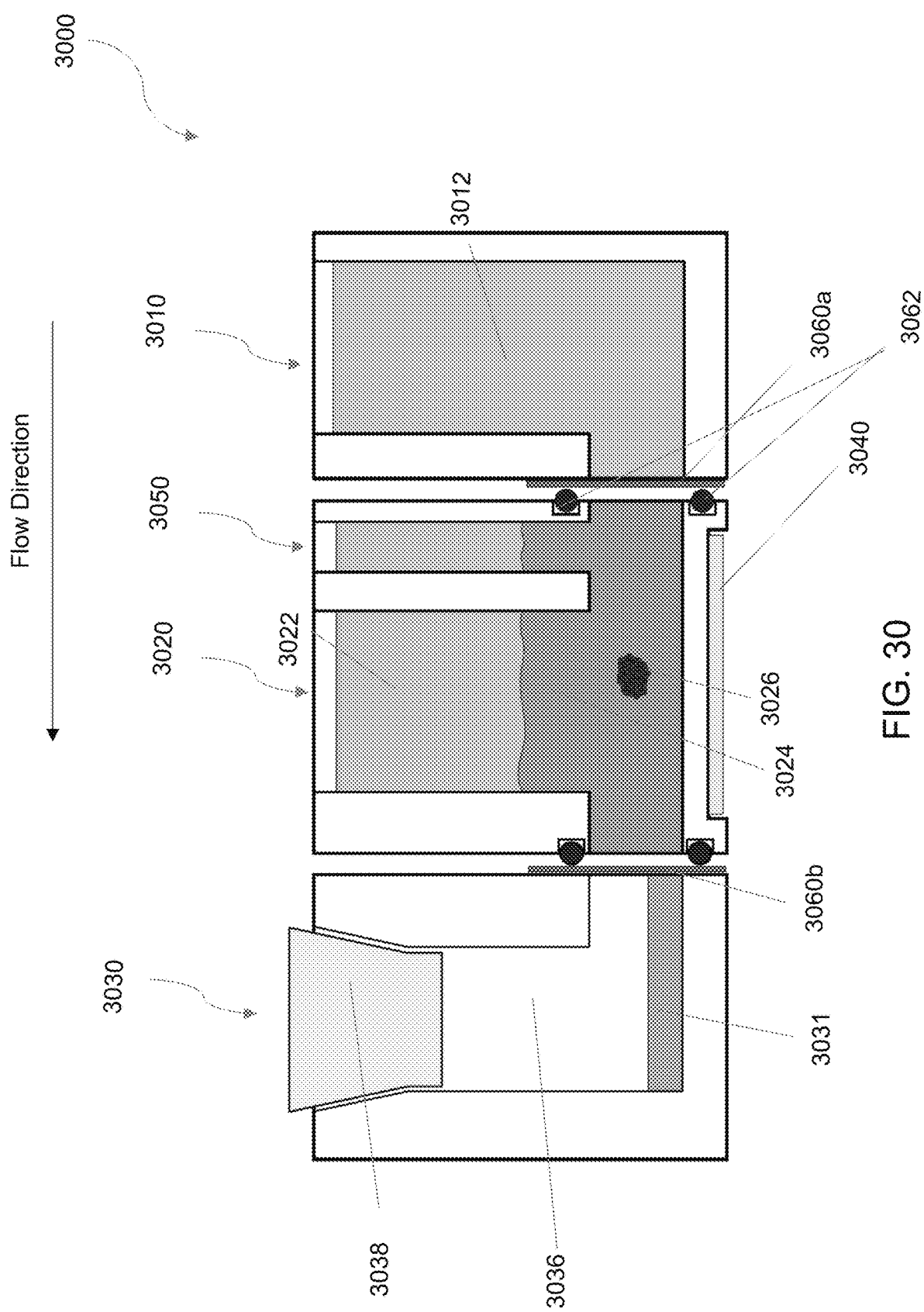
FIG. 30 is an embodiment of a perfusion-enabled bioreactor 3000 as described herein.

An alternate embodiment of a bioreactor system 3000 as described herein is shown in FIG. 30. The bioreactor system 3000 of FIG. 30 involves a three-piece design, in which the filtering mechanism is a nanoporous polycarbonate filter membrane 3060a and 3060b rather than another material such as a 3D hydrogrel. The first piece on the right is comprised of a feeder well 3010 in which the liquid growth media 3012 is placed. The second piece in the center is the culturing well 3020 in which the LLS 3024 and biological sample 3026 are located, in addition to culture media 3022. The liquid growth media 3012 flows from the feeder well 3010 into the culturing well 3020 through a filter membrane 3060a. This filter membrane 3060a is sealed using one or more O-rings 3062. After the liquid growth media 3012 flows through the LLS 3024, it flows through a second membrane 3060b on the left, which can be sealed in the same manner 3062 as the first filter 3060a. The liquid effluent 3031 is then collected in the effluent chamber 3030, which is shown on the left. All three pieces can be clamped and compressed together using fasteners or glue (not shown). A single chamber connects the feeder well 3010 to the culture chamber 3020 to the effluent chamber 3030, in which the liquid growth media 3012 flows from one well to the next. After assembly, a glass coverslip 3040 is affixed to the bottom of the plate to allow the viewing and microscopy of the culturing well 3020. Vacuum pressure can be created in the chamber 3038 of the effluent collection well 3030 through a self-healing plug 3038 or screw mechanism that has previously been described. Variations of this configuration can also involve a higher throughput design, containing multiple culture wells in one plate.

Elastomeric Negative Pressure Devices

In some embodiments, the herein disclosed bioreactor systems utilize elastomeric negative pressure devices to apply a negative gage pressure and allow perfusive flow through a porous support medium enabling 3D growth of biological samples and methods of use. The negative gage pressure can be a constant negative gage pressure. Elastomeric negative pressure devices as described herein can have a constant wall thickness that allows for the generation of a known and constant negative pressure.

Described herein are embodiments of negative pressure devices and embodiments of a passive negative pressure system that can be applied to current cell biology infrastructure and has other potential uses as well. Described herein are passive suction devices (also referred to herein as elastomeric pressure vessels, negative gage pressure vessels, elastomeric negative pressure vessels, passive constant negative pressure devices, thin walled pressure vessel, thin walled elastomeric tube, and the like), particularly to create low vacuum pressures over time periods spanning hours or days, for the purposes of perfusing liquid through a porous medium. Passive suction devices as described herein are comprised of a deformable thin walled pressure vessel in the shape a cylinder with hemispherical ends. There is one inlet/outlet that is connected to the collection side of the 3D cell culture device.

Variations of this assembly include a tube that can be connected to the perfusion plate and on the other end connected to "vacuum hub" with a passive suction device attached. By connecting the plate with tubing, several plates could be hooked up to the hub and therefore connected to the same passive suction device. Suction is created when the user compresses the thin walled pressure vessel, attaches it to the cell culture device, and then releases the pressure vessel. The pressure vessel will try to expand back to its original shape, therefore creating a negative pressure inside. The negative pressure will draw fluid through the porous gel at a rate proportional to the change in pressure over the medium. The expected volume of effluent to be collected is much less than the volume that is displaced by the compression of the pressure vessel, thus maintaining an approximately constant negative pressure differential.

Novel aspects of the negative pressure devices and systems as described herein include visual feedback, ease of use, and potential to calibrate the device to the desired pressure differential. As the suction device fills with air over time, the user has a visual indicator that the vacuum must be reset. This also aids in immediate verification that the device is sealing properly. The device is also very user friendly as it takes little force to compress, is simple to connect, and is disposable or autoclavable depending on material. In addition, the pressure differential created is ultimately dependent on the geometry and material properties of the device, not on its deformation. This means that each device of the same material but different size has its own unique pressure capabilities. These can be manufactured in a way that a user could purchase each device for a specific calibrated pressure differential.

In certain aspects, systems as disclosed herein utilizing elastomeric negative pressure vessels improves upon the current standard by introducing a specialized jammed microgel system that allows for cellular migration and perfusion and is experiment ready as soon as the cells are placed within it. The device that houses this gel includes a filter and a vacuum system which allows the nutrient media to perfuse through the system without disturbing the cellular environment. Since the perfusion relies on a vacuum, pulsatile flow, which can affect cell behavior, can easily be achieved. Furthermore, this system allows for continuous optical access during the growth of the biological samples.

In certain aspects, disclosed herein is a bioreactor system that utilizes an elastomeric pressure vessel that can be fluidically connected (for example by an interference fit with the vessel or an intermediate plastic tube) with a multi-well, or continuous-well, platform with optional integrated optical pathways for direct observation of biological samples in bioreactor units. Perfusive flow is used through a porous support medium in the bioreactor enabling 3D growth of biological samples. Optical pathways enable microscopy of biological samples without interruption of perfusion and allows long-term growth and behavior to be studied without disturbing the environment.

In standard 3D cell culture conditions, in a medium such as Matrigel, the inability to add fresh nutrients or remove waste from the system results in two possible outcomes: the cells must be removed from Matrigel and nourished elsewhere, or the cells will eventually die as their waste collects around them. A way to combat this issue is through the perfusion of cell growth media through a porous gel medium, called a liquid-like solid. In this system, described in PCT/US2019/017316, perfusion is achieved through a negative pressure differential on the collection side of the gel medium. A constant negative pressure is desirable to ensure a steady flow rate through the gel. The following example describes a passive negative pressure system that can be applied to current cell biology infrastructure and has other potential uses as well.

Elastomeric pressure vessels have been described previously, for example in U.S. Pat. No. 5,073,347 ("the '347' patent"). The transfer pipette in the '347 patent is a device made to collect a specific volume of liquid consistently. The device as described in the '347 patent does not recognize or otherwise teach wall thickness as a controlled parameter in their manufacturing process to determine the function of the device. Wall thickness is discussed in the '347 patent in regard to their manufacturing process (blow molding) and how it would affect the volume of fluid collected if the thickness is inconsistent. Wall thickness is further discussed in the '347 patent in regard to varying the wall thickness for different regions of the bulb to aid in assembly.

Passive Negative Pressure Devices as described herein recognize or otherwise stipulates wall thickness as a crucial parameter in the function of the device. By controlling the wall thickness for a given geometry and material, the negative pressure generated can be precisely controlled, irrespective of the volume of fluid drawn into the bulb. In short, the Passive Negative Pressure Device is a pressure controlling device, and the device of the '347 patent is a volume controlling device.

According to aspects of the present disclosure, the amount of negative pressure generated can be controlled as a function of wall thickness. Furthermore, the effective pressure doesn't increase and it spreads out the area over which the force is acting. With a known geometry and stiffness (elastic modulus), the pressure can be known (pressure on the order of pascals or kilopascals).

With previously described systems, a screw or syringe was used as a negative pressure actuator. By activating the actuator, a fixed volume was pulled out. Once the fluid began to flow, the fluid fills the void, and the actual measured pressure begins to change.

Elastomeric negative pressure vessels as described herein are simple to use. They keep the flow rate constant as a result of constant negative pressure, which can improve properties of perfusion in systems employing such elastomeric pressure vessels.

This example relates to passive suction devices, particularly to create low vacuum pressures over time periods spanning hours or days, for the purposes of perfusing liquid through a porous medium. In certain aspects, the pressure is constant negative pressure. In an embodiment, the suction device (i.e. vacuum source or negative pressure device) is comprised of a deformable thin walled elastomeric pressure vessel in the shape a cylinder with hemispherical ends. There is one inlet/outlet that is connected to the collection side of the 3D cell culture device. Variations of this assembly include a tube that can be connected to the perfusion plate and on the other end connected to "vacuum hub" with a passive suction device attached. By connecting the plate with tubing, several plates could be hooked up to the hub in series or in parallel and therefore connected to the same passive suction device. Suction is created when the user compresses the thin walled pressure vessel, attaches it to the cell culture device, and then releases the pressure vessel. The pressure vessel will try to expand back to its original shape, therefore creating a negative pressure inside. The negative pressure will draw fluid through the porous gel at a rate proportional to the change in pressure over the medium. The expected volume of effluent to be collected is much less than the volume that is displaced by the compression of the pressure vessel, thus maintaining an approximately constant negative pressure differential. Thin walled elastomeric pressure vessels as described herein can be designed for a specific constant pressure rate by altering modulus and/or geometry of the material (thickness, radius, etc).

Novel aspects of embodiments of the present example include visual feedback, ease of use, and potential to calibrate the device to the desired pressure differential. As the suction device fills with air over time, the user has a visual indicator that the vacuum must be reset. This also aids in immediate verification that the device is sealing properly. The device is also very user friendly as it takes little force to compress, is simple to connect, and is disposable or autoclavable depending on material. In addition, the pressure differential created is ultimately dependent on the geometry and material properties of the device, not on its deformation. This means that each device of the same material but different size has its own unique pressure capabilities. These can be manufactured in a way that a user could purchase each device for a specific calibrated pressure differential.

Figure 31B:
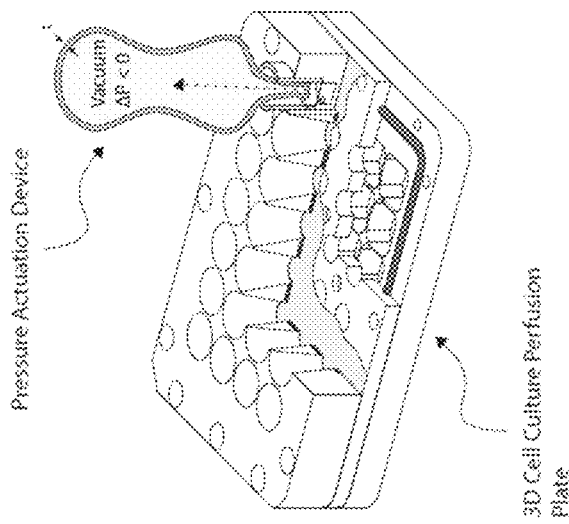
FIGS. 31A and 31B show an embodiment of a system as described herein, comprising an elastomeric negative pressure device as described herein in conjunction with a 3D cell culture perfusion plate as described herein. The "off" state ($\Delta P=0$) is shown in FIG. 31A and the "on" state ($\Delta P<0$) is shown in FIG. 31B.
Figure 31A:
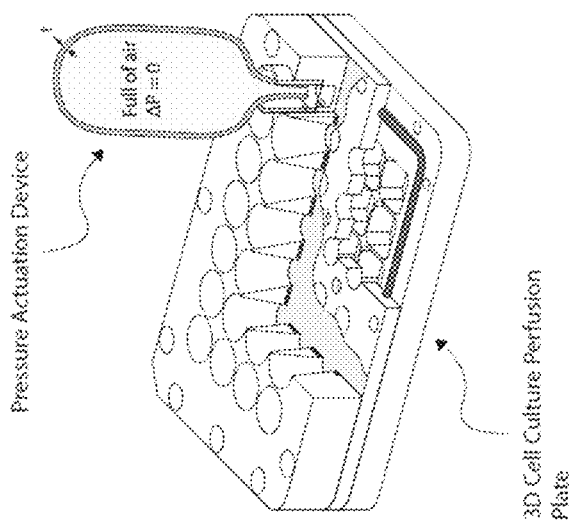

See FIGS. 31A and 31B below for examples, which can be suitable for or otherwise adapted for imaging and multi-well high throughput plates according to teachings of the present disclosure.

As described herein, the negative pressure generated in the bulb of the device is dependent on the elastic modulus of the material and the geometry of the bulb. In manufacturing, the geometry and material properties are able to be kept the same, with variability allowed in only the thickness of the wall of the bulb. This could be achieved with an injection molding process, a blow molding process, or various other methods. Adjusting the wall thickness allows for change in the pressure generated in the device.

According to devices as described herein, the negative pressure developed in the bulb of a passive negative pressure device is proportional to the product of the elastic modulus and the ratio of the wall thickness to the bulb radius squared. In equation form this is as follows:

$$P = CE\left(\frac{t}{R}\right)^2 \tag{eq. 1}$$

where P, is the pressure, E is the elastic modulus, t is the wall thickness, R is the radius of the cylindrical section of the device, and C is the constant of proportionality which is unitless.

The constant of proportionality must be determined experimentally for a given bulb geometry and material. This is done by attaching the bulb to a U-tube manometer, measuring the pressure developed, and then solving the above equation for the constant of proportionality, C. Once this constant is determined, the user is then able to predict the negative pressure that will be developed in a bulb of the same material with different geometries. That is, one could then vary the wall thickness and accurately predict the constant negative pressure that will be generated. Based on the mathematical relationship above, it would be within the realm of ordinary for the skilled artisan to determine a material and wall thickness to provide a desired pressure for a given system.

Without intending to be limiting, suitable elastomeric materials that can be used for this device include, for example, polyethylene, silicon rubber, polyvinylchloride (PVC), polyurethane (PUR), and nitrile rubber (NBR), although the skilled artisan would recognize that other materials may be suitable. In certain embodiments, passive negative pressure devices comprise low density polyethylene or silicone rubber. The constant of proportionality for these has been determined and provided for these materials, and tables of wall thickness versus vacuum pressure for these materials are shown below in Tables 1 and 2.

For example, Table 1 demonstrates that a bulb of the geometry described herein made of low-density polyethylene (elastic modulus of 0.355 GPa) has the following relationship between pressure and wall thickness of devices as described herein:

TABLE 1

Relationship between Pressure and Wall Thickness (low-density polyethylene)

| Wall thickness (mm) | Vacuum Pressure (Pa) |
| --- | --- |
| 0.40 | 4327 |
| 0.50 | 6760 |
| 0.60 | 9735 |
| 0.70 | 13250 |
| 0.80 | 17310 |
| 0.90 | 21900 |
| 1.00 | 27040 |

Table 2 demonstrates that a bulb of the geometry described herein made of silicon rubber (elastic modulus of 1.0 GPa) has the following relationship between pressure and wall thickness of devices as described herein:

TABLE 2

Relationship between Pressure and Wall Thickness (silicon rubber)

| Wall thickness (mm) | Vacuum Pressure (Pa) |
| --- | --- |
| 0.40 | 15000 |
| 0.50 | 23440 |
| 0.60 | 33750 |
| 0.70 | 45900 |
| 0.80 | 80000 |
| 0.90 | 75900 |
| 1.00 | 93750 |

Furthermore, elastomeric vessels according to the present disclosure can further comprise a detachable tubing that can connect the pressure vessel to perfusion-enabled systems as further described below.

Adapter Plugs for Connecting Passive Negative Pressure Devices

Figure 32A:
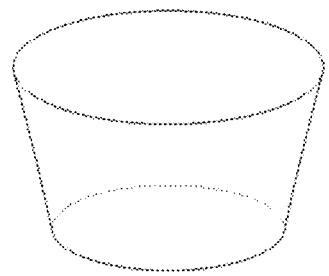
FIGS. 32A and 32B are non-limiting embodiments of adapters for connecting negative pressure devices to bioreactors and/or bioreactor plates as described herein.
Figure 32B:
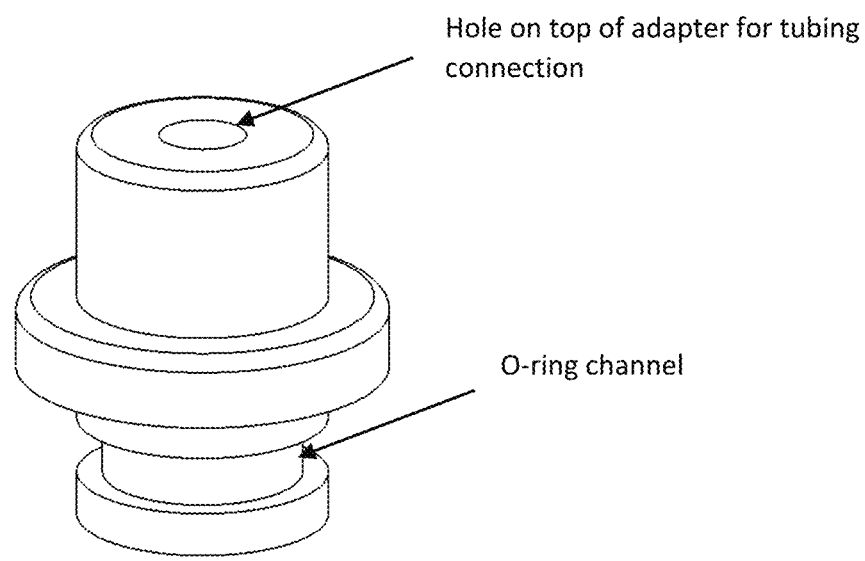

FIGS. 32A and 32B show two non-limiting examples of adapter plugs that can be used to attach passive negative pressure devices to the 3D bioreactor perfusion plates or other aspects of systems as described herein. FIG. 2A is a molded Momentive (brand name material) plug that is tapered to fit into a hole in a perfusion plate. The plug material is self-healing, meaning that a passive negative pressure device can be inserted into it to create an airway, and the plug will seal around the negative pressure device opening and thus the suction actuation is possible. FIG. 32B is another plug adapter that can be used for connecting negative pressure devices to embodiments of some of the 3D bioreactor perfusion plates as described herein. It is designed to fit into a hole on a bioreactor plate and seal using an O-ring (O-ring channel indicated on figure below). If tubing were to be used to connect the passive negative pressure device, then the tubing can be inserted into the hole on top of the adapter plug (as shown in FIG. 32B) to create the seal and allow for suction actuation. The skilled artisan would understand that these are two representative non-limiting examples, and other materials and configurations of adapter plugs can be used to attach negative pressure devices to systems as described herein as needed.

Connecting Multiple Plates

Figure 33:
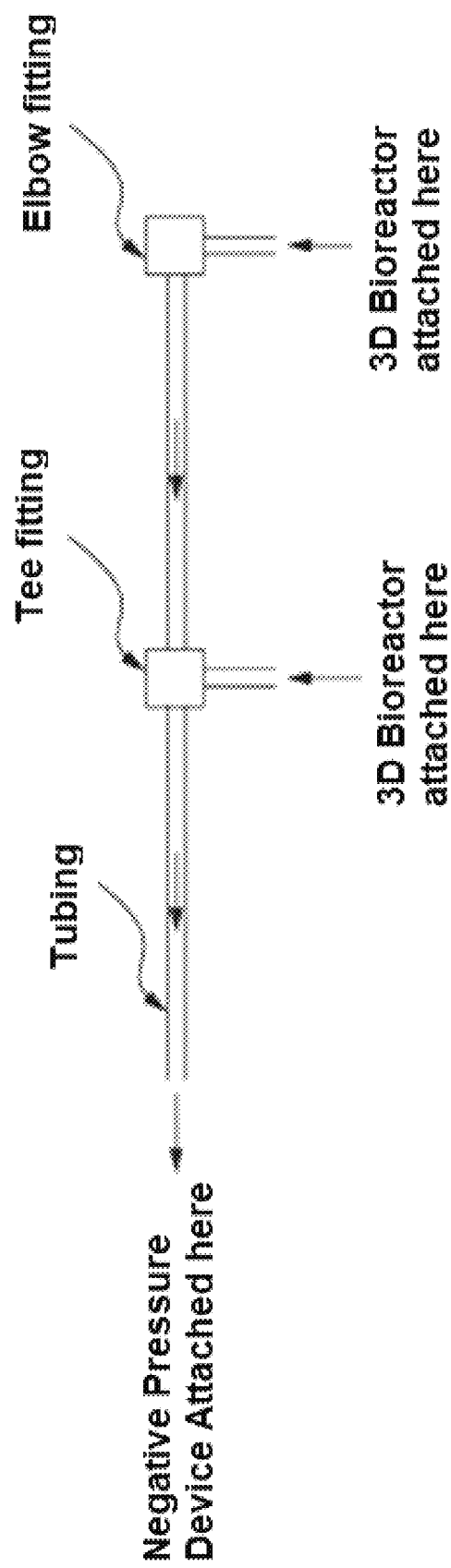
FIG. 33 is a schematic showing an embodiment of connecting multiple bioreactors and/or well plates within the same system.

A non-limiting schematic of one possible configuration for the connection of multiple 3D bioreactor plates within the same system is shown in FIG. 33. Other configurations are possible.

Nevertheless, it will be understood that various modifications may be made without departing from the spirit and scope of the present disclosure. Accordingly, other embodiments are within the scope of the following claims.

Unless defined otherwise, all technical and scientific terms used herein have the same meanings as commonly understood by one of skill in the art to which the disclosed present disclosure belongs. Publications cited herein and the materials for which they are cited are specifically incorporated by reference.

Those skilled in the art will recognize, or be able to ascertain using no more than routine experimentation, many equivalents to the specific embodiments of the present disclosure described herein. Such equivalents are intended to be encompassed by the following claims.

In addition, the following embodiments and features can be incorporated into one or more aspects or embodiments as provided herein. The following are provided to illustrate additional features that can be incorporated together with embodiments provided above and herein as well as with one or more of each other. The present disclosure is not limited to each feature independently, rather various combinations of one or more of these features with one or more of the features disclosed above and herein in contemplated.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A microscopy-enabled bioreactor system, comprising:
   one or more bioreactor units, wherein each of the one or more bioreactor units comprises:
   a sample well filled with a three-dimensional (3D) cell growth medium, wherein the 3D cell growth medium comprises a plurality of hydrogel particles and a liquid cell culture medium, wherein the hydrogel particles are swelled with the liquid cell culture medium to form a granular gel,
   a medium collection chamber fluidly connected to the sample well by a first filter material; and a liquid medium reservoir fluidly connected to the sample well by a second filter material, wherein the system is further configured so that the application of negative gage pressure to the medium collection chamber or positive pressure to the liquid medium reservoir perfuses fluid from the liquid medium reservoir, through the second filter material then through the three-dimensional cell growth medium, through the first filter material, and finally into the medium collection chamber;
   wherein the system is configured so that application of negative gage pressure to the medium collection chamber or positive pressure to the sample well actively permeates fluid from the sample well through the three-dimensional cell growth medium, through the first filter material, and finally into the medium collection chamber;
   wherein the first filter material has a porosity smaller than the size of the swollen hydrogel particles,
   wherein the bottom of the sample well is optically transparent.

2. The system of claim 1, further comprising a vacuum apparatus operably connected to the medium collection chamber.

3. The system of claim 2, wherein the vacuum apparatus comprises a screw-driven actuator, the screw-driven actuator comprising a set actuation screw rotatably mounted within the medium collection chamber configured to actively provide negative gauge pressure to the medium collection chamber.

4. The system of claim 1, wherein the medium collection chamber comprises a vacuum port fluidly connected to the medium collection chamber that is releasably connectable to a vacuum apparatus.

5. The system of claim 1, comprising an array of isolated sample wells.

6. The system of claim 5, wherein each of the isolated sample wells in the array are fluidly connected to separate liquid medium reservoirs.

7. The system of claim 5, wherein each of the isolated sample wells in the array are fluidly connected to the same liquid medium reservoir.

8. The system of claim 1, wherein the system has an annular arrangement comprising an outer ring, a middle ring, and a central chamber,
   wherein the liquid medium reservoirs is located in the outer ring,
   wherein the sample well is located in the middle ring, and
   wherein the center chamber is the medium collection chamber.

9. The system of claim 1, wherein the system has an annular arrangement comprising an outer ring and a central chamber,
   wherein the sample well is located in the central chamber,
   wherein the medium collection chamber is located in the outer ring, and
   wherein the liquid medium reservoirs is located above the sample well in the central chamber.

10. The system of claim 1, wherein the three-dimensional cell growth medium has a yield stress such that the cell growth medium undergoes a phase change from a first solid phase to a second liquid phase upon application of a shear stress greater than the yield stress.

11. The system of claim 1, wherein a plurality of cells are disposed in a region of the 3D cell culture medium.

12. The system of claim 1, wherein the one or more bioreactor units are configured for a horizontal flow path of fluid from the liquid medium reservoir to the sample well to the medium collection chamber.

13. The system of claim 1, further comprising a pipette guide configured to receive a pipette tip and provide a fixed height from the bottom of the sample well to the distal end of the pipette tip.

14. The system of claim 1, wherein the one or more bioreactor units are discrete units not in fluidic communication with one another having a horizontal flow path of fluid from liquid reservoir to sample well to medium collection chamber.

15. The system of claim 1, further comprising a cassette configured to securely store and transport a plurality of discrete bioreactor units.

16. The system of claim 15, wherein each of the discrete bioreactor units of the plurality comprises three or more apertures or annular frustroconical recesses on a bottom surface configured to receive a protrusion extending toward the top of the discrete unit.

17. The system of claim 15, wherein the cassette comprises a chamber configured to receive a plurality of bioreactor units, the chamber having a bottom surface with a plurality of recesses, each recess of the plurality configured to securely seat an individual bioreactor unit.

18. The system of claim 17, wherein each recess of the plurality of recesses of the bottom surface comprises three or more tapered frustroconical posts extending upwards from the bottom surface and tapering towards an end distal to the bottom surface, each of the tapered posts configured to protrude into and securely mate with the apertures or annular frustroconical recesses of the discrete bioreactor units.

19. The system of claim 15, wherein the cassette further comprises a gas port.

20. The system of claim 15, wherein the cassette is operably connected to a heat source.

21. The system of claim 12, further comprising an injection port for drug delivery in fluid connection with the horizontal flow path positioned in the flow path between the liquid reservoir and the sample reservoir.

22. A method of using a perfusion-enabled bioreactor, comprising:
   providing one or more bioreactor systems of claim 1;
   providing a biological sample;
   providing a 3D growth media;
   placing the 3D growth media in a culture chamber of the bioreactor;
   pipetting the biological sample into the 3D growth media;

applying a positive or negative gage pressure to the bioreactor thereby drawing fluid into the 3D growth media through active perfusion.

23. A high-throughput bioreactor system, comprising:

a well plate, wherein the well plate comprises a plurality of apertures, each of the plurality of apertures comprising a sample well filled with a three-dimensional (3D) cell culture growth medium, wherein the 3D cell culture medium comprises a plurality of hydrogel particles and a liquid cell culture medium, wherein the hydrogel particles are swelled with the liquid cell culture medium to form a granular gel;

a filter;

a center plate, the center plate comprising a plurality of apertures; and a base plate, the base plate comprising one or more medium collection chambers fluidly connected to the sample well by a filter material;

wherein the bottom of the well plate is configured to mate with the top of center plate and sandwich the filter, the bottom of the center plate configured to mate with the top of the base plate, so that when mated, the sample wells of the well plate are in fluidic communication with the center plate through the filter, the center plate being in fluidic communication with the one or more medium collection chambers thereby forming a plurality of bioreactors having a vertical fluid flow path from the well plate through the filter and center plate to the base plate;

wherein the system is configured so that application of negative gage pressure to the medium collection chamber actively draws fluid from the sample well where it permeates the three-dimensional cell growth medium, through the filter, and finally into the medium collection chamber; and wherein the filter material has a porosity smaller than the size of the swollen hydrogel particles.

24. A dual-flow bioreactor system, comprising:

a first liquid reservoir;

a sample well, wherein the sample well is filled with a three-dimensional (3D) cell growth medium, wherein the 3D cell culture medium comprises a plurality of hydrogel particles and a liquid cell culture medium, wherein the hydrogel particles are swelled with the liquid cell culture medium to form a granular gel;

a first medium collection chamber;

a second liquid reservoir;

a second medium collection chamber;

a first vacuum apparatus;

a second vacuum apparatus;

wherein the first vacuum apparatus is operably connected to the first medium collection chamber;

wherein the second vacuum apparatus is operably connected to the second medium collection chamber;

wherein the first liquid reservoir is in fluidic communication with the sample well through a first filter material, which is in fluid communication with the first medium collection chamber through the first filter material, thereby forming a first perfusion flow path, wherein the first filter material has a porosity smaller than the size of the swollen hydrogel particles;

wherein the second liquid reservoir is in fluidic communication with the sample well through a second filter material, which is in fluidic communication with the second medium collection chamber through the second filter media, thereby forming a second perfusion flow path, wherein the second filter material has a porosity smaller than the size of the swollen hydrogel particles;

wherein the system is configured so that the first flow path and second flow path are orthogonal to one another and at different heights in the sample well from the bottom of the system;

wherein the system is further configured so that application of negative gage pressure to the first medium collection chamber, second medium collection chamber, or both, actively draws fluid from the first liquid reservoir, the second liquid reservoir, or both, where it permeates the three-dimensional cell growth medium, through the first filter, the second filter, or both, and finally into the first medium collection chamber, the second collection chamber, or both.

* * * * *